US007537888B2

(12) United States Patent
Georges et al.

(10) Patent No.: US 7,537,888 B2
(45) Date of Patent: May 26, 2009

(54) MARKER ASSISTED SELECTION OF BOVINE FOR IMPROVED MILK PRODUCTION USING DIACYLGLYCEROL ACYLTRANSFERASE GENE DGAT1

(76) Inventors: Michel Alphonse Julien Georges, 24 Rue Vieux Tige, B-4161 Villers-aux-Tours (BE); Wouter Herman Robert Coppieters, Beekstraat 2, B-3401 Landen (BE); Bernard Marie-Josee Jean Grisart, 2 Rue Bordia, B-4218 Couthuin (BE); Russell Grant Snell, 3/28 Tennyson Street, Balmoral, Auckland (NZ); Suzanne Jean Reid, ViaLactia Biosciences (NZ) Limited, P.O. Box 109-185, Newmarket Auckland (NZ); Christine Ann Ford, ViaLactia Biosciences (NZ) Limited, P.O. Box 109-185, Newmarket, Auckland (NZ); Richard John Spelman, 340 Horotiu Road, R.D. 8, Hamilton (NZ)

( * ) Notice: Subject to any disclaimer, the term of this patent is extended or adjusted under 35 U.S.C. 154(b) by 240 days.

(21) Appl. No.: 10/415,620

(22) PCT Filed: Oct. 31, 2001

(86) PCT No.: PCT/NZ01/00245

§ 371 (c)(1),
(2), (4) Date: Nov. 13, 2003

(87) PCT Pub. No.: WO02/36824

PCT Pub. Date: May 10, 2002

(65) Prior Publication Data

US 2004/0076977 A1     Apr. 22, 2004

(30) Foreign Application Priority Data

Oct. 31, 2000  (NZ) .................... 507888
Dec. 6, 2000   (NZ) .................... 508662

(51) Int. Cl.
*C12Q 1/68*    (2006.01)
*C12P 19/34*   (2006.01)
*C07H 21/02*   (2006.01)
*C07H 21/04*   (2006.01)

(52) U.S. Cl. ................. 435/6; 435/91.2; 536/23.1; 536/24.3

(58) Field of Classification Search ............ None
See application file for complete search history.

(56) References Cited

FOREIGN PATENT DOCUMENTS

WO   WO 9952942 A2 * 10/1999

OTHER PUBLICATIONS

Riguet etl al 'Fine-mapping of quantitative trait loci by identity by descent in outbred populations: application to milk production in dairy cattle.' Proc Natl Acad Sci U S A. Aug. 3, 1999;96(16):9252-7.*
Spelman et al 'Characterization of the DGAT1 gene in the New Zealand dairy population.' J Dairy Sci. Dec. 2002;85(12):3514-7.*
Kuhn et al 'Evidence for multiple alleles at the DGAT1 locus better explains a quantitative trait locus with major effect on milk fat content in cattle.' Genetics. Aug. 2004;167(4):1873-81.*
Lucentini 'Gene association studies typically wrong' The Scientist Dec. 20, 2004 p. 20.*
Hacker et al 'Lack of association between an interleukin-1 receptor antagonist gene polymorphism and ulcerative colitis.' Gut. May 1997;40(5):623-7.*
National Dairy Council 'Table 7—Nutrient composition of milks from different species' available online from http://www.nationaldairycouncil.org/NationalDairyCouncil/Nutrition/Products/table07.pdf.*
Pennisi E 'A closer look at SNPs suggests difficulties'.Science. Sep. 18, 1998;281(5384):1787-9.*
Bennewitz J et al 'The DGAT1 K232A mutation is not solely responsible for the milk production quantitative trait locus on the bovine chromosome 14.' J Dairy Sci. Feb. 2004;87(2):431-42.*
Grisart B et al 'Genetic and functional confirmation of the causality of the DGAT1 K232A quantitative trait nucleotide in affecting milk yield and composition.' Proc Natl Acad Sci U S A. Feb. 24, 2004;101(8):2398-403.*
Spelman RJ and Garrick DJ 'Effect of live weight and differing economic values on responses to selection for milk fat, protein, volume, and live weight.' J Dairy Sci. Oct. 1997;80(10):2557-62.*
AW446908, dbEST Id: 3857657, from www.ncbi.nlm.nih.gov, pp. 1 and 2.*
EMBL Accession No. AF059202, Oelkers P. et al. "*Homo sapiens* ACAT related gene product 1mRNA," Oct. 15, 1998.
EMBL Accession No. AF236018, Joyce et al., "*Cercopithecus aethiops* diacyl-glycerol acyltransferase mRNA," Aug. 12, 2000.
EMBL Accession No. AF078752, Cases et al., "*Mus musculus* diacylglycerol acyltransferase (Dgat) mRNA," Nov. 11, 1998.
Smith et al., "Obesity resistance and multiple mechanisms of triglyceride synthesis in mice lacking Dgat," Nature Genetics 25(1). pp. 87-90, 2000.

* cited by examiner

*Primary Examiner*—Jehanne S Sitton
*Assistant Examiner*—Stephen Kapushoc
(74) *Attorney, Agent, or Firm*—Knobbe, Martens, Olson & Bear LLP

(57) ABSTRACT

The present invention provides a method of genotyping bovine for improved milk production traits by determining the DGAT1 genotypic state of said bovine, wherein the DGAT1 gene and polymorphisms within said gene have been found to be associated with such improved milk production traits.

14 Claims, 34 Drawing Sheets

<222> (29)..(31)

<223> bases 1 to 3 of the Kozak recognition sequence. See the genomic s
equence from the start codon for bases 4 to 7 of the Kozak recogn
ition sequence or the DGAT1 cDNA for the complete recognition seq
uence.

acttggccgc ggcggggtgc gaactaaggc c

<212> DNA

<213> Bos taurus

<220>

<221> CDS

<222> (1)..(191)

<223> Exon 1 CDS, determined by alignment with an amino acid sequence deduced from the cDNA

<220>

<221> misc_signal

<222> (1)..(4)

<223> these bases correspond to bases 4 to 7 of the Kozak recognition sequence. See DGAT1 cDNA for the complete recognition sequence.

<220>

<221> CDS

<222> (3809)..(3896)

<223> Exon 2, determined by alignment with an amino acid sequence deduced from the cDNA

<220>

<221> CDS

<222> (5840)..(5880)

<223> Exon 3, determined by alignment with an amino acid sequence deduced from the cDNA

<221> CDS

<222> (5960)..(6045)

<223> Exon 4, determined by alignment with an amino acid sequence deduced from the cDNA

<220>

<221> CDS

<222> (6138)..(6190)

<223> Exon 5, determined by alignment with an amino acid sequence deduced from the cDNA

<220>

<221> CDS

<222> (6406)..(6511)

<223> Exon 6, determined by alignment with an amino acid sequence deduced from the cDNA

<220>

<221> CDS

<222> (6601)..(6714)

<223> Exon 7, determined by alignment with an amino acid sequence deduced from the cDNA

<220>

<221> CDS

<222> (6815)..(6889)

<223> Exon 8, determined by alignment with an amino acid sequence deduced from the cDNA

<221> variation

<222> (6824)..(6889)

<223> this sequence is deleted from the alternately spliced transcript.

<220>

<221> CDS

<222> (6960)..(7063)

<223> Exon 9, determined by alignment with an amino acid sequence deduced from the cDNA

<220>

<221> CDS

<222> (7154)..(7192)

<223> Exon 10, determined by alignment with an amino acid sequence deduced from the cDNA

<220>

<221> CDS

<222> (7271)..(7312)

<223> Exon 11, determined by alignment with an amino acid sequence deduced from the cDNA

<220>

<221> CDS

<222> (7386)..(7430)

<223> Exon 12, determined by alignment with an amino acid sequence deduced from the cDNA

<221> CDS

<222> (7505)..(7617)

<223> Exon 13, determined by alignment with an amino acid sequence deduced from the cDNA

<220>

<221> CDS

<222> (7705)..(7770)

<223> Exon 14, determined by alignment with an amino acid sequence deduced from the cDNA

<220>

<221> CDS

<222> (7858)..(7945)

<223> Exon 15, determined by alignment with an amino acid sequence deduced from the cDNA

<220>

<221> CDS

<222> (8027)..(8089)

<223> Exon 16, determined by alignment with an amino acid sequence deduced from the cDNA

<220>

<221> CDS

<222> (8162)..(8314)

<223> Exon 17 CDS, determined by alignment with an amino acid sequence deduced from the cDNA

FIGURE 2b continued

```
<220>
<221> misc_feature
<222> (8315)..(8317)
<223> translation stop codon

<220>
<221> polyA_site
<222> (8572)..(8578)
<223>

<220>
<221> variation
<222> (626)..(626)
<223> thymidine (T) to guanine (G) substitution polymorphism <220>
<221> variation
<222> (3512)..(3512)
<223> thymidine (T) to guanine (G) substitution polymorphism <220>
<221> variation
<222> (4040)..(4040)
<223> thymidine (T) to cytosine (G) substitution polymorphism <220>
<221> variation
<222> (4963)..(4963)
<223> adenine (A) to guanine (G) substitution polymorphism
```

<221> variation

<222> (5003)..(5003)

<223> guanine (G) to adenine (A) substitution polymorphism

<220>

<221> variation

<222> (5997)..(5997)

<223> cytosine (C) to thyamine (T) substitution polymorphism

<220>

<221> variation

<222> (6829)..(6830)

<223> adenine (A)-adenine (A) to guanine(G)-cytosine (C) substitution p
      olymorphism
      AA corresponds to the Q allele
      GC corresponds to the q allele

<220>

<221> variation

<222> (6892)..(6892)

<223> guanine (G) to adenine (A) substitution polymorphism

<220>

<221> variation

<222> (7224)..(7225)

<223> guanine (G)-guanine (G) to adenine (A)-cytosine (C) substitution
      polymorphism
      GG-AC
```

FIGURE 2b continued

```
<220>
<221>  variation
<222>  (7438)..(7438)
<223>  adenine (A) to guanine (G) substitution polymorphism <220>
<221>  variation
<222>  (7456)..(7456)
<223>  cytosine (C) to thymidine (T) substitution polymorphism <220>
<221>  variation
<222>  (7987)..(7987)
<223>  guanine (G) to adenine (A) substitution polymorphism <220>
<221>  variation
<222>  (8402)..(8402)
<223>  ctosine (C) to thymidine (T) substitution polymorphism <220>
<221>  misc_feature
<222>  (9434)..(9434)
<223>  ambiguous nucleotide <220>
<221>  misc_feature
<222>  (9496)..(9496)
<223>  ambiguous nucleotide
```

<221> misc_feature

<222> (10402)..(10417)

<223> ambiguous nucleotides

<220>

<221> primer_bind

<222> (6579)..(6601)

<223> Primer 17F
CCTGAGCTTGCCTCTCCCACAGT

<220>

<221> primer_bind

<222> (7036)..(7058)

<223> Primer 18R
CCAGGAGTCGCCGCAGCAGGAAG
reverse primer

<220>

<221> primer_bind

<222> (7280)..(7303)

<223> Primer 6F
CCGGCCATCCAGAACTCCATGAAG

<220>

<221> primer_bind

<222> (7585)..(7605)

<223> Primer AW446985 dn1
TAGAACTCGCGGTCTCCAAAC
reverse primer

<221> primer_bind

<222> (8222)..(8244)

<223> Primer InsUp1
TGGCTGTCACTCATCATCGGGCA

<220>

<221> primer_bind

<222> (8566)..(8589)

<223> Primer 14R2
TTGCACAGCACTTTATTGACACA

<220>

<221> primer_bind

<222> (6813)..(6830)

<223> Primer SNP1_FAM
AGC TTT GGC AGG TAA GGC

<220>

<221> primer_bind

<222> (6813)..(6830)

<223> Primer SNP1_HEX
AGC TTT GGC AGG TAA GAA

<220>

<221> primer_bind

<222> (6831)..(6844)

<223> Primer SNP1_2P
GGC CAA CGG GGG AG

<221> primer_bind

<222> (7424)..(7438)

<223> Primer SNP2_FAM
GCT GGC GGT GAG TGA

<220>

<221> primer_bind

<222> (7424)..(7438)

<223> Primer SNP2_HEX
GCT GGC GGT GAG TGG

<220>

<221> primer_bind

<222> (7439)..(7453)

<223> Primer SNP2_2P
CCT GCT GGG TGG GGA

<220>

<221> primer_bind

<222> (7442)..(7456)

<223> Primer SNP3_FAM
GCT GGG TGG GGA CGC

<220>

<221> primer_bind

<222> (7442)..(7456)

<223> Primer SNP3_HEX
GCT GGG TGG GGA CGT

<221> primer_bind

<222> (7457)..(7470)

<223> Primer SNP3_P
GTG GGG GCG GGT GG

<220>

<221> primer_bind

<222> (8388)..(8402)

<223> Primer SNP4_FAM
TGC CCC AAC CTG GGT

<220>

<221> primer_bind

<222> (8388)..(8402)

<223> Primer SNP4_HEX
TGC CCC AAC CTG GGC

<220>

<221> primer_bind

<222> (8403)..(8417)

<223> Primer SNP4_2P
GCA GCA GGA GGA GGC

<220>

<221> primer_bind

<222> (6811)..(6830)

<223> Primer Dgat 21
GTAGCTTTGGCAGGTAAGAA

<221> primer_bind

<222> (6965)..(6984)

<223> Primer Dgat 22
GGGGCGAAGAGGAAGTAGTA
reverse primer

<220>

<221> primer_bind

<222> (6613)..(6632)

<223> Primer Dgat 23
TGGCCCTGATGGTCTACACC

<220>

<221> primer_bind

<222> (6829)..(6850)

<223> Primer Dgat 24B
GGGCAGCTCCCCCGTTGGCCGC
reverse primer

<220>

<221> primer_bind

<222> (6651)..(6670)

<223> Primer DgatforAD
TTCTCCTACCGGGACGTCAA

<220>

<221> primer_bind

<222> (6871)..(6890)

<223> Primer ReverseNZ
CCGCGGTAGGTCAGGTTGTC
reverse primer

<221> primer_bind

<222> (6825)..(6838)

<223> Probe ForAA (FAM)
CGTTGGCCTTCTTA

<220>

<221> primer_bind

<222> (6823)..(6836)

<223> Probe DgatADGC (VIC)
TTGGCCGCCTTACC

<220>

<221> primer_bind

<222> (6651)..(6670)

<223> Primer DgatforAD
TTCTCCTACCGGGACGTCAA

<220>

<221> primer_bind

<222> (6878)..(6972)

<223> Primer DgatrevAD
AAGTAGTAGAGATCGCGGTAGGTCA
reverse primer

<220>

<221> primer_bind

<222> (6825)..(6838)

<223> Probe ForAA (FAM)
CGTTGGCCTTCTTA

<221> primer_bind

<222> (6823)..(6836)

<223> Probe DgatADGC (VIC)
TTGGCCGCCTTACC

<220>

<221> primer_bind

<222> (6652)..(6671)

<223> Primer DgatforRT66
TCTCCTACCGGGACGTCAAC

<220>

<221> primer_bind

<222> (6874)..(6964)

<223> Primer DgatrevRT66
GAGATCGCGGTAGGTCAGGTT
reverse primer

<220>

<221> primer_bind

<222> (6711)..(6972)

<223> Primer DgatforRTless66, GCTGCTTTGGCAGATCTCTACTACTT
This primer was designed to selectively bind and amplify the cDNA
splice variant. The corresponding binding site in this genomic s
equence comprises bases 6711 to 6715, 6815 to 6823 and 6960 to 69
72.

<220>

<221> primer_bind

<222> (7022)..(7038)

<223> Primer DgatrevRTless66
AAGCGCTTTCGGATGCG
reverse primer

<221> primer_bind

<222> (6857)..(6870)

<223> Probe Dgatwith66 (FAM)
CCGTGAGCTACCC

<220>

<221> primer_bind

<222> (6976)..(6990)

<223> Probe Dgatless66 (VIC)
CTTCGCCCCCACCCT

```
<400> 1
atg ggc gac cgc ggc ggc gcg ggc ggc tcc cgg cgc cgg agg acg ggg      48
Met Gly Asp Arg Gly Gly Ala Gly Gly Ser Arg Arg Arg Thr Gly
1               5                   10                  15 tcg cgg cct tcg atc cag ggc ggc agt ggg ccc gcg gca gcg gaa gag      96
Ser Arg Pro Ser Ile Gln Gly Gly Ser Gly Pro Ala Ala Ala Glu Glu
                20                  25                  30 gag gtg cgg gat gtg ggc gcc gga ggg gac gcg ccg gtc cgg gac aca     144
Glu Val Arg Asp Val Gly Ala Gly Gly Asp Ala Pro Val Arg Asp Thr
            35                  40                  45 gac aag gac gga gac gta gac gtg ggc agc ggc cac tgg gac ctg ag      191
Asp Lys Asp Gly Asp Val Asp Val Gly Ser Gly His Trp Asp Leu Arg
        50                  55                  60 gtagcggtgc gcgtgacccc taacctttga ccoctgatac ggggcccctg cgacccaacc   251
tggtggccca ggcctgtcgg cggcagctcg ggctcgagtc cgagagtctg gcgcctggac   311
cttggtgcac agctgtgccc ctcgggcctc cacggggaaa cttagcggga ggttggggc    371 ggagggtctc ctgcccggaa cacccaggta cggggccga ggggagggca gcggctcaac    431
ttctagacgc cctccctctg ccttcctttg gtgggttctg aagctttccc agggtgagcc   491
cactacgcac agtgtcctct acctggaagg agatacaggg gtccttcctg agggctatga   551
ggggtgcctt gtgggttgat aaagctcccg ggggaggagg gtggaccggc ggagaacaga   611
ggcaggggca gtgctagggg atttctcatc cctcgcagac cctccagaga atggtcttca   671
caaaggtccc tcatccgtca cccggcgatt gactggccta ggatcctgct tattaccagc   731
acaaatggct gctctagggt caaagtgggt cctgtaatgg gaccctcacc cctggttggg   791
```

FIGURE 2b continued

```
gtacagggga ggagttggaa gtgcgcacac ccacaggtgg gcgccctgct tagctgaagg    851
actgatggga aggagttggg ggagcaagct gcggctgaaa gggaggatct gacccacgtg    911
ggcatcagct aagtcctgct ggctgcctcc aggcgttccc tttgccatcc tccacgcccc    971
tcccccgggg cctgaccttc atcctggtca agggctctca ggggctctgg ttttgggatc   1031
agctccagag ctagaggtta tcaaggagga agtgggcaac aggtcagtca gcaaggattt   1091
gctatcttca ctgggtgctg tggggagggg agggacaagg gcagttgggg tgcaggcact   1151
gtccctgccc ttgggggggca cacagttcac ctgagagata agatagccgc agccctgaag   1211
agtgagagca aggtcaggc acagagttca ggatgacacc aggggagggt ggctctgtga   1271
ggggcactgg cttcctacag gccccaggtg gtcctgaggg ggcggctgca aaggccagga   1331
ggcccacagg cccctctgcc cactcctggg gaactggatt tggggtcact ttgtatgagg   1391
tgggggcggg taccagcttt gggccaagct gtcaccctgg atgggccatc acttgcctgc   1451
tctgtatagg ccagatggcc agaagctgct cctgtcctgt tgatggccca tcctcgaggt   1511
ctggaccctc gggaagagga gcagttggtg gcagggatgg gccaccggag accctcctga   1571
cctccaggac acgcagctgt gtgtgcctgt ccccaagcca catgccacat ggctaggggc   1631
ctcctgggc agggctgggc attggtctgg ctactcttgg tatcgcctat ggcttccctg   1691
cctcccagtc atcatcctcc cacctctgcc tccctgcctg ttcctctctt tctcctcagg   1751
cccttccgga catttcctgc tcacctaggt ctgggcaggc ggggtcaggt gccgggtgtg   1811
agctcactcc ttccggcagc aaggtgtagc tatgtgccgg aaggaaggcc gctgctgttg   1871
cctcgcctct gagtgcatcc cttccaggtc ctccacactc ccctgtgccc cgacacctgg   1931
tgcgtccttc agccattggt tcatgtgtcc tccaggcaca gctttctagt ccagagcctc   1991
taggctgggt gcaggaagtg ctgaggaagt ggcagccggg aggcgagctg gcaccctgtc   2051
cctccttgtt ctgtccgtcc ctgcccctgg accgtatggc cccgcatgtg tgatccccac   2111
ttggggctgt gcctctggc aagttgggaa gcttggtgag cctcattttc atgtgcccgc   2171
ctcccagtac tgatgtgcag gttgaatgag gtgccaactg taatgagttg gaatggccct   2231
gctggctggg tgggactggg gagcaggtgg gggccgctgg ggggcacaga ggcacaccca   2291
gtgcctcagt cagggagagg gtgacagaga agctctgggt gaggccccac ctccactctg   2351
gccatggctg ctgcccttg gtccactgca gtgaactgtg ccatggggct ggacctctgt   2411
gggggattggt gggcagtggg ctttcttccc gcttggggcc tctgacctct gggggcaggg   2471
cgctgcccgg gtgggacagt cggaaggctg gtagagggac ctgagggtc tgtgtggtgg   2531
ctgggggcag gcctcaggaa tttgacagca gggatctgga aaagctttaa taacattatt   2591
```

FIGURE 2b continued

```
tgttgtcagg attgggaaat gctccoctcc ccctccccc tctttcatct tagagactgc    2651
tgcacatctg gtcagtgtgg tcttcttggt ggcccccaag gtggcagggg tcacactgtt   2711
atgaaaccgt cccctgggta tgtggtgcag acatgcacat gcagatggtg attggcaggt   2771
tgtagcatga ggtggctttg gacggttcc  agtgacagtg agtgggctgg atctgggggg   2831
ttctgggcag gtccatcaag cggataccc  cacagactgt cctcttggga tagttgggcc   2891
tgggagccct gcttgccttg ccaaaaggca ggcgcagagt catgaagaag agggcttggg   2951
ggctcagagc cccactgtgt gtgcagccca gggtggacct ggaggaggtg cgtgggcagg   3011
ctgggccggc cggggcgggg ggtgggggg  cctggtgtga aagggaccca gggccagact   3071
gtcagcgctg cctggctgag gatgctggca ccctgtcctc cccagccgtc tgtctcctgg   3131
gtgcagccat ctgagtgctg accccagccg ccctggagg  ctggctgttc tcctgtgccc   3191
tattgctggg gacatgtgtc cacaggaggg aaaggaagc  cccggcctct ccccttacaa   3251
aactggaggc cttgctcaat gccctggatg gcctcctggt ggcagggtgg ttggtgggag   3311
gtggggctgc tgcttagaac ccgccagcgg gcctgggcct gggctgagct gcacccctcc   3371
acctctgcct ccagctgagg gttggcttcc atctccacca ggcccagcac tgggcacagg   3431
gctctcagag gcaggctctg aaagtcccct gctggcttct gcagtggact ccaggcgccg   3491
agccccagg  gggctcgcat tgcgctcacc ctgcgaagcc acgtgaaggc tgggtcctcc   3551
cctccggaag ggccaaatgc agggcatggg tggtttgaat ggtggcccct gggctccccg   3611
gagggaccag ctgctgtgag ggccgccccc tccccacttc cgtcttgcat caccagctcc   3671
tgtggcactc cccacgcccc gtcccccagt gggagcggca ggcccccggt ggctctgccc   3731
gcggaggggg atgtgtgggc ggcggggtgg ccttgctgcc agatgctctg ccccgagtgt   3791
ccgtctccgc tctccag g tgt cac cgc ctg cag gat tcc ctg ttc agt tct    3842
                    Cys His Arg Leu Gln Asp Ser Leu Phe Ser Ser
                     65              70                  75
gac agt ggc ttc agc aac tac cgt ggc atc ctg aat tgg tgt gtg gtg     3890
Asp Ser Gly Phe Ser Asn Tyr Arg Gly Ile Leu Asn Trp Cys Val Val
         80                  85                  90
atg ctg gtacgtagag tgacaccttg gagcaagggt cctgacggcc gggggggccat     3946
Met Leu gggctcttct ccaggggtag gtgtctgtac ttgtgtagct gtggtgaatg gagctctgtg   4006
ctggcggtgg gggtccctgg agcagccgta ccctgggacc ctaccgggag catgctcatg   4066
ccgtccctgc tgaatcccag gagatgcctg cagagggcag cctgggagcc tctgagctgg   4126
ggtctgcgcc ccagggggca ctggagtctc cccagggggc gagagagagt aggcagggat   4186
```

FIGURE 2b continued

```
ggtctggtgg ccctgggtgg gggatggctg ctccgtgggc ccaggccctc cctggcagca    4246
caggtgagtg gtcttggggg tccacgtaga acttcctctt ctgttccaaa ttgccctcat    4306
gggtgcggca tgcctgggtg aacctggggg agcagggtga ggacatgctt ctcagcccag    4366
cccacagctc caggccacac tctgcaggac tctggcccct ccctcagccc tggagggagc    4426
aggactggag tcctgtgtcc gccttgctct gacctggccg aggccactgc tgtggggccc    4486
cagcaggcct gcccagcaga aggtggagtg cagggacccc aggggcagcc ttcagggtgg    4546
ggcagggtga ggcccgactg ggcccagccc caccgctcag tgctgatgtg gcgcgaggcc    4606
ttcgcccctc cagctgacgt gtctgcctgc cctgggtgtg gctccagagg ctgcctgtgt    4666
accagggggcc cccacgcttc tgtttgtggt tctgggcagt cccctgggga gcggtggggg    4726
ctgtgtgcca gtccagaccc agtagtccac gcgtcctggt ctctggaggc cgtggctggt    4786
ccaggactgt ggcaaggtgg tcgtgcaggg caggccctca gcagcctgtc tgttctcctg    4846
cagcccccag cctcctggcc ctttggtgca cccacaaagc tccccctcc ccaggagct     4906
ggggccgcct gctgcgtcct ctcggcagcc tgggcttcca ggtggctggg cctcttagca    4966
gctccaactc ttgcctgtgg tgggctctca ggacaggcaa ctgccagtcg gcagacattg    5026
caggaccacg tgtgtcctgg taagctggct ggttaggtgt ttagctgggg gatggtgtgg    5086
caggtggccc ctgcatctct gagcctgtca cctcctcggg aagccttctg ggtgggggac    5146
tccacccatg tcgcctggag aagcatcact tttccacaga gccttctgca accccgtgg    5206
ggcctgagcc tggggtgggg gaggtggtgg cccctgctcc tgcagaggcc agccaggcat    5266
ctggccccag gccactggca agagctcgtt gtgttggggg atctgtcctt tgctgctgct    5326
gcaggagcgg ccgaggcagg cgggggcgtg agtagggggtg gagacccagg cccagcttcc    5386
ccagcccctc aggaccggcc tgctctttcc caccacccca ccaagtgcgt gggcacaccc    5446
cgcctgtgag gatgggcccg gttggcaggg cggagccctg ggagggtggc agtgcgccgg    5506
gcaggcttgg acttcactgg ggcttggggt tgtcgctgtg gccaggggcg ctgacccgct    5566
tggtgggacg gacggccgct gggcagcagg tttcttctgc cacggtggca caggcacctg    5626
gggttgtggt tggctccagg cgggcggggg ctgcgtgccc ctgcgcaggc acataggccg    5686
tgggtgggga gtctcagagc ttggcgtgag gtcccacagg gctgggcctg caggatggag    5746
gccactgtcc tgagctgcag gtgctggcag gagctggggt gggcgttctg ggccgtggc    5806
tgacagcgtt atgtccctct ctctctatcg cag atc tta agc aac gca cgg tta    5860
                                    Ile Leu Ser Asn Ala Arg Leu
                                     95                      100
ttt cta gag aac ctc atc aa  gtgagtgggc ccggcctgc ccagcccct            5910
Phe Leu Glu Asn Leu Ile Lys
105
```

FIGURE 2b continued

```
gccacctcac ccctcgccta cacagaccct cacccacctg cgtctgcag g tat ggc         5966
                                                         Tyr Gly atc ctg gtg gac ccc atc cag gtg gtg tct ctg ttc ctg aag gac ccc        6014
Ile Leu Val Asp Pro Ile Gln Val Val Ser Leu Phe Leu Lys Asp Pro
110             115             120             125 tac agc tgg cca gct ctg tgc ctg gtc att g gtgagctggg tgcccaggag        6065
Tyr Ser Trp Pro Ala Leu Cys Leu Val Ile
                130             135 gcctcaggcc ggcggtgggt gggacagggc tgatctgggc ctgaacctgc cctgggttgc      6125
ttctgtcctc ag tg  gcc aat atc ttt gcc gtg gct gcg ttc cag gtg gag     6175
                  Val Ala Asn Ile Phe Ala Val Ala Ala Phe Gln Val Glu
                              140                 145 aag cgc ctg gcc gtg gtaagcagtg ccctcacgcc ctcccctgac ttgcctcaag       6230
Lys Arg Leu Ala Val
            150 gtccttacca gtcgggctta gggcgggcca ccagctggtc ccactgtgct tcagggtttt     6290 gggcctttcg tggccttcct gagaggggct gcacctcagg cctggtggct cttcctcagg    6350 gaggtcctct gaccagggag gggggtccct ggctgacgct ctgctcccac cccag gga     6408
                                                               Gly gct ctg acg gag cag gcg ggg ctg ctg ctg cac ggg gtc aac ctg gcc       6456
Ala Leu Thr Glu Gln Ala Gly Leu Leu Leu His Gly Val Asn Leu Ala
155             160             165             170 acc att ctc tgc ttc cca gcg gcc gtg gcc ttt ctc ctg gag tct atc       6504
Thr Ile Leu Cys Phe Pro Ala Ala Val Ala Phe Leu Leu Glu Ser Ile
        175             180             185 act cca g gtgggcccca ccccgcccc cgccccgcc cacgctgtct cggccacggg       6561
Thr Pro cagcgcgggg ggcgtggcct gagcttgcct ctcccacag tg  ggc tcc gtg ctg        6614
                                              Val Gly Ser Val Leu
                                                      190 gcc ctg atg gtc tac acc atc ctc ttc ctc aag ctg ttc tcc tac cgg       6662
Ala Leu Met Val Tyr Thr Ile Leu Phe Leu Lys Leu Phe Ser Tyr Arg
        195             200             205 gac gtc aac ctc tgg tgc cga gag cgc agg gct ggg gcc aag gcc aag       6710
Asp Val Asn Leu Trp Cys Arg Glu Arg Arg Ala Gly Ala Lys Ala Lys
210             215             220             225 gct g gtgagggctg cctcgggctg gggccactgg gctgccactt gcctcgggac         6764
Ala cggcagggc tcggctcacc cccgaccgc ccctgccgc ttgctcgtag ct  ttg          6819
                                                         Ala Leu
```

FIGURE 2b continued

```
gca ggt aag aag gcc aac ggg gga gct gcc cag cgc acc gtg agc tac         6867
Ala Gly Lys Lys Ala Asn Gly Gly Ala Ala Gln Arg Thr Val Ser Tyr
    230             235             240 ccc gac aac ctg acc tac cgc g gtgaggatcc tgccgggggc tgggggact            6919
Pro Asp Asn Leu Thr Tyr Arg
245                 250 gcccggcggc ctggcctgct agccccgccc tcccttccag at  ctc tac tac ttc          6973
                                               Asp Leu Tyr Tyr Phe
                                                           255 ctc ttc gcc ccc acc ctg tgc tac gag ctc aac ttc ccc cgc tcc ccc          7021
Leu Phe Ala Pro Thr Leu Cys Tyr Glu Leu Asn Phe Pro Arg Ser Pro
            260             265             270 cgc atc cga aag cgc ttc ctg ctg cgg cga ctc ctg gag atg                  7063
Arg Ile Arg Lys Arg Phe Leu Leu Arg Arg Leu Leu Glu Met
    275             280             285 gtgaggcggg gcctcgcggg ccagggtggg cgggcctgcc ggcacccggc accggggctc        7123
agctcactgt ccgcttgctt ccttccccag ctg ttc ctc acc cag ctc cag gtg         7177
                                 Leu Phe Leu Thr Gln Leu Gln Val
                                                 290 ggg ctg atc cag cag gtacgtgccc gggggggggg gggggggggg gggggggact          7232
Gly Leu Ile Gln Gln
295 ctggggccgt tggggagctg actctgcgct ttttgcag tgg atg gtc ccg gcc atc        7288
                                          Trp Met Val Pro Ala Ile
                                                  300         305 cag aac tcc atg aag ccc ttc aag gtgagcaggc aggcctggca gggtgggttc         7342
Gln Asn Ser Met Lys Pro Phe Lys
            310 cggggtcagg gctgagggag ccagctgtgc cctgtgccca cag gac atg gac tac          7397
                                                 Asp Met Asp Tyr
                                                         315 tcc cgc atc gtg gag cgc ctc ctg aag ctg gcg gtgagtgacc tgctgggtgg        7450
Ser Arg Ile Val Glu Arg Leu Leu Lys Leu Ala
        320             325 ggacgcgtgg gggcgggtgg ggctgttctg gcacctggca cccactcccc acag gtc          7507
                                                              Val ccc aac cac ctc atc tgg ctc atc ttc ttc tac tgg ctc ttc cac tcc          7555
Pro Asn His Leu Ile Trp Leu Ile Phe Phe Tyr Trp Leu Phe His Ser
330             335             340             345 tgc ctg aac gcc gtg gct gag ctc atg cag ttt gga gac cgc gag ttc          7603
Cys Leu Asn Ala Val Ala Glu Leu Met Gln Phe Gly Asp Arg Glu Phe
            350             355             360
```

FIGURE 2b continued

```
    tac cgg gac tgg tg gtgggtggcc ttgccggggc ggggggtggtg ggggccccg        7657
    Tyr Arg Asp Trp Trp
              365 ctggggctgg ggccggagcc cctgcccact ctgccccgcc cccgcag g aac tcc gag        7714
                                                      Asn Ser Glu tcc atc acc tac ttc tgg cag aac tgg aac atc cct gtt cac aag tgg         7762
Ser Ile Thr Tyr Phe Trp Gln Asn Trp Asn Ile Pro Val His Lys Trp
370             375             380             385 tgc atc ag gtgggtgtgc gcctgggggc ggggggttgg gggtgggac                    7810
Cys Ile Arg ggggtcgcgt ggcccgggcg cccagcccac tgccgcctcc cccgcag a cac ttc tac       7867
                                                    His Phe Tyr
                                                        390 aag ccc atg ctc cgg cgg ggc agc agc aag tgg gca gcc agg acg gca         7915
Lys Pro Met Leu Arg Arg Gly Ser Ser Lys Trp Ala Ala Arg Thr Ala
        395             400             405 gtg ttt ctg gcc tcc gcc ttc ttc cac gag gtcagtgcac tgagggcgcg           7965
Val Phe Leu Ala Ser Ala Phe Phe His Glu
            410             415 ccctgcccct ggtgggggtg ggggtggggg tgggggctcg ctgacgcccc tctcccctca       8025 g tac ctg gtg agc atc ccc ctg cgc atg ttc cgc ctc tgg gcc ttc acc      8074
  Tyr Leu Val Ser Ile Pro Leu Arg Met Phe Arg Leu Trp Ala Phe Thr
      420             425             430 ggc atg atg gcg cag gtgagcagcc ctggaccccc gctccgcccc gccccgcgag         8129
Gly Met Met Ala Gln
        435 cgcagaggct cactcccgtc ctgtgtcccc ag atc ccg ctg gcc tgg ata gtg         8182
                                   Ile Pro Leu Ala Trp Ile Val
                                       440             445 ggc cgc ttc ttc cgc ggc aac tac ggc aac gcg gcc gtg tgg ctg tca         8230
Gly Arg Phe Phe Arg Gly Asn Tyr Gly Asn Ala Ala Val Trp Leu Ser
            450             455             460 ctc atc atc ggg cag ccg gtg gcc gtc ctg atg tac gtc cac gac tac         8278
Leu Ile Ile Gly Gln Pro Val Ala Val Leu Met Tyr Val His Asp Tyr
        465             470             475 tac gtg ctc aac cgt gag gcg ccg gca gcc ggc acc tgagcgcctc              8324
Tyr Val Leu Asn Arg Glu Ala Pro Ala Ala Gly Thr
        480             485 caggctggcc ccctcgtggg tgttggactg ctttgccgcg ctgcctgcgg ctggactaga       8384
gcctgcccca acctgggcgc agcaggagga ggcctggctg gtggaagctg cctcctggcc      8444
tccaccaggc ctctgcctga agggcttcct cctgccaggg gagagcaggc ccgacgcagt      8504 tctggccccct gggaggtgcc catgctctgg aaaccctaca gatctcgccc aagggtctga    8564
```

FIGURE 2b continued

```
atgtgtcaat aaagtgctgt gcacagtgag ctccctcagc ctccagggca cagggctggc    8624
aggaggggc  ggccctccca cgtggggcca tgctgtggga aggaggcccc agcgcctgga    8684
gaggagctgg ggctgtggtg accctccctg cctcacaggg ctctgtggtc agacgtcttg    8744
ccctgcaagg tggagactcc atgctccaag gccccctgtg cctgaggtct gcacacaagt    8804
ggattcaact tgggtcaggc cagaggctaa ggtgtggaag aaggttgaga atcaggctga    8864
cttgaacggc agcaaagact ccaaggcaag gctgcagaag tctcaaaagc tatgcgcaca    8924
gtcccctgct ggggtgctca cctgggctgg gctctgggct gcttggacaa agcaggtggc    8984
ctggctcagc cctcaccgag ggccttcctt ggggcagag gttggcctga tgccaggggc     9044
tccccgtttt tccaggccct cagcaggtag ttgggtgtgg ccctcatgat accttggtcc    9104
cagagctccg ccactcaaaa agcttggcag tgaggcaagg gcaacccgg gctgttcccc     9164
cctctactgg ctctgccgcc tgggttggaa accctgaggc tgtgccaggc aggtgtaccc    9224
tgacagccag ccatggccca gtaagatggg tgcccgaggt ggtacctggg cagcggaccc    9284
agctgtgctg ccccgcccc aaccagaagc cgctctagcc catggtggtc gtctgggcga     9344
gacaggctgg ttggctaggc actgtttggt ctacagcagg tgtaggcagc gtctccctga    9404
cccctgcctt ctaggaagcc accacctgn gcctactca tcagcaagga cagcgagcag      9464
ggctgagctg ggggtgcgtg ggctgctacg gnccccgcac cttcatcaca tgcacctctg    9524
cacccctgc  tgcctgactc aagagtgggg gggggggtcc tgtgcttcct tcattccaga    9584
cccacggtgc tgacccagtg cacccacctg gtccgctagt gctgacctgg ccacagggct    9644
cctgtgggcc cacgctgatc ccgcctggt cccttcataa agaactcttg agcacatgca     9704
gcccagggga gccaggaggc tccagtgtgc tgtgtccatc tgcctccctt cagccccttc    9764
cgagacactg cgcatcatgc ccccctccac ccccacccac actggcagga ggaacacaca    9824
gggagaccac acacagagct cgttgtttat aaatctctgc ctggctcatc ggtctgtttg    9884
tccatgtata tatctgcata tctctatgga aggggaaagg gggactcgtg taaaaatcca    9944
aaatacaatt ctatgaacac ctgcatcctg gtcagtctga gtgtggccgt gaagcccagg   10004
tgagctgtgg ctcacagggc taggccctcg gtgctggccg ggggccactc cccaccccct   10064
ctcccccct  ccgccagcca ggggaccagg ctcctggaca ccaggcctgc caaggcctg    10124
ctctcctcct ggggcttcta cgagacagtg gggtccttgg ctttgggggg ttctgagccc   10184
gtcagcaggg agatggtggg gtcatctctt atatttcgtc tccctcggag aagtaggagc   10244
cctcccccag ctcgaagagc accggcaggt cgctgctccc cacgtccacg gagcccgggt   10304
ccaggagcag caggggctgg gcggtgtagt gcaccagctg cttccctagg ggtgcgactg   10364
```

FIGURE 2b continued

```
ggtcagggtg ccggtggggc cgggggggcgg ggtggggnnn nnnnnnnnnn nnncccccccc   10424
ccccggcccc agccaccccg cctacgcacg ctggccaggc tgctgtccag gtcgggcagg    10484
ctcatgtcgg gcaccgtaac cgagggggctg aacagctgca gggaagaggg gcgggtcaga   10544
ctgccctgga agcggggcgg gctgggcgcg gggcgggcag ggttagactc acatccagca    10604
gggtgctggt gtccacgctg aagccatggc ttgtcagcat ggtctgcagg ttgtccaggt    10664
tggagtccat ggcgtccaag tggtcgctga gctcggtcct ggccagagga aggggagcag    10724
gtgacgtggc atccaggcac ccccaggtgc agtcctgccg gcccttaagc ccagctgcca    10784
gcctgccctg cgcaggctca cgggaggccc tgaggtgggg ccctgggcct gggacacttg    10844
gccaccggtg gtggctcagg ctccctcatc accgtgaggc cccgtaaggc agcacgtcag    10904
gctgggccgg ctaagacatc aggggggctga gttcagggct cagaagggcc cggggcccca   10964
gcttctcagg ttcagcaacg cctgcccttc acactggagg acagcaggag ggtggagctg    11024
tgctcggcca ggctgggcca gcctacccca gcatgcgcca ggatagatta ggcctgcccc    11084
ctcgaggagg ccaggcagta cctcggggtg ctgcctcagg ccccagaggt gggtggggag    11144
cctgttcaca ggctgggcag gggtctgctc agaggctggg gaggggccca agctctggcg    11204
gagccctcct ccctccccag tgggacagcg ctaaccctgg ctggactcgg ccatgcagag    11264
aggaggaggg gcaggggaag aggcgggcga ccccagacat ctttggagtg cgagccaaac    11324
tgcaagatag aaagacaaga gcccccctct gcgggtgggg cccagcgagt ccaagccccc    11384
cacdccgttc acccacctct ggggtggtag gacagacaga ccaggcggcc cggggagggc    11444
ggctcagggg gcagggggtgc ccgccacgtg cctggttccc acggtgcagg ggctgcggga   11504
ccccctggct ggcatgtctc cctccccagc tccatgctct gggccaggtc ggccagtttc    11564
ccccagcaaa tcccatgccg agggcctgag ggcatgcgt gtccagcccg gcactgtcct     11624
tgtcggaggc ccctgcgctt ccagagaccg aagggcgcct ggaaggcact cacttgtcta    11684
ggcaggcgac gctgaggcac ttctcgggag ccgaggcggg gagggtcgac ggatagcggc    11744
cccgagtgat ccgatagaag cttcgta                                        11771
```

FIGURE 2b continued

<221> VARIANT

<222> (232)..(232)

<223> an amino acid substitution (K -> A) caused by a polymorphism at b
ases 7224-7225 of the genomic sequence (measured from the adenine
residue of the translation start codon). Lysine (K) corresponds
to the Q allele, alanine (A) corresponds to the q allele.

<400> 5

```
Met Gly Asp Arg Gly Gly Ala Gly Gly Ser Arg Arg Arg Thr Gly
1               5                   10                  15

Ser Arg Pro Ser Ile Gln Gly Gly Ser Gly Pro Ala Ala Ala Glu Glu
            20                  25                  30

Glu Val Arg Asp Val Gly Ala Gly Gly Asp Ala Pro Val Arg Asp Thr
            35                  40                  45

Asp Lys Asp Gly Asp Val Asp Val Gly Ser Gly His Trp Asp Leu Arg
    50                  55                  60

Cys His Arg Leu Gln Asp Ser Leu Phe Ser Ser Asp Ser Gly Phe Ser
65                  70                  75                  80

Asn Tyr Arg Gly Ile Leu Asn Trp Cys Val Val Met Leu Ile Leu Ser
                85                  90                  95

Asn Ala Arg Leu Phe Leu Glu Asn Leu Ile Lys Tyr Gly Ile Leu Val
            100                 105                 110

Asp Pro Ile Gln Val Val Ser Leu Phe Leu Lys Asp Pro Tyr Ser Trp
            115                 120                 125

Pro Ala Leu Cys Leu Val Ile Val Ala Asn Ile Phe Ala Val Ala Ala
            130                 135                 140

Phe Gln Val Glu Lys Arg Leu Ala Val Gly Ala Leu Thr Glu Gln Ala
145                 150                 155                 160

Gly Leu Leu Leu His Gly Val Asn Leu Ala Thr Ile Leu Cys Phe Pro
                165                 170                 175
```

FIGURE 4a

```
Ala Ala Val Ala Phe Leu Leu Glu Ser Ile Thr Pro Val Gly Ser Val
            180                 185                 190

Leu Ala Leu Met Val Tyr Thr Ile Leu Phe Leu Lys Leu Phe Ser Tyr
        195                 200                 205

Arg Asp Val Asn Leu Trp Cys Arg Glu Arg Ala Gly Ala Lys Ala
    210                 215                 220

Lys Ala Ala Leu Ala Gly Lys Lys Ala Asn Gly Gly Ala Ala Gln Arg
225                 230                 235                 240

Thr Val Ser Tyr Pro Asp Asn Leu Thr Tyr Arg Asp Leu Tyr Tyr Phe
                245                 250                 255

Leu Phe Ala Pro Thr Leu Cys Tyr Glu Leu Asn Phe Pro Arg Ser Pro
            260                 265                 270

Arg Ile Arg Lys Arg Phe Leu Leu Arg Arg Leu Leu Glu Met Leu Phe
        275                 280                 285

Leu Thr Gln Leu Gln Val Gly Leu Ile Gln Gln Trp Met Val Pro Ala
    290                 295                 300

Ile Gln Asn Ser Met Lys Pro Phe Lys Asp Met Asp Tyr Ser Arg Ile
305                 310                 315                 320

Val Glu Arg Leu Leu Lys Leu Ala Val Pro Asn His Leu Ile Trp Leu
                325                 330                 335

Ile Phe Phe Tyr Trp Leu Phe His Ser Cys Leu Asn Ala Val Ala Glu
            340                 345                 350

Leu Met Gln Phe Gly Asp Arg Glu Phe Tyr Arg Asp Trp Trp Asn Ser
        355                 360                 365

Glu Ser Ile Thr Tyr Phe Trp Gln Asn Trp Asn Ile Pro Val His Lys
    370                 375                 380

Trp Cys Ile Arg His Phe Tyr Lys Pro Met Leu Arg Arg Gly Ser Ser
385                 390                 395                 400

Lys Trp Ala Ala Arg Thr Ala Val Phe Leu Ala Ser Ala Phe Phe His
                405                 410                 415
```

FIGURE 4a continued

```
Glu Tyr Leu Val Ser Ile Pro Leu Arg Met Phe Arg Leu Trp Ala Phe
            420                 425                 430

Thr Gly Met Met Ala Gln Ile Pro Leu Ala Trp Ile Val Gly Arg Phe
            435                 440                 445

Phe Arg Gly Asn Tyr Gly Asn Ala Ala Val Trp Leu Ser Leu Ile Ile
    450                 455                 460

Gly Gln Pro Val Ala Val Leu Met Tyr Val His Asp Tyr Tyr Val Leu
465                 470                 475                 480

Asn Arg Glu Ala Pro Ala Ala Gly Thr
                485
```

Met Gly Asp Arg Gly Gly Ala Gly Gly Ser Arg Arg Arg Thr Gly
1               5                   10                  15

Ser Arg Pro Ser Ile Gln Gly Gly Ser Gly Pro Ala Ala Ala Glu Glu
            20                  25                  30

Glu Val Arg Asp Val Gly Ala Gly Gly Asp Ala Pro Val Arg Asp Thr
            35                  40                  45

Asp Lys Asp Gly Asp Val Asp Val Gly Ser Gly His Trp Asp Leu Arg
        50                  55                  60

Cys His Arg Leu Gln Asp Ser Leu Phe Ser Ser Asp Ser Gly Phe Ser
65                  70                  75                  80

Asn Tyr Arg Gly Ile Leu Asn Trp Cys Val Met Leu Ile Leu Ser
                85                  90                  95

Asn Ala Arg Leu Phe Leu Glu Asn Leu Ile Lys Tyr Gly Ile Leu Val
            100                 105                 110

Asp Pro Ile Gln Val Val Ser Leu Phe Leu Lys Asp Pro Tyr Ser Trp
            115                 120                 125

Pro Ala Leu Cys Leu Val Ile Val Ala Asn Ile Phe Ala Val Ala Ala
            130                 135                 140

Phe Gln Val Glu Lys Arg Leu Ala Val Gly Ala Leu Thr Glu Gln Ala
145                 150                 155                 160

Gly Leu Leu Leu His Gly Val Asn Leu Ala Thr Ile Leu Cys Phe Pro
                165                 170                 175

Ala Ala Val Ala Phe Leu Leu Glu Ser Ile Thr Pro Val Gly Ser Val
            180                 185                 190

Leu Ala Leu Met Val Tyr Thr Ile Leu Phe Leu Lys Leu Phe Ser Tyr
            195                 200                 205

Arg Asp Val Asn Leu Trp Cys Arg Glu Arg Arg Ala Gly Ala Lys Ala
            210                 215                 220

Lys Ala Ala Leu Ala Asp Leu Tyr Tyr Phe Leu Phe Ala Pro Thr Leu
225                 230                 235                 240

FIGURE 4b

```
Cys Tyr Glu Leu Asn Phe Pro Arg Ser Pro Arg Ile Arg Lys Arg Phe
                245             250             255

Leu Leu Arg Arg Leu Leu Glu Met Leu Phe Leu Thr Gln Leu Gln Val
            260             265             270

Gly Leu Ile Gln Gln Trp Met Val Pro Ala Ile Gln Asn Ser Met Lys
        275             280             285

Pro Phe Lys Asp Met Asp Tyr Ser Arg Ile Val Glu Arg Leu Leu Lys
    290             295             300

Leu Ala Val Pro Asn His Leu Ile Trp Leu Ile Phe Phe Tyr Trp Leu
305             310             315                         320

Phe His Ser Cys Leu Asn Ala Val Ala Glu Leu Met Gln Phe Gly Asp
                325             330             335

Arg Glu Phe Tyr Arg Asp Trp Trp Asn Ser Glu Ser Ile Thr Tyr Phe
            340             345             350

Trp Gln Asn Trp Asn Ile Pro Val His Lys Trp Cys Ile Arg His Phe
            355             360             365

Tyr Lys Pro Met Leu Arg Arg Gly Ser Ser Lys Trp Ala Ala Arg Thr
        370             375             380

Ala Val Phe Leu Ala Ser Ala Phe Phe His Glu Tyr Leu Val Ser Ile
385             390             395                         400

Pro Leu Arg Met Phe Arg Leu Trp Ala Phe Thr Gly Met Met Ala Gln
                405             410             415

Ile Pro Leu Ala Trp Ile Val Gly Arg Phe Phe Arg Gly Asn Tyr Gly
            420             425             430

Asn Ala Ala Val Trp Leu Ser Leu Ile Ile Gly Gln Pro Val Ala Val
            435             440             445

Leu Met Tyr Val His Asp Tyr Tyr Val Leu Asn Arg Glu Ala Pro Ala
        450             455             460

Ala Gly Thr
465
```

FIGURE 4b continued

```
                                    K232A
                                     ⇩
Bos taurus:                 LALMVYTILFLKLFSYRDVNLWCRERRAGAKAKAALAGKKANGGAAQRTVSYPDNLTYRDLYYFLFAPTLCY
Bison bison:                LALMVYTILFLKLFSYRDVNLWCRERRAGAKAKAALAGKKANGGAAQRTVSYPDNLTYRDLYYFLFAPTLCY
Ovis aries:                 LALMVYTILFLKLFSYRDVNLWCRERRAGAKAKAALAGKKANGGAAQRTVSYPDNLTYRDLYYFLFAPTLCY
Sus scrofa:                 LALMVYAILFLKLFSYRDVNLWCRERRATAKAKAASAGKKANGGAAQHSVSYPDNLTYRDLYYFLLAPTLCY
Homo sapiens:               LALMAHTILFLKLFSYRDVNSWC---RR---ARAKAASAGKKASSAAAPHTVSYPDNLTYRDLYYFLFAPTLCY
Cercopithecus aethiops:     LALMVHTILFLKLFSYRDVNLWC---RR---ARAKAASAGKRASSAAAPHTVSYPDNLTYRDLYYFLFAPTLCY
M. musculus domesticus:     FALASYSIMFLKLYSYRDVNLWCRQRR---VKAKAVSTGKKVSGAAAQQAVSYPDNLTYRDLYYFIFAPTLCY
Rattus norvegicus:          FALASYSIIFLKLSSYRDVNLWCRQRR---VKAKAVSAGKKVSGAAAQNTVSYPDNLTYRDLYYFIFAPTLCY
```

MARKER ASSISTED SELECTION OF BOVINE FOR IMPROVED MILK PRODUCTION USING DIACYLGLYCEROL ACYLTRANSFERASE GENE DGAT1

Reference to Related Applications

The present application is the U.S. national phase of International Application PCT/NZ/01/00245, filed Oct. 31, 2001, and claims priority under 35 U.S.C. §119 to New Zealand Patent Application No. 507888, filed Oct. 31, 2000 and New Zealand Patent Application No. 508662 filed Dec. 6, 2000.

FIELD OF THE INVENTION

This invention relates to an application of marker assisted selection of bovine for a quantitative trait loci (QTL) associated with milk production, particularly although by no means exclusively, by assaying for the presence of at least one allele which is associated with increased milk volume as well as improved milk composition. The present invention also relates to the gene associated with the QTL, various polymorphisms within the gene sequence, proteins encoded by these sequences as well as to the application of all of these in the farming industry.

BACKGROUND

The genetic basis of bovine milk production is of immense significance to the dairy industry. An ability to modulate milk volumes and content has the potential to alter farming practices and to produce products which are tailored to meet a range of requirements. In particular, a method of genetically evaluating bovine to select those which express desirable traits, such as increased milk production and improved milk composition, would be desirable.

To date, bovine genomics are poorly understood and little is known regarding the genes which are critical to milk production. While there have been reports of quantitative trait loci (QTLs) on bovine chromosome 14 postulated to be associated with milk production (Coppieters et al (1998)), the specific genes involved have not to date been identified.

Marker assisted selection, which provides the ability to follow a specific favourable genetic allele, involves the identification of a DNA molecular marker or markers that segregate with a gene or group of genes associated with a QTL. DNA markers have several advantages. They are relatively easy to measure and are unambiguous, and as DNA markers are co-dominant, heterozygous and homozygous animals can be distinctively identified. Once a marker system is established, selection decisions are able to be made very easily as DNA markers can be assayed at any time after a DNA containing sample has been collected from an individual infant or adult animal, or even earlier as it is possible to test embryos in vitro if such embryos are collected.

The applicants have now identified a gene responsible for the QTL effect on bovine chromosome 14 as well as a number of polymorphisms which are associated with distinct genetic merits of animals for milk composition and volume.

It is an object of the present invention to provide an application method for marker assisted selection of this bovine gene, and in particular, of the polymorphisms in the bovine gene which are associated with increased milk volume and altered milk composition; and/or to provide genetic markers for use in such a method; and/or to provide the nucleic acid and amino acid sequences of this gene and encoded polypeptide; and/or to provide animals selected using the method of the invention as well as milk produced by the selected animals; and/or to provide the public with a useful choice.

SUMMARY OF THE INVENTION

This invention relates to the discovery of the bovine Diacylglycerol-o-acyltransferase (DGAT1) gene and polymorphisms within the bovine DGAT1 gene which are associated with increased milk yield and altered milk composition.

More specifically, several polymorphisms- in the bovine DGAT1 gene have been identified distinguishing multiple DGAT1 alleles in different cattle breeds. These polymorphisms include: K232A (Bases 6829/30 AA-CG nucleic acid change and K-A amino acid change); Nt984+8(Base 7438 A-G nucleic acid change); Nt984+26(Base 7456 C-T nucleic acid change); Nt1470+85(Base 8402 C-T nucleic acid change); Nt191+435 (Base 626 T-G nucleic acid change); Nt191-3321 (Base 3512 T-G nucleic acid change); Nt279+144 (Base 4040 T-C nucleic acid change); Nt279+1067 (Base 4963 A-G nucleic acid change); Nt279+1107 (Base 5003 G-A nucleic acid change); Nt358 (Base 5997 C-T nucleic acid change); Nt754+3 (Base 6892 G-A nucleic acid change); Nt897+32 (Base 7224/5 GG-AC nucleic acid change); Nt1251+42 (Base 7987 G-A nucleic acid change) as summarised in Table 1. In particular, DGAT1 alleles characterized by the K232A mutation have been identified as being associated with an increased milk volume and altered milk composition in animals dependent upon whether they are homozygous with or without the mutation or heterozygous carrying one mutated allele. More specifically, the presence of the K232A mutation results in a decrease in milkfat percentage, milkfat yield, solid fat content and milk protein percentage, while increasing milk volume and milk protein yield.

The present invention thus relates to the use of the polymorphisms in a method of identification and selection of a bovine having at least one of said polymorphisms as well as to providing markers specific for such identification. Kits comprising said markers for use in marker selection also form part of the present invention as do animals so selected, the milk produced by such selected animals and products produced from such milk, particularly as such milk and milk products affect processing and/or health characteristics for consumers.

In particular, the present invention is directed to a method of genotyping cows or bulls for one or more of the polymorphisms disclosed herein, selected cows or bulls so genotyped and milk and semen from said selected cows and bulls respectively.

According to a further aspect the present invention is directed to the isolated DGAT1 nucleic acid and allelic nucleic acid molecules comprising polymorphisms as well as to the proteins encoded thereby and their polypeptide sequences. Antibodies raised against said proteins are also contemplated, as are vectors comprising the nucleic acid molecules, host cells comprising the vectors; and protein molecules expressed in said host cells; and the application of all of them in the farming industry.

In particular, such applications include methods for modulating milk production and/or composition in a lactating bovine by affecting DGAT1 activity, by reducing the activity of DGAT1 (e.g. by use of specific ribozymes, antisense sequences and/or antibodies, or by transgenic technology to produce a "knock out" bovine and/or bovine with introduced transgenes containing the DGAT1 gene and/or variations of this gene driven by various promoters).

BRIEF DESCRIPTION OF THE DRAWINGS

The invention will now be described with reference to the Figures of the accompanying drawings in which:

FIGS. 2a and 2b: Show the genomic sequence of the bovine DGAT1 gene. FIG. 2a is the 31 base pair sequence upstream but adjacent to the ATG or translation start site and is 5' UTR. FIG. 2b is the genomic sequence in the bovine DGAT1 gene from the ATG translation start site (base 1) through to genomic sequence flanking the gene at the 3' end. The significant features including intron/exon boundaries, polymorphic sites, polyadenylation signal, and alternate splicing site and some of the primer sequences used in the assays described herein, are indicated;

FIG. 4a: Shows the corresponding full length amino acid sequence for DGAT1 sequence of FIG. 2b including annotation of the amino acid substitution;

FIG. 4b: Shows the amino acid sequence predicted as a result of alternate splicing with exon VIII;

FIG. 5: Shows the multiple peptide alignment of a portion of the DGAT1 protein flanking the K232A substitution from *Bos taurus*, *Bison bison*, *Ovis aries*, *Sus scrofa*, *Homo sapiens*, *Cercopithecus aethiops*, *Mus musculus domesticus* and *Rattus noruegicus* showing the evolutionary conservation of the lysine mutated in the bovine K232A polymorphism;

DETAILED DESCRIPTION OF THE INVENTION

Figure 1:
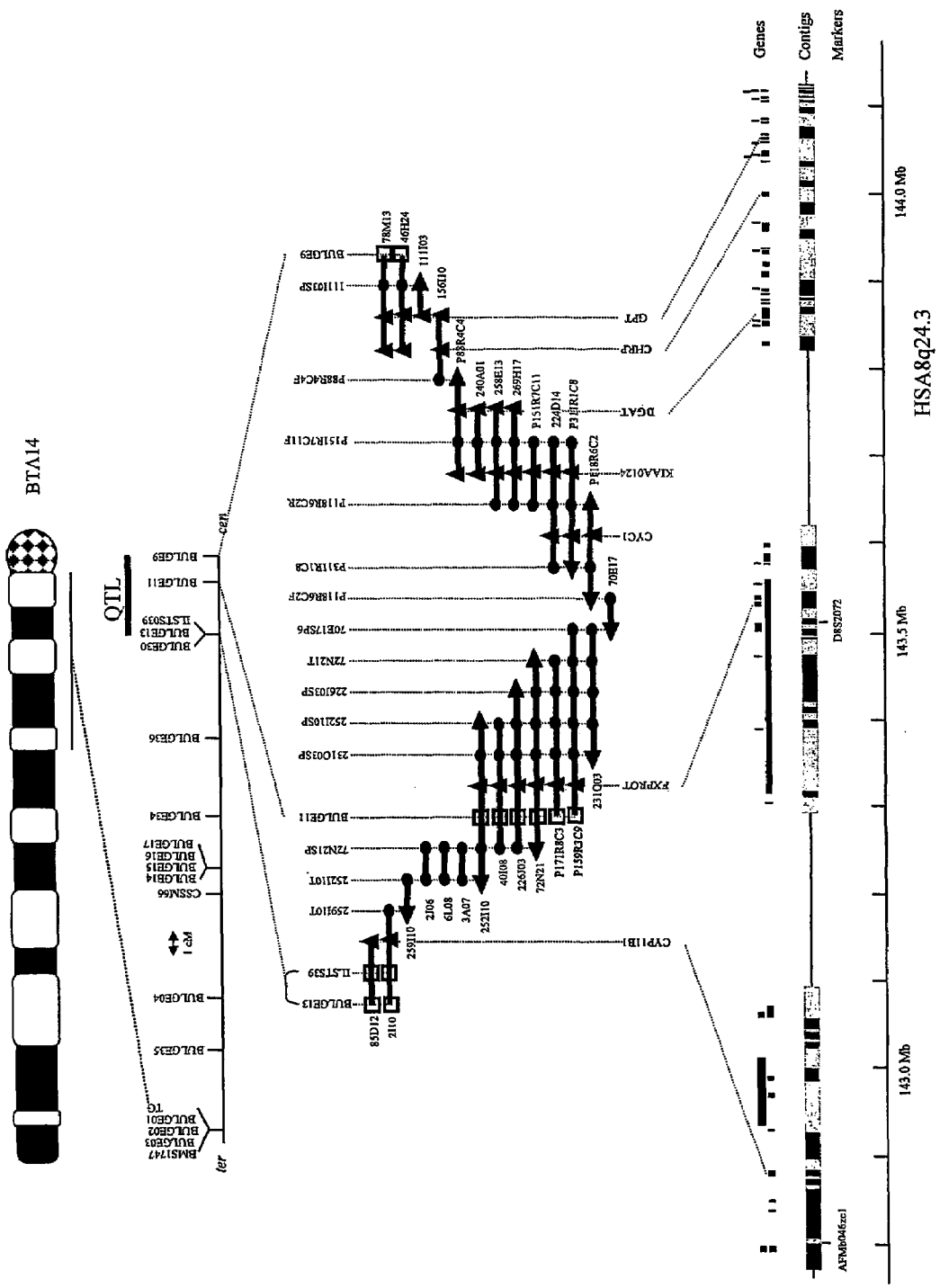
FIG. 1: shows a BAC contig spanning the BULGE12-BULGE 09 interval relative to a schematic diagram of bovine chromosome 14 and a schematic diagram showing the location of the genetic markers. The most likely position of the QTL is shown as a bar on the FISH-ancored linkage map proximal to BTA14q. The BACs composing the contigs spanning BULGE13-BULGE09 interval are shown as a series of horizontal lines. The symbols on each BAC indicate their individual STS content: solid boxes correspond to STS derived from BAC ends, open boxes to microsatellite markers, and solid triangles to gene-specific Comparative Anchored Tagged Sequences. The arrow heads mark the BACs from which the respective BAC end STS were derived. The length of the lines do not reflect the actual insert size of the corresponding BACs. The BAC contig was aligned with the orthologous human HSA8q24.3 genomic "golden path" sequence represented according to the Ensembl Human Genome Server individual sequence contigs are shown in alternating light and dark; a horizontal line indicates a gap in the sequence assembly; genetic markers are indicated under the contig map; the lines and boxes above the contig map represent "curated", "predicted known" or "predicted novel" genes.

It has been discovered for the first time that the DGAT1 gene in bovine is associated with the QTL on chromosome 14 which is linked with improved milk production traits. More particularly, a number of novel polymorphisms on the DGAT1 gene have been discovered. It is thought that one or more of these polymorphisms is responsible for these traits.

The method used for isolating genes which cause specific phenotypes is known as positional candidate cloning. It involves: (i) the chromosomal localisation of the gene which causes the specific phenotype using genetic markers in a linkage analysis; and (ii) the identification of the gene which causes the specific phenotype amongst the "candidate" genes known to be located in the corresponding region. Most of the time these candidate genes are selected from available mapping information in humans and mice.

The tools required to perform the initial localisation (step (i) above) are microsatellite marker maps, which are available for livestock species and are found in the public domain (Bishop et al., 1994; Barendse et al., 1994; Georges et al., 1995; and Kappes, 1997). The tools required for the positional candidate cloning, particularly the BAC libraries, (step (ii) above) are partially available from the public domain. Genomic libraries with large inserts constructed with Bacterial Artificial Chromosomes (BAC) are available in the public domain for most livestock species including cattle. For general principles of positional candidate cloning, see Collins, 1995 and Georges and Anderson, 1996.

Recently, a quantitative trait locus (QTL) with major effect on milk solids composition, located at the centromeric end of bovine chromosome 14, has been reported (Coppieters et al., (1998)). This QTL was shown to effect milk fat content and in particular to significantly affect protein %, volume, protein yield and fat yield of milk. The linkage study as well as subsequent marker assisted segregation analyses allowed for the identification of thirteen Holstein-Friesian sires predicted to be heterozygous "Qq" for the corresponding QTL (Coppieters et al., (1998); Riquet et al., (1999)).

Linkage disequilibrium methods were applied to refine the map position of the QTL to a ≈5 cM interval bounded by microsatellite markers BULGE09 and BULGE30.

A bovine DGAT1 nucleotide sequence was determined by the applicants and is shown in FIGS. 2a and 2b with the corresponding amino acid sequences (long and short forms) being shown in FIGS. 4a and 4b respectively. Table 1 sets out all the polymorphisms located to date with reference to the sequence in FIG. 2b. Some of the genetic polymorphisms identified in the bovine DGAT1 gene are reported in FIG. 3. The nucleic acid and protein sequences of the DGAT1 alleles including the K232A mutation are shown in FIGS. 2a and 2b (SEQ ID NOs: 3 and 1), annotated to show the alternatively spliced forms. The cDNA sequence is also set out in SEQ ID NO: 4.

The sequence information in the Figures gives rise to numerous, and separate, aspects of the invention.

In one aspect, the invention provides a method of determining genetic merit of a bovine with respect to milk composition and volume which comprises the step of determining the bovine DGAT1 genotyping state of said bovine. In particular, this method is useful for genotyping and selecting cows and bulls having the desired genotypic state so that milk and semen may be collected from said cows and bulls respectively. Such semen would be useful for breeding purposes to produce bovine having the desired genotypic and, as a result, phenotypic state. In addition, cows genotyped by the methods of the present invention are also useful for breeding purposes, particularly for breeding with the selected bulls and/or to be artificially inseminated with the semen from selected bulls. The embryos and offspring produced by such cows also form part of the present invention.

In one embodiment, the genotypic state is determined with respect to DNA obtained from said bovine.

Alternatively, said genotypic state is determined with reference to mRNA obtained from said bovine.

In yet a further embodiment, the genotypic state is determined with reference to the amino acid sequence of expressed bovine DGAT1 protein obtained from said bovine.

Conveniently, in said method, the genotypic state of DNA encoding bovine DGAT1 is determined, directly or indirectly.

Alternatively, in said method the genotypic state of at least one nucleotide difference from the nucleotide sequence encoding bovine DGAT1 is determined, directly or indirectly.

More specifically, in said method the genotypic state of bovine DGAT1 allele(s) characterised by one or more of the polymorphisms shown in Table 1 below, is determined, directly or indirectly.

TABLE 1

Table of polymorphisms in the bovine DGAT1 gene
Start codon (atg); the a residue is denoted as position 1

| Base number relative to exonic sequence[1] | Nucleotide distance from start | substitution | SEQ ID NO: | Intron/exon # |
|---|---|---|---|---|
| Nt 191 + 435 | 626 | T-G<br>CAGTGCTAGGGG<br>CAGTGCGAGGGG | <br>22<br>23 | Intron 1 |
| Nt 191 + 3321 | 3512 | T-G<br>GCATTGCGCT<br>GCATGGCGCT | <br>24<br>25 | Intron 1 |
| Nt 279 + 144 | 4040 | T-C<br>TACCCTGGGAC<br>TACCCCGGGAC | <br>26<br>27 | Intron 2 |
| Nt 279 + 1067 | 4963 | A-G<br>CTCTTAGCAGC<br>CTCTTGGCAGC | <br>28<br>29 | Intron 2 |
| Nt 279 + 1107 | 5003 | G-A<br>ACAGGCAACT<br>ACAGACAACT | <br>30<br>31 | Intron 2 |
| Nt 358 | 5997 | C-T<br>TGTCTCTGTTC<br>TGTCTTTGTTC | <br>32<br>33 | Exon IV |
| Nt 692 | 6829 | AA-GC<br>GGTAAGAAGGCCAA<br>(Q)<br>GGTAAGGCGGCCAA<br>(q) | <br>34<br><br>35<br> | K232A Exon VIII* |
| Nt 754 + 3 | 6892 | G-A<br>GCGGTGAGGAT<br>GCGGTAAGGAT | <br>36<br>37 | Intron VIII |
| Nt 897 + 32 | 7224 | GG-AC<br>GGGGGGGGGGGA<br>CTCT<br>GGGGGACGGGGA<br>CTCT | <br>38<br><br>39<br> | Intron X |
| Nt 984 + 8 | 7438 | A-G<br>GAGTGACCTGC<br>GAGTGGCCTGC | <br>40<br>41 | Intron XII* |
| Nt 984 + 26 | 7456 | C-T<br>GGACGCGTGGG<br>GGACGTGTGGG | <br>42<br>43 | Intron XII* |

TABLE 1-continued

Table of polymorphisms in the bovine DGAT1 gene
Start codon (atg); the a residue is denoted as position 1

| Base number relative to exonic sequence[1] | Nucleotide distance from start | substitution | SEQ ID NO: | Intron/exon # |
|---|---|---|---|---|
| Nt 1251 + 42 | 7987 | G-A<br>GGTGGGGGTGG<br>GGTGGAGGTGG | <br>44<br>45 | Intron XV |
| Nt 1470 + 85 | 8402 | C-T<br>CTGGGCGCAGC<br>CTGGGTGCAGC | <br>46<br>47 | 3' flanking region * |

The numbers given are far the actual nucleotide or in the case of two nucleotide substitutions to the first nucleotide in the variation (counting 5' to 3'
*More detail of these polymorphisms is given in FIG. 2b.
[1]e.g. Nt 191 represents nucletode number 191 from the start site of the coding sequence, + 435 represents number of nucleotides from and including base 192 in the genomic sequence (intron 1) to the polymorphic nucleotide
The polymorphic nucleotides are shaded Preferably, the invention is directed to a method of determining the genotypic state of bovine DGAT1 allele(s) by determining the presence of the K232A polymorphism, either directly or indirectly.

There are numerous art standard methods known for determining whether a particular DNA sequence is present in a sample. An example is the Polymerase Chain Reaction (PCR). A preferred aspect of the invention thus includes a step in which ascertaining whether a polymorphism(s) in the sequence of DGAT1 DNA is present, includes amplifying the DNA in the presence of primers based on the nucleotide sequence of the DGAT1 gene and flanking sequence, and/or in the presence of a primer containing at least a portion of a polymorphism as disclosed herein and which when present results in altered relative milk lipid and protein production, and milk volume.

A primer of the present invention, used in PCR for example, is a nucleic acid molecule sufficiently complementary to the sequence on which it is based and of sufficient length to selectively hybridise to the corresponding portion of a nucleic acid molecule intended to be amplified and to prime synthesis thereof under in vitro conditions commonly used in PCR. Likewise, a probe of the present invention, is a molecule, for example a nucleic acid molecule of sufficient length and sufficiently complementary to the nucleic acid molecule of interest, which selectively binds under high or low stringency conditions with the nucleic acid sequence of interest for detection thereof in the presence of nucleic acid molecules having differing sequences.

In another aspect, the invention provides a method for determining the genetic merit of bovine with respect to milk content and volume with reference to a sample of material containing mRNA obtained from the bovine. This method includes ascertaining whether a polymorphism(s) in the sequence of the mRNA encoding DGAT1 is present. The presence of such polymorphisms again indicates an association with altered relative milk lipid and protein production and milk volume.

Again, if an amplification method such as PCR is used in ascertaining whether a polymorphism(s) in the sequence of the mRNA encoding (DGAT1) is present, the method includes reverse transcribing the mRNA using a reverse transcriptase to generate a cDNA and then amplifying the cDNA in the presence of a pair of primers complementary to a nucleotide sequence encoding a protein having biological activity of wild type DGAT1.

In a further aspect, the invention includes the use of a probe in the methods of genotyping according to the invention wherein the probe is selected from any 5 or more contiguous nucleotides of the DGAT1 sequence as shown in FIG. 2b, which is therefore sufficiently complementary with a nucleic acid sequence encoding such bovine DGAT1, or its complement, so as to bind thereto under stringent conditions. Diagnostic kits containing such a probe are also included. Such probes may be selected from ForAA (FAM): CGTTGGCCT-TCTTA or DgatADGC (VIC): TTGGCCGCCTTACC. (SEQ ID NOs: 20 and 21 respectively.)

The invention further includes isolated nucleic acid molecules encoding the DGAT1 variant proteins i.e. those proteins encoded by SEQ ID NOs: 1 and 4 (FIG. 2b), comprising one or more polymorphisms of SEQ ID NOs: 7 to 19 (Table 1), or a fragment or variant thereof. Particularly, the invention includes an isolated nucleic acid molecule comprising a DNA molecule having in whole or in part the nucleotide sequence identified in FIG. 2b or which varies from the sequence due to the degeneracy of the genetic code, or a nucleic acid strand capable of hybridising with said nucleic acid molecule under stringent hybridisation conditions.

The invention includes isolated mRNA transcribed from DNA having a sequence which corresponds to a nucleic acid molecule of the invention.

The invention includes isolated DNA in a recombinant cloning vector and a prokaryotic or eukaryotic cell containing and expressing heterologous DNA of the invention.

The invention includes a transfected coil line which expresses a protein encoded by the nucleic acid molecules of the invention.

The invention also includes a primer composition useful for detection of the presence of one or more polymorphisms associated with improved milk production traits in bovine DNA encoding DGAT1 and/or the presence of DNA encoding a variant protein. In one form, the composition can include a nucleic acid primer substantially complementary to a nucleic acid sequence encoding DGAT1. The nucleic acid sequence can in whole or in part be that identified in FIG. 2b. Diagnostic kits including such a composition are also included.

The invention further provides a diagnostic kit useful in detecting DNA encoding a variant DGAT1 protein in bovine which includes first and second primers for amplifying the DNA, the primers being complementary to nucleotide sequences of the DNA upstream and downstream, respectively, of a polymorphism in the portion of the DNA encoding DGAT1 which results in altered relative milk lipid, solid fat content and protein production and milk volume, wherein at least one of the nucleotide sequences is elected to be from a non-coding region of the DGAT1 gene. The kit can also include a third primer complementary to a polymorphism, disclosed herein, located on the DGAT1 gene.

The invention includes a process for producing a protein of the invention, including preparing a DNA fragment including a nucleotide sequence which encodes the protein; incorporating the DNA fragment into an expression vector to obtain a recombinant DNA molecule which includes the DNA fragment and is capable of undergoing replication; transforming a host cell with the recombinant DNA molecule to produce a transformant which can express the protein; culturing the transformant to produce the protein; and recovering the protein from resulting cultured mixture.

Thus in a further aspect, the invention provides a purified protein encoded by the nucleic acid molecule of the invention and having biological activity of DGAT1. The terms "isolated" and "purified" as used herein, each refer to a protein substantially free of cellular material or culture medium when produced by recombinant DNA techniques, or chemical precursors or other chemicals when chemically synthesised. In certain preferred embodiments, the protein having biological activity of DGAT1 comprises an amino acid sequence and variants shown in FIGS. 4a and 4b (SEQ ID NOs: 2, 5 and 6). Furthermore, proteins having biological activity of DGAT1 that are encoded by nucleic acids which hybridise under stringent conditions to a nucleic acid comprising a nucleotide sequence shown in FIG. 2b (SEQ ID NOs: 1 and 4) are encompassed by the invention.

Proteins of the invention having DGAT1 activity can be obtained by expression of a nucleic acid coding sequence in a suitable host cell using techniques known in the art. Suitable host cells include prokaryotic or eukaryotic organisms or cell lines, for example, yeast, E. coli, insect cells and COS 1 cells. The recombinant expression vectors of the invention can be used to express a protein having DGAT1 activity in a host cell in order to isolate the protein. The invention provides a method of preparing a purified protein of the invention comprising introducing into a host cell a recombinant nucleic acid encoding the protein, allowing the protein to be expressed in the host cell and isolating and purifying the protein. Preferably, the recombinant nucleic acid is a recombinant expression vector. Proteins can be isolated from a host cell expressing the protein and purified according to standard procedures of the art, including ammonium sulfate precipitation, column chromatography (eg. ion exchange, gel filtration, affinity chromatography, etc.) electrophoresis, and ultimately, crystallisation (see generally "Enzyme Purification and Related Techniques". *Methods in Enzymology*, 22, 233-577 (1971)).

Alternatively, the protein or parts thereof can be prepared by chemical synthesis using techniques well known in the chemistry or proteins such as solid phase synthesis (Merrifield, 1964), or synthesis in homogeneous solution (Houben-wcyl, 1987).

It will of course be understood that a variety of substitutions of amino acids is possible while preserving the structure responsible for activity of the DGAT1 proteins disclosed herein. Conservative substitutions are described in the patent literature, as for example, in U.S. Pat. No. 5,264,558 or 5,487, 983. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, asparagine and glutamine could possibly be made. Substitutions among the charged acidic amino acids, aspartic acid and glutamic acid, could probably be made, as could substitutions among the charged basic amino acids, lysine and arginine. Substitutions among the aromatic amino acids, including phenylalanine, histidine, tryptophan and tyrosine would also likely be possible. These sorts of substitutions and interchanges are well known to those skilled in the art. Other substitutions might well be possible. Of course, it would also be expected that the greater percentage of homology ie. sequence similarity, of a variant protein with a naturally occurring protein, the greater the retention of activity.

A further advantage may be obtained through chimeric forms of the proteins, as known in the art. A DNA sequence encoding each entire protein, or a portion of the protein, could be linked, for example, with a sequence coding for the C-terminal portion of E. coli β-galactosidase to produce a fusion protein.

The proteins of the invention, or portions thereof, have numerous applications in turn. By way of example, each protein can be used to prepare antibodies which bind to a distinct epitope in an unconserved region of the protein. An unconserved region of the protein is one which does not have substantial sequence homology to other proteins.

Still further, the invention includes an antibody to a bovine DGAT1 variant protein encoded by a nucleotide sequence of the present invention as well as a diagnostic kit containing such an antibody.

Conventional methods can be used to prepare the antibodies.. For example, by using a DGAT1 peptide, polyclonal antisera or monoclonal antibodies can be made using standard methods. A mammal, (eg. a mouse, hamster, or rabbit) can be immunised with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunisation can be monitored by detection of antibody titers in plasma or serum. Standard ELISA or other immunoassay can be used to assess the levels of antibodies. Following immunisation, antisera can be obtained and, if desired, polyclonal antibodies isolated from the sera.

To produce monoclonal antibodies, antibody producing cells (lymphocytes) can be harvested from an immunised animal and fused with myeloma cells by standard somatic cell fusion procedures, thus immortalising these cells and yielding hybridoma cells. Such techniques are well known in the art. For example, the hybridoma technique originally developed by Kohler and Milstein (Kohler, 1975) as well as other techniques such as the human B-cell hybridoma technique (Kozbor, 1983) and screening of combinatorial antibody libraries (Huse, 1989). Hybridoma cells can be screened immunochemically for production of antibodies specifically reactive with the peptide, and monoclonal antibodies isolated.

The term "antibody" as used herein is intended to include fragments thereof which are also specifically reactive with the target protein. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments.

Another method of generating specific antibodies, or antibody fragments, reactive against the target proteins is to screen expression libraries encoding immunoglobulin genes, or portions thereof, expressed in bacteria, with peptides produced from the nucleic acid molecules of the present invention. For example, complete Fab fragments, VH regions and FV regions can be expressed in bacteria using phage expression libraries. See for example Ward et al., Huse et al., and McCafferty et al. (Ward, 1989); Huse 1989; McCafferty, 1990). Screening such libraries with, for example, a DGAT1 protein can identify immunoglobulin fragments reactive with that DGAT1. Alternatively, the SCID-hu mouse developed by Genpharm can be used to produce antibodies, or fragments thereof.

The polyclonal, monoclonal or chimeric monoclonal antibodies can be used to detect the proteins of the invention, portions thereof or closely related isoforms in various biological materials. For example, they can be used in an ELISA, radioimmunoassay or histochemical tests. Thus, the antibodies can be used to quantify the amount and location of a DGAT1 protein of the invention, portions thereof or closely related isoforms in a sample in order to determine the role of DGAT1 proteins. Using methods described hereinbefore, polyclonal, monoclonal antibodies, or chimeric monoclonal antibodies can be raised to non-conserved regions of DGAT1 and used to distinguish a particular DGAT1 from other proteins.

The polyclonal or monoclonal antibodies can be coupled to a detectable substance or reporter system. The term "coupled" is used to mean that the detectable substance is physically linked to the antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; and examples of suitable radioactive material include $^{125}I$; $^{131}I$, $^{35}S$ and $^{3}H$. In a preferred embodiment, the reporter system allows quantitation of the amount of protein (antigen) present.

Such an antibody-linked reported system could be used in a method for determining whether a fluid or tissue sample of a bovine contains a deficient amount or an excessive amount of the relevant DGAT1 protein. Given a normal threshold concentration of such a protein, test kits can be developed.

The availability of such antibodies gives rise to further applications. One is a diagnostic kit for identifying cells comprising an antibody (such as a monoclonal antibody) which binds to a protein comprising an amino acid sequence shown in FIG. 4a and 4b; means for detecting the antibody when bound to the protein, unreacted protein or unbound antibody; means for determining the amount of protein in the sample; and means for comparing the amount of protein in the sample with a standard. In some embodiments of the invention, the detectability of the antibody which binds to a specific DGAT1 protein is activated by the binding (eg. change in fluorescence spectrum, loss of radioisotopic label). The diagnostic kit can also contain an instruction manual for use of the kit.

Antibody-based diagnostics are of course not the only possibility. A further diagnostic kit comprises a nucleotide probe complementary to the sequence, or an oligonucleotide fragment thereof, shown in FIG. 2a and 2b, for example, for hybridisation with mRNA from a sample of cells; means for detecting the nucleotide probe bound to mRNA in the sample with a standard. In a particular aspect, the kit of this aspect of the invention includes a probe having a nucleic acid molecule sufficiently complementary with a sequence identified in FIG. 2a and 2b, or its complement, so as to bind thereto under stringent hybridisation conditions. "Stringent hybridisation conditions" takes on its common meaning to a person skilled in the art. Appropriate stringency conditions which promote nucleic acid hybridisation, for example, 6×sodium chloride/sodium citrate (SSC) at about 45° C. are known to those skilled in the art, including in Current Protocols in Molecular Biology, John Wiley & Sons, N.Y. (1989). Appropriate wash stringency depends on degree of homology and length of probe. If homology is 100%, a high temperature (65° C. to 75° C.) may be used. If homology is low, lower wash temperatures must be used. However, if the probe is very short (<100bp), lower temperatures must be used even with 100% homology. In general, one starts washing at low temperatures (37° C. to 40° C.), and raises the temperature by 3-5° C. intervals until background is low enough not to be a major factor in autoradiography. The diagnostic kit can also contain an instruction manual for use of the kit.

One of the major applications of the present invention is in the marker assisted selection of bovines having a polymorphism in the DGAT1 gene and which are associated with improved milk production traits. The invention therefore provides a diagnostic kit which can be used to determine the DGAT1 genotype of bovine genetic material, for example. One kit includes a set of primers used for amplifying the genetic material. A kit can contain a primer including a nucleotide sequence for amplifyg a region of the genetic material containing one of the polymorphisms described herein. Such a kit could also include a primer for amplifying the corresponding region of the normal DGAT1 gene, i.e. the sequence without polymorphisms. Usually, such a kit would also include another primer upstream or downstream of the region of interest complementary to a coding and/or non-coding portion of the gene. These primers are used to amplify the segment containing the mutation, i.e. polymorphism, of interest.

In particular, the invention is directed to the use of the polymorphisms in the DGAT1 gene in the genotyping of cows and bulls as well as to cows and bulls selected by such genotyping which have one or more of said polymorphisms in the DGAT1 gene. Such bulls so selected are of valuable breeding stock and the invention is also directed to the semen produced by such selected bulls for breeding purposes. Cows so selected are also useful as breeding stock as are their offspring. In addition, such cows may produce valuable dairy herds as the milk produced by such cows is produced in greater volumes than equivalent non-selected cows, and/or has an altered composition in that it comprises less milkfat and more milk protein. Such milk and products made therefrom also form part of the invention. It is also noted that the milk from these selected cows will be valuable as the fat content is not only decreased but is also characterised by being softer. Without being bound by theory, it is thought that this increased fat softness is due to the fatty acid composition being such that there is less saturated and more unsaturated fat in the milk of selected cows. Thus it is anticipated that products made from such milk will have processing advantages, such as in the production of more spreadable butter, as well as having a health benefit on consumers, as generally unsaturated fats are considered to be more "healthy" than saturated fats. The protein composition of milk produced by such selected cows is also altered. In particular, such milk comprises an altered protein yield compared to milk for nonselected cows and the casein:whey ratio is also altered which makes such milk valuable for cheese production.

Thus, the present invention involves genotyping bovine, both cows and bulls, for the DGAT1 polymorphisms disclosed herein, selected cows and bulls so genotyped, milk and semen produced by the selected cows and bulls so genotyped, offspring produced by the selected bovine, including embryos and cells (including cell lines) useful for cloning said selected bovine.

The actual genotyping is carried out using primers that target specific polymorphisms as described herein and that could function as allele-specific oligonucleotides in conventional hybridisation, Taqman assays, OLA assays, etc. Alternatively, primers can be designed to permit genotyping by microsequencing.

One kit of primers can include first, second and third primers, (a), (b) and (c), respectively. Primer (a) is based on a region containing a DGAT1 mutation such as described above. Primer (b) encodes a region upstream or downstream of the region to be amplified by primer (a) so that genetic material containing the mutation is amplified, by PCR, for example, in the presence of the two primers. Primer (c) is based on the region corresponding to that on which primer (a) is based, but lacking the mutation. Thus, genetic material containing the non-mutated region will be amplified in the presence of primers (b) and (c). Genetic material homozygous for the DGAT1 gene will thus provide amplified products in the presence of primers (b) and (c). Genetic material homozygous for the mutated gene will thus provide amplified products in the presence of primers (a) and (b). Heterozygous genetic material will provide amplified products in both cases.

The present invention also contemplates the modulation of milk production and content in non-human animals by modulating the activity of the DGAT1 protein. In particular, this aspect of the invention includes a method of modulating milk production and/or milk content in a lactating bovine, the method comprising administering to the bovine an effective amount of a nucleic acid molecule substantially complementary to at least a portion of mRNA encoding the bovine DGAT1 variant proteins and being of sufficient length to sufficiently reduce expression of said DGAT1, i.e. by use of antisense nucleic acids.

Antisense nucleic acids or oligonucleotides (RNA or preferably DNA) can be used to inhibit DGAT1 production in a bovine if this is considered desirable e.g. in order to produce a bovine capable of improved milk production, i.e. increased milk volume and decreased milkfat content. Antisense oligonucleotides, typically 15 to 20 bases long, bind to the sense mRNA or pre mRNA region coding for the protein of interest, which can inhibit translation of the bound mRNA to protein. The cDNA sequence encoding DGAT1 can thus be used to design a series of oligonucleotides which together span a large portion, or even the entire cDNA sequence. These oligonucleotides can be tested to determine which provides the greatest inhibitory effect on the expression of the protein (Stewart 1996). The most suitable mRNA target sites include 5'- and 3'-untranslated regions as well as the initiation codon. Other regions might be found to be more or less effective.

Alternatively, an antisense nucleic acid or oligonucleotide may bind to DGAT1 coding sequences.

In yet another embodiment, the invention provides a method of modulating milk production and/or milk content in a lactating bovine, including administering to the bovine an effective amount of a nucleic acid molecule having ribozyme activity and a nucleotide sequence substantially complementary to at least a portion of MRNA encoding a bovine DGAT1 and being of sufficient length to bind selectively thereto to sufficiently reduce expression of said DGAT1.

Rather than reducing DGAT1 activity in the bovine by inhibiting gene expression at the nucleic acid level, activity of the relevant DGAT1 protein may be directly inhibited by binding to an agent, such as, for example, a suitable small molecule or a monoclonal antibody.

Thus, the invention also includes a method of inhibiting the activity of bovine DGAT1 in a lactating bovine so as to modulate milk production and/or milk solids content, comprising administering an effective amount of an antibody to the relevant DGAT1.

The invention still further includes a method of modulating milk production and/or milk solids content by raising an autoantibody to a bovine DGAT1 in the bovine. Raising the autoantibody can include administering a protein having DGAT1 activity to the bovine.

In still a further embodiment, nucleic acids which encode DGAT1 proteins can be used to generate transgenic animals. A transgenic animal (eg. a mouse) is an animal having cells that contain a transgene, which transgene is introduced into the animal or an ancestor of the animal at a prenatal, eg. an embryonic stage. A transgene is DNA which is integrated into the genome of a cell from which a transgenic animal develops. In one embodiment, a bovine cDNA, comprising the nucleotide sequence shown in FIG. 2b, or an appropriate variant or subsequence thereof, can be used to generate transgenic animals that contain cells which express the relevant DGAT1. Likewise, variants can be used to generate transgenic animals. "Knock out" animals can also be generated.

Methods for generating transgenic animals, particularly animals such as mice, have become conventional in the art are described, for example, in U.S. Pat. Nos. 4,736,866 and 4,870,009. In such methods, plasmids containing recombinant molecules are microinjected into mouse embryos. In particular, the plasmids can be microinjected into the male pronuclei of fertilised one-cell mouse eggs; the injected eggs transferred to pseudo-pregnant foster females; and the eggs in the foster females allowed to develop to term. (Hogan, 1986). Alternatively, an embryonal stem cell can be transfected with an expression vector comprising nucleic acid encoding a DGAT1 protein, and cells containing the nucleic acid can be used to form aggregation chimeras with embryos from a suitable recipient mouse strain. The chimeric embryos can then be implanted into a suitable pseudopregnant female mouse of the appropriate strain and the embryo brought to term. Progeny harbouring the transfected DNA in their germ cells can be used to breed uniformly transgenic mice.

Such animals could be used to determine whether a sequence related to an intact DGAT1 gene retains biological activity of the encoded DGAT1. Thus, for example, mice in which the murine DGAT1 gene has been knocked out and containing the nucleic acid sequence identified in FIG. 2b or fragment or variant thereof could be generated. The animals could be examined with reference to milk production and content.

The pattern and extent of expression of a recombinant molecule of the invention in a transgenic mouse is facilitated by fusing a reporter gene to the recombinant molecule such that both genes are co-transcribed to form a polycistronic MRNA. The reporter gene can be introduced into the recombinant molecule using conventional methods such as those described in Sambrook et al., (Sambrook, 1989). efficient expression of both cistrons of the polycistronic mRNA encoding the protein of the invention and the reporter protein can be achieved by inclusion of a known internal translational initiation sequence such as that present in polivirus mRNA. The reported gene should be under the control of the regulatory sequence of the recombinant molecule of the invention and the pattern and extent of expression of the gene encoding a protein of the invention can Accordingly be determined by assaying for the phenotype of the reporter gene. Preferably the reporter gene codes for a phenotype not displayed by the host cell and the phenotype can be assayed quantitatively Examples of suitable reporter genes include lacZ (β-galactosidase), neo (neomycin phosphotransferase), CAT (chloramphenicol acetyltransferase) dhfr (dihydrofolate reductase), aphIV (hygromycin phosphotransferase), lux (luciferase), uidA (β-glucuronidase), Preferably, the reporter gene is lacZ which codes for β-galactosidase. β-galactosidase can be assayed using the lactose analogue X-gal (5-bromo-4-chloro-3-indolyl-β-D-galactopyranoside) which is broken down by β-galactosidase to a product that is blue in colour.

Still further transgenic applications of the invention arise from knocking out the endogenous gene encoding DGAT1 in non-human mammals and replacing this with a bovine transgene, in order to obtain a desired effect. This is particularly true in cattle raised for milk production. For example, additional copies of the bovine gene encoding DGAT1 can be inserted as a transgene, or the endogenous gene associated with a high level expression promoter in a transgene. It may also prove advantageous to substitute a defective gene rather than delete the entire sequence of DNA encoding for a protein having DGAT1 activity. A method of producing a transgenic bovine or transgenic bovine embryo is described in U.S. Pat. No. 5,633,076, issued May 27, 1997, for example.

These transgenic animals of the invention can again be used to investigate the molecular basis of DGAT1 action. For example, it is expected that mutants in which one or more of the conserved cysteine residues has been deleted would have diminished activity in relation to a DGAT1 protein in which all such residues are retained. Further, deletion of a proteolytic cleavage site would likely result in a mutant lacking biological activity of DGAT1.

Transgenic animals of the invention can also be used to test substances for the ability to prevent, slow or enhance DGAT1 activity. A transgenic animal can be treated with the substance in parallel with an untreated control transgenic animal. Substances which could be tested in this way include proteins extracted from foods ingested by the animal, For example, proteins extracted from pastoral grasses and other fodder can be tested to determine their effect on DGAT1 activity, including to determine Whether breed-specific effects can be induced.

Thus, in further aspects, the invention provides transgenic non-human animals. These include by way of example only a transgenic bovine having a genome lacking a gene encoding a protein having biological activity of DGAT1 (or indeed any DGAT1 activity at all); a transgenic mouse having a genome containing a gene encoding a bovine protein having biological activity of any DGAT1; and a transgenic bovine having a gene, encoding a bovine protein having biological activity of a bovine DGAT1 and heterologous nucleotide sequence antisense to the gene. The transgenic bovine can include a gene encoding a nucleic acid sequence having ribozyme activity and in transcriptional association with the nucleotide sequence antisense to the gene.

The invention further provides a transgenic bovine having a genome which includes additional copies of a gene encoding a protein having biological activity of DGAT1 or copies of a gene encoding a protein having biological activity of DGAT1 under control of a high expression promoter.

These are but a selection of the applications of this invention. Others will be apparent to those persons skilled in this art and are in no way excluded. To the contrary, the invention extends to cover not only the specific teaching provided but also all variations and modifications which are within the skill and contemplation of the addressee.

The invention will now be defined by specific examples which are illustrative only and are not intended to limit the invention in any way.

Experimental

1. Location of the Gene Responsible for the Observed QTL

Construction of a BAC contig Spanning the BULGE9-BULGE30 Interval.

In order to clone the gene(s) responsible for the observed QTL effect, a BAC contig spanning the corresponding marker interval was constructed. This was accomplished by screening a BAC library by filter hybridisation with the microsatellite markers available for proximal BTA14q, as well as with human cDNA clones mapping to the orthologous chromosome segment on the human RH transcript map: 8q23.3-ter (Riquet et al., (1999)). The ends of the isolated BACs were sequenced, sequence tagged sites (STS) developed from the corresponding sequences, and mapped onto a bovine x hamster whole genome radiation hybrid panel. This STS content mapping approach lead to the construction of the BAC contig shown in FIG. 1.

DGAT1 maps to the BULGE9-BULGE30 Interval and is a Strong Positional Candidate for the QTL.

A murine gene encoding a protein with Diacylglycerol-o-acyltransferase (DGAT1) activity was identified (Cases et aL, (1998)) and shown to completely inhibit lactation when knocked out in the mouse (Smith et al., (2000)). This gene was reported in the human to map to HSA8qter (Cases et al., (1998)), ie. in the region orthologous to that containing the bovine QTL. Screening the publicly available databases with the published murine and human DGAT1 cDNA sequences allowed identification of (i) a human BAC clone containing the human DGAT1 gene (AF205589), and (ii) three bovine Expressed Sequence Tags (AW446908; AW446985; AW652329) jointly covering approximately two thirds of the bovine gene. Aligning the human DGAT1 genomic sequences with the human and bovine cDNA sequences allowed the corresponding intron-exon boundaries to be identified. Primers were developed to PCR amplify a portion of the bovine DGAT1 gene. Screening the BACs composing the BULGE9-BULGE30 contig clearly indicated that the bovine DGAT1 gene was contained in a subset of the BACs allowing us to accurately position the DGAT1 gene in the contig of FIG. 1.

These results demonstrated that the map position of DGAT1 coincided with the most likely position of the chromosome 14 QTL as determined by linkage and linkage disequilibrium analyses. Knowing that the QTL primarily affects fat content, knowing the enzymatic activity of DGAT1 and the effect of a DGAT1 knock-out on lactation, this gene was considered to be a very strong positional candidate for the corresponding QTL.

Organisation of the Bovine DGAT1 Gene

The organisation of the bovine DGAT1 gene was determined by sequence analysis of one of the DGAT1 containing BACs. Primers were designed based on the available bovine, murine and human cDNA sequences which were either used for direct sequencing of the BAC clone or to generate PCR products corresponding to different parts of the bovine DGAT1 gene from this BAC which were then subjected to cycle-sequencing. All available sequences were then merged using the Phred/Phrap software (Ewing et al., (1998); Ewing & Green, (1998); Gordon et al., (1998)) to yield the consensus sequence shown in FIGS. 2*a* and *b*.

Figure 3:
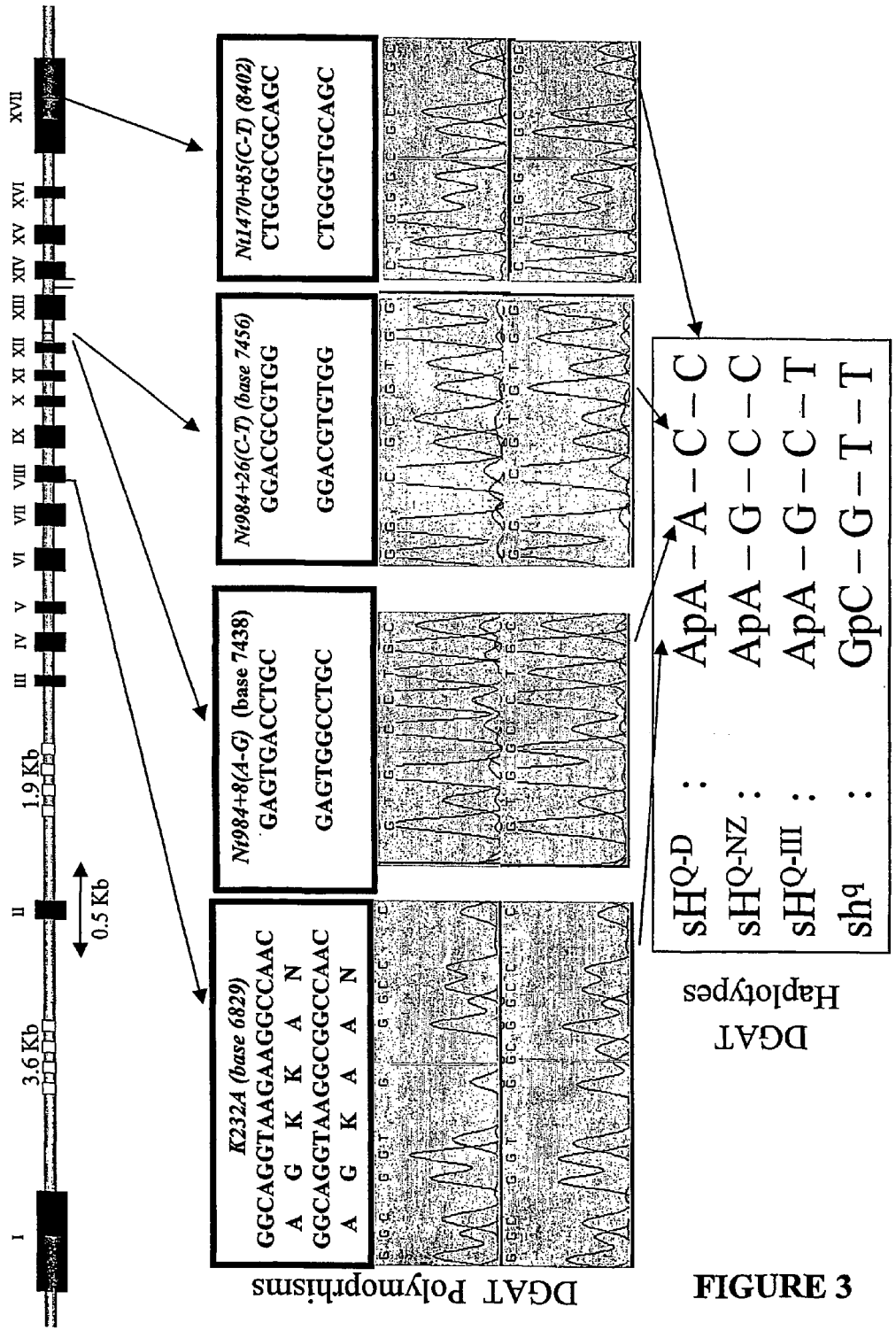
FIG. 3: Shows the genomic organization, four polymorphisms and haplotypes found in the bovine DGAT1 gene. Leader and trailer sequences are shown in light grey, coding sequences in dark grey and intronic sequences as a hollow line. The positions of four of the identified polymorphisms are marked as shown on the gene, and detailed in the underlying boxes including the corresponding sequence traces All the sequence variations are summarised in Table 1. The four DGAT1 haplotypes which were found in the Dutch and New-Zealand Holstein-Friesian population as defined by these polymorphisms are shown and referred to as "sH$^{Q-D}$", "sH$^{Q-NZ}$", "sH$^{Q-III}$" for the fat increasing haplotypes and "sh$^q$" for the fat decreasing haplotype.

RT-PCR, 5' and 3' RACE experiments were performed on mRNA isolated from bovine mammary gland and the obtained PCR products subjected to cycle sequencing. Comparison of the genomic and cDNA sequences showed that the bovine DGAT1 gene spans 8.6 Kb and comprises 17 exons measuring 121.8 bp on average (range: 42 -436 bp) and allowed intron-exon boundaries to be identified (FIGS. 2a, 2b and 3). The cDNA sequence is also set out in SEQ ID NO: 4. While the first two introns are respectively 3.6 and 1.9 Kb long, the remaining 14 introns are only 92.4 bp long on average (range: 70 -215 bp). All introns conform to the GT-AG rule and are strictly conserved between human and bovine. The bovine DGAT1 gene is transcribed in a mRNA comprising >31 bp of 5' UTR sequence (FIG. 2a), 1470 bp coding for a protein of 489 amino-acids, and 275 bp of 3' UTR sequence including a canonical AATAAA polyadenylation signal. The human and bovine DGAT1 nucleotide (coding) and protein sequences are respectively 89.5% and 92.5% identical (FIGS. 2a, 2b, 4a and 4b). In addition, an alternative splicing variant is predicted in the bovine for exon VIII (FIG. 2b). The corresponding bovine cDNAs are predicted to encode proteins comprising respectively 489 and 467 (alternative splicing variant) amino-acid residues (FIGS. 4a and 4b).

The Predicted "Q" and "q" QTL Alleles Differ by a Non Conservative Lysine to Alanine Amino-acid Substitution in the DGAT1 Gene.

Assuming that DGAT1 is indeed the QTL, it is predicted that the identified "Q" and "q" QTL alleles will correspond to functionally distinct DGAT1 alleles, ie. will differ at one or more mutations causing these alleles to be functionally different. To test this hypothesis, the structure of the DGAT1 gene in individuals predicted to be of different QTL genotypes: "QQ", "Qq" and "qq" was examined. More specifically, the DGAT 1 gene from:
 (i) two sires with "$H^{Q-D}/h^q$" genotype as well as two of their "$H^{Q-D}/H^{Q-D}$" offspring, two of their "hq/$h^q$" offspring and one "$H^{Q-D}/h^q$" offspring, and
 (ii) one "$H^{Q-NZ}/h^q$" sire with one of its "$H^{Q-NZ}/H^{Q-NZ}$" offspring was analysed wherein $H^{Q-D}$ corresponds to the Dutch Q haplotype and $H^{Q-NZ}$ corresponds to the New Zealand Q haplotype, and primer pairs were designed that allowed for the amplification from genomic DNA of (i) the coding portion of exon I, (ii) exon II, and (iii) the chromosome regions spanning exons III to XVII. The corresponding PCR products from the selected individuals were cycle-sequenced and the resulting sequences examined with the Polyphred software.

Additional sequencing analysis, as described above, on DNA from a range of breeds revealed additional polymorphisms included in Table 1 (see Methods section for breeds). Four such polymorphisms were investigated further:
 (i) K232A: a substitution of a ApA by a GpC dinucleotide in exon VIII (respectively positions 694 and 695 counting from the start codon in the cDNA). The substitution of these two adjacent nucleotides results in a non conservative lysine (hydrophylic basic amino acid) to alanine (hydrophobic amino acid) substitution in the DGAT1 protein. The lysine residue affected by this polymorphism is conserved in the human and murine DGAT1 sequences. Together with the resulting change in the electrical charge of the protein, this strongly suggests that this amino-acid substitution is likely to result in a functional difference between the two corresponding alleles and to be at least partly responsible for the observed QTL effect.

(ii) Nt984+8(Base 7438 A-G): A A to G substitution in intron 12, eight base pairs downstream of exon XII. Following standard nomenclature, this polymorphism will be referred to as Nt984+8(A-G). This polymorphism cannot be predicted as such to modify the functionality of the corresponding alleles although an effect on the splicing mechanism cannot be excluded given its proximity to the intron-exon boundary.

(iii) Nt984+26(Base 7456 C-T): A C to T substitution in intron 12, 26 base pairs downstream of exon XII. Following standard nomenclature, this polymorphism will be referred to as Nt984+26(Base 7456 C-T). Again, this polymorphism cannot be predicted as such to modify the functionality of the corresponding alleles although an effect on the splicing mechanism cannot be excluded given its proximity to the intron-exon boundary.

(iv) Nt1470+85(Base 8402 C-T): A C to T substitution in the 3' UTR. Following standard nomenclature, this polymorphism will be referred to as Nt1470+85(Base 8402 C-T). Again, this polymorphism cannot be predicted as such to modify the functionality of the corresponding alleles although an effect on polyadenylation or mRNA stability cannot be excluded.

Conclusion

These four polymorphisms were shown to assort into three distinct SNP haplotypes referred to as $sH^{Q-D}$, $sH^{Q-NZ}$ and $sh^q$ because in the sequenced samples they coincided respectively with microsatellite haplotypes $\mu H^{Q-D}$, $\mu H^{Q-NZ}$ and $\mu h^q$. The base pair compositions of these three SNP haplotypes are shown in FIG. 3.

Because the $sH^{Q-NZ}$ and $sh^q$ marker haplotypes share the G residue at the DGAT1 Nt984+8(Base 7438 A-G) site, the causality of this polymorphism in the determinism of the QTL could be excluded. For the three remaining polymorphic sites, however, the DGAT1 haplotypes associated with marker haplotypes sHED and sHQIz proved identical to each other while different from the $sh^q$ DGAT1 haplotype. Either of these three polymorphisms could therefore be responsible for the observed QTL effect. The Nt984+26(Base 7456 C-T) and Nt1470+85(Base 8402 C-T) polymorphisms are a priori more likely to be neutral with respect to DGAT1 activity because of their respective location in an intron and the 3' UTR and likewise the other non coding or neutral polymorphism shown in Table 1. A direct effect of the K232A mutation on DGAT1 activity, however, is very plausible. Indeed, the corresponding lysine residue is conserved amongst all examined mammals (i.e. human, mouse, rat, pig, sheep, bison) demonstrating its functional importance (FIG. 5). The evolutionary conservation of this lysine residue also demonstrates that the K residue characterizing the $sH^{Q-D}$ and $sH^{Q-NZ}$ marker haplotypes is more than likely the ancestral state and that it is the A residue characterizing the $sh^q$ haplotypes that corresponds to a more recently evolved state.

2. Genotype Testing and Analysis I

This summarises the genotype testing and subsequent analysis of Holstein-Friesian animals sourced from New Zealand and Holland which were tested for the presence of the K232A polymorphism. Reference to allele "Q" corresponds to the K residue and allele "q" to the A residue (as shown in FIG. 3 and Table 1).

An oligonucleotide ligation assay (OLA) was developed as described in the method section below that allows for efficient genotyping of the four DGAT1 polymorphisms simultaneously. This OLA-test was used to genotype a previously described (Farnir et. al., 2000) "grand-daughter design" (i.e. series of paternal half-brother pedigrees) comprising 1,818

Dutch Holstein-Friesian sires as well as a "daughter design" (i.e. series of paternal half-sister pedigrees) comprising 529 New Zealand Holstein-Friesian cows selected according to phenotype as described below. The marker linkage phase for each individual was determined as described below.

Figure 6:
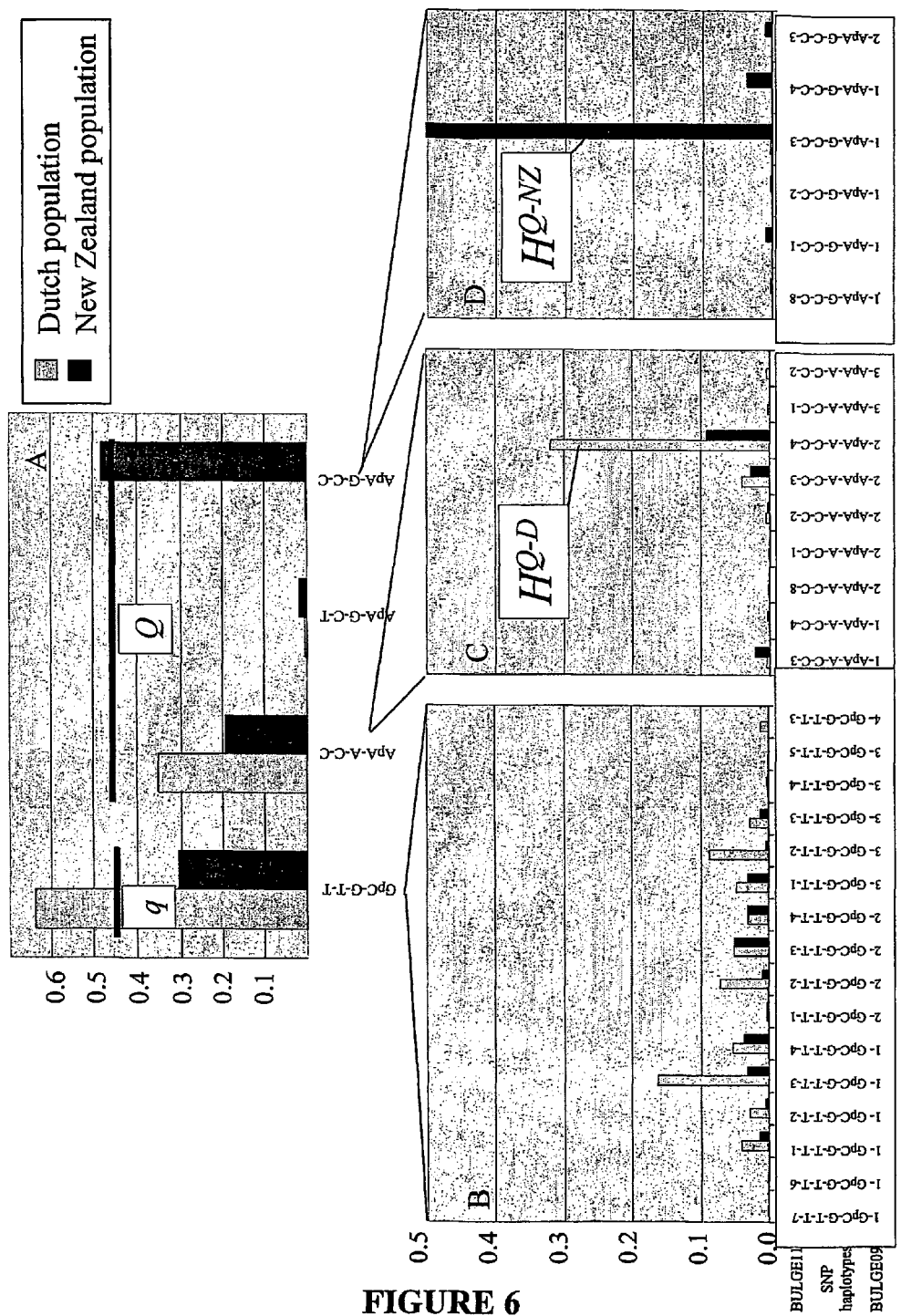
FIG. 6: A. Shows the frequency distribution of observed DGAT1 SNP haplotypes in the Dutch and New Zealand Holstein-Friesian dairy cattle populations. B-D. Shows the frequency distribution of the combined microsatellite (BULGE09-BULGE11) and SNP DGAT1 haplotypes. The H$^{Q-D}$ and H$^{Q-NZ}$ haplotypes are shown.

FIG. 6 summarizes the frequency distribution of DGAT1 haplotypes encountered in the Dutch and New Zealand populations respectively. Four distinct SNP haplotypes were identified. Three of these correspond to the $sH^{Q-D}$, $sH^{Q-NZ}$ and $sh^q$ that were previously identified by sequencing, and jointly account for 99% and 98% of the chromosomes in the Dutch and New-Zealand populations respectively. A fourth minor haplotype was found accounting for the remaining 1% and 2% of the chromosomes. As this haplotype codes for a K residue at position 232 it was assumed to correspond to a fat increasing "Q" allele and was therefore referred to as $sH^{Q-III}$ (FIG. 3). The observation that the K residue is found on three distinct DGAT1 haplotypes while the A residue is found on a unique DGAT1 haplotype is in agreement with K being the more ancient state.

The $sH_{Q-D}$ and $sH^{Q-NZ}$ SNP haplotypes (coding for a K residue at position 232) appear to be in strong linkage disequilibrium (LD) with the flanking microsatellite markers BULGE09 and BULGE11, as they are in essence associated with unique microsatellite haplotypes corresponding respectively to the previously defined $\mu H^{Q-D}$ and $\mu H^{Q-NZ}$ haplotypes (FIG. 6C&D). In sharp contrast, the $sh^q$ haplotype (coding for an A residue at position 232) is nearly evenly distributed across more than ten distinct microsatellite haplotypes (FIG. 6B).

These observations are in excellent agreement with the results of the combined linkage and LD analysis (Fernier et. al., 2000). These studies indeed predicted (i) that in the Dutch population the vast majority (estimates ranging from 81% to 92%) of "Q" allele (=K) would reside on the $\mu H^{Q-D}$ microsatellite haplotype, (ii) that in the New Zealand population a large fraction (estimates ranging from 36% to 51%) of "Q" alleles would reside on haplotype $\mu H^{Q-NZ}$ (we now see that the remainder correspond mainly to the $\mu H^{Q-D}$ microsatellite haplotype) and (iii) that in both populations the "q" alleles (=A) would correspond to multiple marker haplotypes, corresponding to $h^q$.

Figure 7:
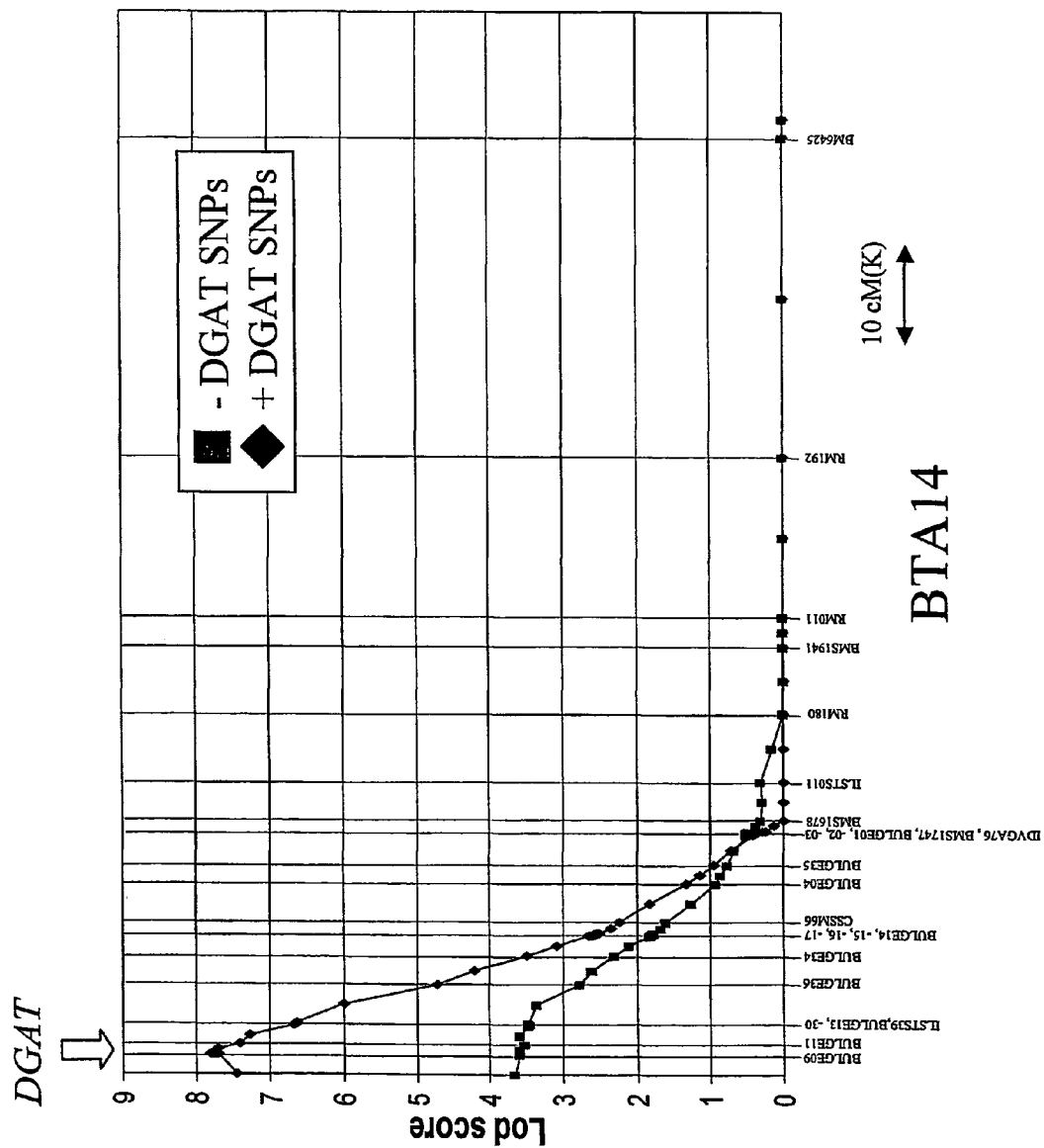
FIG. 7: Shows the lod score due to LD when including (+) or excluding (−) the four DGAT1 polymorphisms shown in FIG. 3 in a combined linkage and LD multipoint maximum likelihood mapping method. The lod score corresponds to the log$_{10}$ of the ratio between the likelihood of the data assuming LD and linkage between the markers and the likelihood of the data assuming linkage in the absence of LD. The positions of the microsatellites and SNP markers utilized in the analysis are shown on the X-axis, while the position of the DGAT1 SNPs is marked by a red arrow at the top of the figure.

FIG. 7 illustrates the gain in LD signal that could be obtained in the Dutch Holstein-Friesian grand-daughter design when adding the DGAT1 polymorphisms to the previously available markers for proximal BTA14q and performing a joint linkage and LD multipoint analysis (Fernier et. al., 2000) using the sires "daughter yield deviations" (DYD (Van Raden and Wiggans, 1991) corresponding to half breeding values) for milk fat percentage as phenotype. It can be seen that the lod score attributable to LD essentially doubles (from 3.7 to 7.8), and maximizes exactly at the position of the DGAT1 gene. This result strongly supports the causal involvement of the DGAT1 gene in the QTL effect. The corresponding ML estimates of the "Q" to "q" allele substitution effect ($\alpha/2$) (as defined in Falconer and Mackay, 1996), residual standard deviation ($\sigma$), population frequency of the "Q" allele ($f_Q$), number of generations to coalescence (g) and heterogeneity parameter ($\rho$) were respectively 0.11% ($\alpha/2$), 0.06% ($\sigma$), 0.20 ($f_Q$), 5 (g) and 0.84 ($\rho$).

Using the same Dutch Holstein-Friesian population, the additive effect of the DGAT1 K232A polymorphism on milk yield and composition was examined. The sons DYDs for milk yield (kgs), protein yield (kgs), fat yield (kgs), protein percentage and fat percentage, were analysed using a mixed model including (i) a regression on the number of K alleles in the genotype (0, 1 or 2), and (ii) a random polygenic component estimated using an individual animal model and accounting for all known pedigree relationships. Table 2 below, reports the obtained results. It can be seen that the K232A mutation has an extremely significant effect on the five analysed dairy traits. The proportion of the trait variance explained by this polymorphism in this population ranges from 8% (protein yield) to 51% (fat percentage), corresponding to between 10% (protein yield) and 64% (fat percentage) of the genetic variance (=QTL +polygenic).

Note that the proportion of the variance explained by the full model ($1-r^2_{error}$) is of the order of 70% for the yield traits and 80% for the percentage traits, which is in agreement with the known reliabilities of the corresponding DYDs (Van Raden and Wiggans, 1991). An interesting feature of this QTL effect is that the "q" to "Q" substitution increases fat yield, while decreasing milk and protein yield, despite the strong overall positive correlation characterizing the three yield traits.

TABLE 2

Effect of the DGAT1 K232A mutation on sire's daughter yield deviations (DYDs) for milk yield and composition.

| Trait | $\alpha/2$ | $r^2_{QTL}$ | p-value$_{QTL}$ | $r^2_{polygenic}$ | $r^2_{error}$ |
|---|---|---|---|---|---|
| Milk yield (Kgs) | −158 Kgs | 0.18 | 5.00E−35 | 0.49 | 0.32 |
| Fat yield (Kgs) | 5.23 Kgs | 0.15 | 1.57E−29 | 0.55 | 0.30 |
| Protein yield (Kgs) | −2.82 Kgs | 0.08 | 1.70E−15 | 0.65 | 0.26 |
| Fat % | 0.17% | 0.51 | 4.33E−122 | 0.29 | 0.19 |
| Protein % | 0.04% | 0.14 | 5.05E−28 | 0.66 | 0.20 |

(i) $\alpha/2$: QTL allele substitution effect on DYD (half breeding value), corresponding in the mixed model to the regression coefficient on the number of K alleles in the DGAT1 K232A genotype, and to $\alpha/2$, where $\alpha$ is defined according to ref. Falconer and Mackay, 1996.
(ii) $r^2_{QTL}$: proportion of the trait variance explained by the DGAT1 K232A polymorphism.
(iii) p-value$_{QTL}$: statistical significance of the DGAT1 K232A effect.
(iv) $r^2_{polygenic}$: proportion of the trait variance explained by the random, polygenic effect in the mixed model.
(v) $r^2_{error}$: proportion of the trait variance unexplained by the model.

The two previous analyses examined the effect of the DGAT1 polymorphism on estimated breeding values. By definition, this phenotype will only account for the additive component of the DGAT1 effect, and justifies the use of a regression on the number of K alleles in the mixed model. To evaluate the dominance relationship between the DGAT1 alleles, the effect of the K232A genotype on the lactation values (first yield deviations (Van Raden and Wiggans, 1991)) of the cows composing the New Zealand daughter design were analysed. This was achieved by using a mixed model including (i) a fixed effect corresponding to the K232A genotype, and (ii) a random polygenic component accounting for all known pedigree relationships ("animal model"). Very significant effects of K232A genotype on all examined yield and composition traits were found in this population as well (Table 3, below), accounting for between 1% (protein yield) and 31% (fat percentage) of the trait variance. The observed dominance deviations, d, corresponding to the difference between the genotypic value of the KA genotype and the midpoint between the AA and KK genotypic values (Falconer and Mackey, 1996) are shown in Table 3 below. Genotypic values of the heterozygous genotype are systematically in between alternate homozygotes. None of the d-values proved to be significantly different from zero, indicating an absence of dominance. Average K to A QTL allele substitution effects, $\alpha$ (Falconer and Mackey, 1996), were computed from the estimates of a- and d-values, as well as the population frequencies of the K and A alleles (Table 3). The predicted substitution effects are in good agreement with those computed from the grand-daughter design: the K allele increases fat yield, fat % and protein %, while decreasing milk and protein yield. The absolute values of a estimated from the grand-daughter and daughter design are in perfect agreement for fat and protein %, while for the yield traits estimates are larger in the grand-daughter design when compared to the daughter design. The exact reasons for this are being explored. It could be due to the fact that the sire population in the grand-daughter design is not representative of the cow population in general, or to intrinsic differences between the Dutch and New-Zealand populations and/or environment.

where $y_1$ is the lactation value of cow i, $g_i$ is a fixed effect corresponding to the DGAT1 genotype (KK, KA, or AA), $a_i$ is a random polygenic component accounting for all known pedigree relationships ("animal model" Lynch and Walsh, 1997) and $e_i$ is a random residual. In both instances, maximum likelihood solutions for $\beta$, $g_i$, $\alpha_i$, $e_i$, $\sigma^2_a$, $\sigma^2_e$ were obtained using the MTDFREML program (Boldman et al, 1997).

TABLE 3

Effect of the DGAT1 K232A mutation on cows' lactation values for milk yield and composition.

| Trait | a | d | α | $r^2_{QTL}$ | p-val$_{QTL}$ | $r^2_{polygenic}$ | $r^2_{error}$ |
|---|---|---|---|---|---|---|---|
| Milk yield (Kgs) | −144 Kgs | −42 Kgs | −161 Kgs | 0.03 | 1.05E−8 | 0.54 | 0.43 |
| Fat yield (Kgs) | 7.82 Kgs | −0.89 Kgs | 7.46 Kgs | 0.09 | 1.77E−20 | 0.46 | 0.45 |
| Protein yield (Kgs) | −2.34 Kgs | −0.76 Kgs | −2.64 Kgs | 0.01 | 4.35E−2 | 0.37 | 0.42 |
| Fat % | 0.41% | 0.03% | 0.42% | 0.31 | 2.5E−108 | 0.49 | 0.20 |
| Protein % | 0.08% | 0.03% | 0.08% | 0.04 | 1.60E−20 | 0.72 | 0.24 |

(i) a: half the difference between the genotypic values of the KK and AA genotypes (Falconer and Mackey, 1996).
(ii) d: dominance deviation (Falconer and Mackey, 1996): deviation of the KA genotypic value from the midpoint between the AA and KK genotypic values; none of these proved to be significantly different from zero.
(iii) α: average K to A substitution effect, computed as "a + d(q − p)" (Falconer and Mackey, 1996), where q is the allelic frequency of K (= 0.7) and p of A (= 0.3)
(iv) $r^2_{QTL}$: proportion of the trait variance explained by the DGAT1 K232A polymorphism.
(v) p-val$_{QTL}$: statistical significance of the DGAT1 K232A effect.
(vi) $r^2_{polygenic}$: proportion of the trait variance explained by the random, polygenic effect in the mixed model.
(vii) $r^2_{error}$: proportion of the trait variance unexplained by the model.

Pedigree material and phenotypes. The pedigree material used for the association studies comprised a "grand-daughter design" (Weller et. al., 1990) counting 1,818 Holstein-Friesian bulls sampled in the Netherlands, as well as a "daughter-design" (Weller et. al., 1990) counting 529 Holstein-Friesian cows sampled in New Zealand. The phenotypes of the sires were "daughter yield deviations" (DYD: unregressed weighted averages of the daughter's lactation performances adjusted for 1 systematic environmental effects and breeding values of the daughter's dams and expressed as deviations from the population mean (Van Raden and Wiggans, 1991)) obtained directly from CR-Delta (Arnhem—The Netherlands). The phenotypes of the cows were "lactation values" (first lactation yield deviations (YD), i.e. weighted average lactation performances expressed as deviations from the population mean, adjusted for management group, permanent environmental effects and herd-sire interaction effects (Van Raden and Wiggans, 1991)) obtained directly from Livestock Improvement Corporation (Hamilton—New Zealand).

Combined linkage and linkage disequilibrium analysis and association studies. The maximum likelihood procedure for combined linkage and linkage disequilibrium analysis is described in detail in Farnir, 2000. The association study in the grand-daughter design was performed using the following model:

$$Y_i = \mu + \beta x_i + a_i + e_i$$

where $y_i$ is the DYD of son i, μ is the overall population mean, β is a fixed regression coefficient estimating the A to K allele substitution effect, $x_i$ is an indicator variable corresponding to the number of K alleles in the K232A genotype, $a_i$ is a random polygenic component accounting for all known pedigree relationships ("animal model" Lynch and Walsh, 1997) and $e_i$ is a random residual. The association study in the daughter design was performed using the model:

$$y_i = \mu + g_i + a_i + e_i$$

3. G Notyp T Sting and Analysis II

This summarises the genotype testing and subsequent analysis of Holstein-Friesian, Jersey and Ayrshire animals in a separate population from those presented in genotype testing and analysis I, above.

Progeny Tested Sires

Each year Livestock Improvement Corporation (New Zealand) progeny test some 200-300 bulls per year. This entails the bulls being genetically evaluated on the basis of 50-85 daughters per sire. The sires are evaluated for milk fat, milk protein, milk volume and 20 non-production traits. Semen has been retained from all progeny tested sires since the early 1970s. DNA was extracted from the semen and genotyped for the K232A DGAT1 polymorphism using the 7900 Taqman system (see Methods section below).

Statistical analysis was undertaken on this dataset using Restricted Maximum Likelihood (REML) and the average information algorithm (Johnson and Thompson, 1995). The linear model included the fixed effects of DGAT1 (3 classes; 0, 1 and 2 copies of the Q allele i.e. the K residue) and a covariate corresponding to the proportion of overseas genetics. The random effect was animal with a relationship matrix based on all known relationships. Daughter yield deviations (DYDs), weighted averages of a sire's daughter's lactation performances expressed as deviations from the population mean (van Raden and Wiggans 1991) were used as the phenotypic measurement. The phenotypes were weighted by a weighting factor based on the variance of the DYD for a son being:

$$\text{Var } DYD = \left[ \frac{1 + (n-1)\frac{1}{4}h^2}{n} \right] \sigma_p^2$$

where Var DYD is the variance of son's DYD; n is the number of daughters contributing to the DYD; $h^2$ is the heritability, which was taken as 0.35 for yield traits.

The dataset was analysed separately for the 3 major breeds; Holstein-Friesian, Jersey and Ayrshire.

Seventeen hundred and thirteen Holstein-Friesian sires were included in the analysis. The effect of the DGAT1 polymorphism was extremely significant for the three milk production traits (Table 4). With each additional Q allele the level of milk fat production increases by approximately 6 kg per lactation, milk protein production decreases by approximately 2.5 kg per lactation and milk volume decreases by approximately 125 litres per lactation.

TABLE 4

Effect of the DGAT1 polymorphism on milk production in the Holstein-Friesian bull population (kilograms per lactation).

|  | Fat | Protein | Milk |
|---|---|---|---|
| qq | 0 | 0 | 0 |
| Qq | 6.86 | −2.13 | −128 |
| QQ | 11.83 | −4.80 | −266 |
| st. error | 0.87 | 0.68 | 24 |

The effects for the Jersey and Ayrshire breeds were less significant than those of the Holstein-Friesian breed but were consistent in direction of effects.

Daughters for Milk Components

Data collection was integrated with LIC's herd testing service using a sample of 102 herds involved in LIC's Sire Proving Scheme (SPS) in 1995. In addition to milk volume from herd testing, the concentrations of fat, crude protein (total nitrogen), casein, whey and lactose were determined. The data was collected from over 3,000 cows born in 1996 and first calving in the 1998 spring season, these being predominantly the daughters of approximately 220 SPS bulls. The milk characteristics were measured at three herd tests on each cow, with each herd having a herd test in each of the Sept/Oct, Nov/Dec and Jan/Feb periods. The Milkoscan FT120, which employs Fourier transform infrared spectrophotometry with enhanced milk calibrations (Foss Electric Application Note Nos. 95, P/N 492280 and 102, P/N 578377), was used to determine the milk component concentrations.

Nine hundred and twelve daughters were genotyped for the DGAT1 polymorphism using the OLA system. Analysis was undertaken using SAS (Statistics, Version 5, 1985) fitting a general linear model. The model included sire and maternal grandsire as fixed effects, DGAT1 polymorphism (3 classes; 0, 1 and 2 copies of the Q allele), covariates including 16ths of Holstein-Friesian, Jersey, Ayrshire and other, proportion of overseas genetics within the Holstein-Friesian, Jersey and Ayrshire breeds. Yield deviations that were pre-adjusted for herd, stage of lactation among other fixed effects were used (Johnson et al 2000).

The DGAT1 polymorphism is statistically significant for Lactose, casein, beta-casein and whey yield and also for casein and beta-casein percent as outlined in Table 5.

TABLE 5

Effect of the DGAT1 polymorphism on milk components.

| Trait | qq | Qq | QQ | p-value |
|---|---|---|---|---|
| Lactose yield* | 48 | 23 | 0 | <0.0001 |
| Casein yield* | 11.0 | 5.8 | 0 | 0.01 |
| Casein % | −0.13 | −0.06 | 0 | <0.0001 |
| Whey yield* | 6.86 | 2.31 | 0 | <0.0001 |
| β-casein yield* | 3.98 | 2.19 | 0 | 0.05 |
| β-casein % | −0.43 | −0.23 | 0 | 0.0001 |

*Units = g/day for lactose, casein and whey yield and g/litre for β-casein yield Daughters for Solid Fat Content Six hundred and ninety-two daughters were phenotyped for solid fat content. Solid fat content of the milkfat is a characteristic which has a major influence on the functionality of milkfat products, and in particular has a significant effect on the hardness of butter (MacGibbon & McLennan, 1987). The solid fat content at 10° C. (SFC 10) was used for comparison of the properties of the milkfat as it relates well to the sectility hardness measurement of butter, a major functional property. Thus the performance of milkfat products may be predicted from the characteristics of the milk produced. The solid fat content (SFC) of the extracted fat was determined by pulsed nuclear magnetic resonance (NMR) and expressed as percentage solid fat (MacGibbon & McLennan, 1987). As the milkfat was melted to remove any thermal history, prior to recrystallization under standard conditions, the SFC simply reflects the chemical composition of the milkfat.

The 692 daughters were a subset of the 912 daughters that were phenotyped and genotyped for the results presented in Table 2. The solid fat content measures were collected over 2 lactations. Breeding values were calculated using an animal model similar to that of Johnson et al 2000.

The same statistical model was fitted for solid fat content as was for the milk component analysis. The DGAT1 polymorphism has a statistically significant effect (p-value <0.0001) on solid fat content, increasing it by approximately by 1% for each addition of the Q allele.

This effect was further confirmed in 50 daughters (predominantly Holstein-Friesian) that were farmed at one location and measured for SFC on the same day. The estimated effect for of the DGAT1 polymorphism on SFC was to increase it by approximately 2% per addition of each Q allele. This finding was significant at the five percent threshold level.

The genetic standard deviation for SFC is 2.25 (D Johnson personal communication) and thus the effect of DGAT1 is approximately 0.5 of a genetic standard deviation.

4. Relative Transcript Levels of the Splice Variant

Real time PCR experiments were conducted using reverse transcribed mRNA isolated from lactating bovine mammary gland(s) (see experimental methods). These experiments revealed that the alternatively spliced transcript as shown on FIG. 2b, was approximately 100 fold less abundant than the full length transcript.

METHODS SECTION

In order to identify other polymorphisms within the bovine DGAT1 gene, DNA was isolated from sperm, PCR amplified and then using primers designed from the sequence shown in FIGS. 2a and 2b and/or the cDNA sequence (SEQ ID NO: 4) direct sequenced on an ABI 3100. The breeds examined were:

Ayrshire, Angler, Belgian Blue, Blond D'Aquitaine, Brown Swiss, Charolais, Red Devon, Devon, Dexter, Friesian, Guernsey, Belted Galloway, Gelbvieh, Hereford, Jersey, Limousin, Longhorn, Maine Anjou, MRI (Meuse-rhine-yssel), Murray Grey, Piedmontese, Romangola, Sahiwal, Santa Gertrudis, Scottish Highland, Shorthorn, South Devon, Sussex, Swedish Red, Simmental, Wagyu, Welsh Black, Angus, and Zebu.

All the polymorphisms discovered are listed in Table 1, above.

The majority of the primers are also listed in FIG. 2b or contained in the cDNA sequence (SEQ ID NO: 4).

Experimental Method for the OLA Analysis of Four SNP's in DGAT1

PCR Amplification of the Regions Containing the Polymorphisms

Protocol for the PCR amplification of exon VIII, intron XII and 3' UTR, the regions containing the four polymorphisms that were initially described in the DGAT1 gene.

| Component | For 1 sample | Final concentration |
|---|---|---|
| HotStar Qiagen Buffer (10 x) | 1.5 µl | 0.7 µM |
| Primer 17F at 100 µM | 0.07 µl | 0.7 µM |
| 18R at 10 µM | 0.07 µl | 0.5 µM |
| Primer 6F at 100 µM | 0.05 µl | 0.5 µM |
| AW 446985dn1 at 100 µM | 0.05 µl | 0.5 µM |
| Primer InsUp1 | 0.05 µl | 0.5 µM |
| 14R2 | 0.05 µl | 10% |
| DMSO | 1 µl | 300 µM |
| dNTP 10 mM | 0.3 µl | 0.1 U/µl |
| HotStarQiagen Taq (CatNr 203205: 5 U/µl) | 0.2 µl | |
| H2O | 1.66 µl | |
| DNA (5 ng/µl) | 5 µl | |
| Total | 10 µl | |

Primer sequences are given in the following table as well as the genomic region targeted by them.

PCR amplification was performed on MJ PTC100 or PTCT200 cyclers using the following steps:

| Step | Temperature | Time | Comment |
|---|---|---|---|
| 1° Activation of the enzyme | 94° C. | 12 minutes | One times |
| 2° Denaturation | 92° C. | 1 minute | Repeat step |
| 3° Hybridisation | 60° C. | 1 minute 30 seconds | 2 to 4, 35 |
| 4° Elongation | 72° C. | 1 minute 30 seconds | |
| 5° Inactivation of the enzyme | 99° C. | 45 minutes | |

Oligonucleotide Ligation Assay (OLA)

The oligonucleotides used in the OLA multiplex reaction are given in the table below.

The detection of each mutation relies on the use of two fluorescent-labelled oligonucleotide (SNPx_FAM and SNPx_HEX) and one common 3' and 5' phosphorylated, non-labelled oligonucleotide (SNPx_2P)

| SNP targeted | Primer name | Primer sequence | SEQ ID No: | 5' base position |
|---|---|---|---|---|
| Exon VIII SNP (DG 1) | 17F | CCTGAGCTTGCCTCTCCCACAGT | 48 | 6579 |
| | 18R | CCAGGAGTCGCCGCAGCAGGAAG | 49 | 7058 |
| Exon XII SNPs | 6F | CCGGCCATCCAGAACTCCATGAAG | 50 | 7280 |
| (DG 2 and DG3) | AW446985 dn1 | TAGAACTCGCGGTCTCCAAAC | 51 | 7605 |
| | InsUp1 | TGGCTGTCACTCATCATCGGGCA | 52 | 8222 |
| 3'UTR SNP (DG4) | 14R2 | TTGCACAGCACTTTATTGACACA | 53 | 8566 |

| Locus | Oligo | Sequence | SEQ ID NO: | 5' base position | Number of spacer phosphoramidites | Size of the ligation product[a] |
|---|---|---|---|---|---|---|
| DG1 | SNP1_FAM | AGC TTT GGC AGG TAA GGC | 54 | 6813 | | |
| | SNP1_HEX | AGC TTT GGC AGG TAA GAA | 55 | 6813 | | 32 |
| | SNP1_2P | GGC CAA CGG GGG AG | 56 | 6831 | 0 | |
| DG2 | SNP2_FAM | GCT GGC GGT GAG TGA | 57 | 7424 | | |
| | SNP2_HEX | GCT GGC GGT GAG TGG | 58 | 7424 | | 39 |
| | SNP2_2P | CCT GCT GGG TGG GGA | 59 | 7439 | 3 | |
| DG3 | SNP3_FAM | GCT GGG TGG GGA CGC | 60 | 7442 | | |
| | SNP3_HEX | GCT GGG TGG GGA CGT | 61 | 7442 | | 29 |
| | SNP3_P | GTG GGG GCG GGT GG | 62 | 7457 | 0 | |
| DG4 | SNP4_FAM | TGC CCC AAC CTG GGT | 63 | 8388 | | |
| | SNP4_HEX | TGC CCC AAC CTG GGC | 64 | 8388 | | 36 |
| | SNP4_2P | GCA GCA GGA GGA GGC | 65 | 8403 | 2 | |

[a] The size of the ligation products is the sum of the number of nucleotides of the two ligated oligonucleotides plus 3 bases equivalents per spacer phosphorazmdites molecule, present at the 5' end of the common oligonucleotide.

For each SNP a mixture of the three oligonucleotides was prepared first, following the dilution guidelines in the table below.

| SNP mixture | Oligonucleotide to mix | Quantity | Final concentration |
|---|---|---|---|
| DG1 (oligo. mixture) | SNP1__FAM 10 μM | 10 μl | 1 μM |
| | SNP1__HEX 10 μM | 20 μl | 2 μM |
| | SNP1__2P 10 μM | 20 μl | 2 μM |
| | H₂O | 50 μl | |
| DG2 (oligo. mixture) | SNP2__FAM 10 μM | 10 μl | 1 μM |
| | SNP2__HEX 10 μM | 20 μl | 2 μM |
| | SNP2__2P 10 μM | 20 μl | 2 μM |
| | H₂O | 50 μl | |
| DG3 (oligo. mixture) | SNP3__FAM 10 μM | 10 μl | 1 μM |
| | SNP3__HEX 10 μM | 20 μl | 2 μM |
| | SNP3__2P 10 μM | 20 μl | 2 μM |
| | H₂O | 50 μl | |
| DG4 (oligo. mixture) | SNP4__FAM 10 μM | 10 μl | 1 μM |
| | SNP4__HEX 10 μM | 30 μl | 3 μM |
| | SNP4__2P 10 μM | 20 μl | 2 μM |
| | H₂O | 40 μl | |

The ligation reaction for one sample was performed as follow:

| Component | Quantity per sample |
|---|---|
| DG1 oligonucleotide mixture$^a$ (35, 70 and 70 nM) | 0.7 μl |
| DG2 oligonucleotide mixture$^a$ (12.5, 25 and 25 nM) | 0.25 μl |
| DG3 oligonucleotide mixture$^a$ (12.5, 25 and 25 nM) | 0.25 μl |
| DG4 oligonucleotide mixture$^a$ (12.5, 37.5 and 25 nM) | 0.25 μl |
| DMSO | 2 μl |
| Incubation buffer of the Tsc DNA ligase (Roche, Cat Nr 1 939 807 or 1 939 815) | 2 μl |
| Tsc DNA ligase | 1 μl |
| H₂O | 8.55 μl |
| Multiplex PCR (see above) | 5 μl |
| Total | 20 μl |

$^a$The final concentration of the oligonucleotides in the ligation reaction is given between parenthesis (SNPx__FAM, SNPx__HEX and SNPx__2P respectively)

The sample was submitted to the following temperature cycling program in a MJ PTC100 or PTC 200 PCR machine.

| Step | Temperature | Time | Comment |
|---|---|---|---|
| 1° Initial denaturation step | 98° C. | 2 minutes | One times |
| 2° Denaturation | 94° C. | 30 seconds | Repeat step 2 to 3, 30 times |
| 3° Hybridisation and ligation | 45° C. | 3 minutes | |
| 5° Inactivation of the enzyme | 99° C. | 45 minutes | |

Following the LCR, 20 μl of H₂O was added to the ligation reaction. To 0.5 μl of the diluted ligation reaction, either 2 μl of loading buffer was added, or 2 μl loading buffer containing TAMRA350 internal line size standard.

The loading buffer was composed as follows: 1 part of blue dextran (50 mg/ml)/EDTA (25 mM) and 6 parts of formamide The TAMRA350 containing loading buffer was composed as follows: 3 parts TAMRA350 (Applied Biosystems 401736; 8 nM), 10 parts of Blue dextran (50 mg/ml)/EDTA (25 mM) and 60 parts of formamide.

TAMRA containing samples was placed alternately with TAMRA free samples when loaded onto the sequencing gel, in order to ease the identification of the lanes on the gel image.

The samples may require further dilution in order to avoid a too intense fluorescent signal on the sequencer. It is also very likely that from one primer batch to another, oligonucleotides concentrations will need adjustment.

The samples were denatured for 5 minutes at 95° C. before loading. The samples were then loaded onto a 6% denaturing acrylamide gel on sequencer ABI 373 or a 4% gel on sequencer ABI 377.

In addition to the OLA assays referred to above, genotyping of the DGAT1 polymorphism was carried out by utilizing two different techniques for detection of PCR products.

```
     Gel-based Genotyping Assay
Primer sequences 5' to 3', genomic sequence
    position within SEQ ID NO:1 brackets:

(SEQ ID NO:66)
DGAT1 21:    GTAGCTTTGGCAGGTAAGAA            (6811)

(SEQ ID NO:67)
DGAT1 22:    GGGGCGAAGAGGAAGTAGTA            (6984)

(SEQ ID NO:68)
DGAT1 23:    TGGCCCTGATGGTCTACACC            (6613)

(SEQ ID NO:69)
DGAT1 24B:   GGGCAGCTCCCCCGTTGGCGC           (6850)
```

The final reaction conditions were 1×Gold PCR buffer, 2.5mM MgCl₂ (Applied Biosystems), 200 μM each dNTP (Roche), 600 nM DGAT1 21 and DGAT1 22, 400 nM DGAT1 23 and DGAT1 24B (Invitrogen), 10% dimethylsulphoxide (Sigma), 3 μl DNA template and 2.5 units AmpliTaq Gold DNA polymerase (Applied Biosystems) in a total volume of 50 μl.

Cycling conditions were a 94° C. initial denaturation for 5 minutes, then 35 cycles of denaturation at 94° C. for 30 seconds, annealing at 56° C. for 30 seconds, extension at 72° C. for 20 seconds followed by one extension cycle of 72° C. for 2 minutes.

Primer positions around polymorphism (in bold) on genomic sequence from 6587 to 6986.

```
                    DGAT123    TGGC CCTGATGGTC TACACC
TGCCTCTCCC ACAGTGGGCT CCGTGCTGGC CCTGATGGTC TACACCATCC

TCTTCCTCAA GCTGTTCTCC TACCGGGACG TCAACCTCTG GTGCCGAGAG

CGCAGGGCTG GGGCCAAGGC CAAGGCTGGT GAGGGCTGCC TCGGGCTGGG

GCCACTGGGC TGCCACTTGC CTCGGGACCG GCAGGGGCTC GGCTCACCCC

DGAT1 21  GTAGCT TTGGCAGGTA AGAA
CGACCCGCCC CCTGCCGCTT GCTCGTAGCT TTGGCAGGTA AGAAGGCCAA
```

```
                       -continued
                  ←    CGCCGGTT
CGGGGGAGCT GCCCAGCGCA CCGTGAGCTA CCCCGACAAC CTGACCTACC
GCCCCCTCGA CGGG DGAT1 24B

GCGGTGAGGA TCCTGCCGGG GGCTGGGGGG ACTGCCCGGC GGCCTGGCCT

GCTAGCCCCG CCCTCCCTTC CAGATCTCTA CTACTTCCTC TTCGCCCCCA
(SEQ ID NO:70)
                  ←    AT GATGAAGGAG AAGCGGGG DGAT1 22
```

The Q allele has polymorphic sequence AA and is detected by the DGAT1 21+22 primers, producing a band of 174 bp. The q allele has polymorphic sequence GC and is detected by the DGAT123+24 primers, producing a band of 238 bp.

The primers DGAT123 and DGAT122 also successfully PCR the DGAT1 gene producing a product of 372 bp in all reactions. Therefore, a QQ homozygote would have bands at 372 bp and 174 bp, a qq homozygote would have bands at 372 bp and 238 bp and a Qq heterozygote would have all 3 bands at 372 bp, 238 bp and 174 bp.

18 µl of PCR product was separated on a 1.2% agarose TAE gel, stained with ethidium bromide and scored independently by two investigators on the basis of the number and size of bands present.

Both probes use MGB (minor groove binder) as a non-fluorescent quencher.

The final reaction conditions are 1× Universal PCR Mastermix (Applied Biosystems), 500 nM each primer (Invitrogen), 70 nM ForAA (FAM) probe, 300 nM DGAT1ADGC (VIC) probe (Applied Biosystems) and 2 µl of a 1/20 dilution of DNA template in a total volume of 10 µl.

Cycling conditions were 50° C. for 2 minutes, 95° C. initial denaturation for 10 minutes, then 37 cycles of denaturation at 94° C. for 15 seconds, annealing and extension 60° C. for 1 minute.

Primer positions around polymorphism (in bold) on genomic sequence from 6587 to 6986 of SEQ ID NO:1.

```
TGCCTCTCCC ACAGTGGGCT CCGTGCTGGC CCTGATGGTC TACACCATCC

DGAT1forAD TTCTCC TACCGGGACG TCAA
TCTTCCTCAA GCTGTTCTCC TACCGGGACG TCAACCTCTG GTGCCGAGAG

CGCAGGGCTG GGGCCAAGGC CAAGGCTGGT GAGGGCTGCC TCGGGCTGGG

GCCACTGGGC TGCCACTTGC CTCGGGACCG GCAGGGGCTC GGCTCACCCC

F rAA(FAM)A T TCTTCCGGTTGC
CGACCCGCCC CCTGCCGCTT GCTCGTAGCT TTGGCAGGTA AGAAGGCCAA
                                    DGAT1ADGC (VIC)CCAT TCCGCCGGTT

CGGGGGAGCT GCCCAGCGCA CCGTGAGCTA CCCCGACAAC CTGACCTACC
                                    ←        CTGTTG GACTGGATGG

GCGGTGAGGA TCCTGCCGGG GGCTGGGGGG ACTGCCCGGC GGCCTGGCCT
CGCC ReverseNZ

GCTAGCCCCG CCCTCCCTTC CAGATCTCTA CTACTTCCTC TTCGCCCCCA
(SEQ ID NO:75)
```

| TaqMan Allelic Discrimination Genotyping Assay | | |
|---|---|---|
| Primer sequences 5' to 3', genomic sequence position in brackets: | | |
| DGAT1forAD: | TTCTCCTACCGGGACGTCAA | (SEQ ID NO:71) (6651) |
| ReverseNZ: | CCGCGGTAGGTCAGGTTGTC | (SEQ ID NO:72) (6890) |
| Probe sequences 5' to 3', genomic sequence position in brackets: | | |
| ForAA (FAM): | CGTTGGCCTTCTTA | (SEQ ID NO:73) (6838) |
| DGAT1ADGC (VIC): | TTGGCCGCCTTACC | (SEQ ID NO:74) (6836) |

A 240 bp product is produced in this reaction. When the Q allele (AA) is present the FAM-labelled probe binds and fluoresces at 518 nm. When the q allele (GC) is present the VIC-labelled probe binds and fluoresces at 554 nm. After cycling is complete, the plate is scanned on the ABI7900 Sequence Detection System, the fluorescence from each well detected, and a scattergraph is drawn. The scattergraph separates out into 3 clumps with Q homozygotes in the upper left hand corner, q homozygotes in the lower right hand corner and Qq heterozygotes in between. Each clump is circled and the software automatically determines the genotype for each sample. On each plate there are controls with 8 wells each of known Q homozygotes, q homozygotes, Qq heterzygotes and no template controls.

Splice Variant Gene Expression

To determine the relative gene expression of the splice variants created by insertion/deletion of 66 bp around the polymorphic site by alternate exon usage, RNA was extracted from mammary tissue and reverse transcribed using oligodT primer using a first strand cDNA synthesis kit (Invitrogen). Real time PCR to determine relative quantities of each variant was then carried out.

```
Primer sequences 5' to 3',
genornic sequence position in brackets:

(SEQ ID NO:76)
DGAT1forRT66:      TCTCCTACCGGGACGTCAAC            (6652)

(SEQ ID NO:77)
DGAT1revRT66:      GAGATCGCGGTAGGTCAGGTT           (6964)

(SEQ ID NO:78)
DGAT1forRTless66:  GCTGCTTTGGCAGATCTCTACTACTT      (6711)

(SEQ ID NO:79)
DGAT1revRTless66:  AAGCGCTTTCGGATGCG              (7038)

Probe sequences 5' to 3',
genomic sequence position in brackets:

(SEQ ID NO:80)
DGAT1with66 (FAM): CCGTGAGCTACCC                   (6857)

(SEQ ID NO:81)
DGAT1less66 (VIC): CTTCGCCCCCACCCT                 (6976)
```

Both probes use MGB (minor groove binder) as a non-fluorescent quencher.

Final reaction conditions were 1×Universal PCR Mastermix (Applied Biosystems), 60 nM each primer (Invitrogen), 60 nM each probe (Applied Biosystems) and 1 µl of template cDNA in a total volume of 10 µl.

Cycling conditions were 50° C. for 2 minutes, 95° C. initial denaturation for 10 minutes, then 37 cycles of denaturation at 94° C. for 15 seconds, annealing and extension 60° C. for 1 minute.

Primer positions around 66 bp insertion (in italics) on cDNA sequence. The start of the cDNA sequence is equivalent to position 6479 on the genomic sequence, with the last base of the cDNA equivalent to position 7428 of the genomic sequence.

This reaction detects the presence of the insertion splice variant by creating a 145 bp product which binds the FAM probe only. The deletion splice variant is detected by a 92 bp product that binds the VIC probe only.

The cDNA for each alternate splice variant was cloned into pGemT (Promega). A dilution series of the same, known amount, of each variant plasmid DNA was used to create a standard curve that established the linearity of the PCR reaction over a range of DNA concentrations. The threshold cycle number of the sample variants was converted back to a DNA amount by linear regression and the amounts of each variant present compared.

The presence of an alternate spice variant raises the possibility of an alternate function that is at this stage unknown.

It will be appreciated that it is not intended to limit the invention to the above examples only, many variations, which may readily occur to a person skilled in the art, being possible without departing from the scope thereof as defined in the accompanying claims.

INDUSTRIAL APPLICATION

The present invention is directed to a method of genotyping bovine for improved milk production traits. In particular, such traits include increased milk volume and milk protein content and decreased milkfat content and solid fat content. It is anticipated that herds of bovine selected for such a trait will produce milk which will be more easily processed and such milk and products made therefrom may provide health benefits to consumers, as well as producing an increased milk yield.

REFERENCES

CASES, S.; SMITH, S. J.; ZHENG,Y-W.; MYERS, H. M.; LEAR, S. R.; SANDE, E.; NOVAK, S.; COLLINS, C.; WELCH, C. B.; LUSIS, A. J.; ERICKSON, S. K.; FARESE, R. V. JR (1998). Identification of a gene encoding an acyl CoA:diacylglycerol acyltransferase, a key enzyme in triacylglycerol synthesis. *Proceedings of the National Academy of Sciences, USA*. 95(22):13018-23.

COPPIETERS, W.; RIQUET, J.; ARRANZ, J.-J.; BERZI, P.; CAMBISANO, N.; GRISART, B.; KARIM, L.; MARCQ,

```
CCGTGGCCTT TCTCCTCGAG TCTATCACTC CAGTGGGCTC CGTGCTGGCC

DGAT1forRT66 TCTCCT ACCGGGACGT
CTGATGGTCT ACACCATCCT CTTCCTCAAG CTGTTCTCCT ACCGGGACGT CAAC→                               DGAT1forRTless66 GCTGCTT
CAACCTCTGG TGCCGAGAGC GCAGGGCTGG GGCCAAGGCC AAGGCTGCTT TGGCAG                    DGAT1with66(FAM) C CGTGAGCTAC
TGGCAGGTAA GAAGGCCAAC GGGGGAGCTG CCCAGCGCAC CGTGAGCTAC CC                        ATCTCTAC TACTT→
CCCGACAACC TGACCTACCG CGATCTCTAC TACTTCCTCT TCGCCCCCAC
    ←TTGG ACTGGATGGC GCTAGAGDGAT1revRT66 CT TCGCCCCCAC CCTGTGCTAC GAGCTCAACT TCCCCCGCTC CCCCCGCATC CGAAAGCGCT
CCT DGAT1less66 (VIC)         ←     GCGTAG GCTTTCGCGA TCCTGCTGCG GCGACTCCTG GAGATGCTGT TCCTCACCCA GCTCCAGGTG
A DGAT1revRTless66

GGGCTGATCC AGCAGTGGAT GGTCCCGGCC ATCCAGAACT CCATGAAGCC

CTTCAAGGAC ATGGACTACT CCCGCATCGT GGAGCGCCTC CTGAAGCTGG
(SEQ ID NO:82)
```

F.; SIMON, P.; VANMANSHOVEN, P.; WAGENAAR, D.;GEORGES, M. (1998) A QTL with major effect on milk yield and composition maps to bovine chromosome 14. *Mammalian Genome* 9: 540-544.

DELOUKAS et al (1998) A physical map of the 30,000 human genes. Science 282, 744-746

EWING, B.; HILLIER, L.; WENDL, M. C.; GREEN, P. (1998). Base-calling of automated sequencer traces using Phred. I. Accuracy assessment. *Genome Research* 8(3): 175-185.

EWING, B.; GREEN, P. (1998). Base-calling of automated sequencer traces using Phred. II. Error probabilities. *Genome Research* 8(3):186-194.

GORDON, D.; ABAJIAN, C.; GREEN, P. (1998). Consed: a graphical tool for sequence finishing. *Genome Research* 8(3): 195-202.

RIQUET, J.; COPPIETERS, W.; CAMBISANO, N.; ARRANZ, J.-J.; BERZI, P.; DAVIS, S.; GRISART, B.; FARNIR, F.; KARIM, L.; MNI, M.; SIMON, P.; TAYLOR, J.; VANMANSHOVEN, P.; WAGENAAR, D.; WOMACK, J. E.; GEORGES, M. (1999). Identity-by-descent fine-mapping of QTL in outbred populations: application to milk production in dairy cattle. *Proceedings of the National Academy of Sciences, USA* 96: 9252-9257.

FARNIR, F.; GRISART, B.; COPPIETERS, W.; RIQUET, J.; BERZI, P.; CAMBISANO, N.; KARIM, L.; MNI, M.; SIMON, P.; WAGENAAR, D.; GEORGES, M. (2000). Simultaneous mining of linkage and linkage disequilibrium to fine-map QTL in outbred half-sib pedigrees: revisiting the location of a QTL with major effect on milk production on bovine chromosome 14. *Ph.D Thesis, University of liege* 2000.

SMITH, S. J.; CASES, S.; JENSEN, D. R.; CHEN, H. C.; SANDE, E.; TOW, B.; SANAN, D. A.; RABER, J; ECKEL, R. H.; FARESE, R. V. JR (2000). Obesity resistance and multiple mechanisms of triglyceride synthesis in mice lacking DGAT. *Nature Genetics* 25(1):87-90.

BARENDSE, W.; ARMITAGE, S. M.; KOSSAREK, L. M.; SHALOM, A.; KIRKPATRICK, B. W.; RYAN, A. M.; CLAYTON, D.; U, L.; NEIBERGS, H. L.; ZHANG, N.; GROSSE, W. M.; WEISS, J.; CREIGHTON, P.; McCARTHY, F.; RON, M.; TEALE, A. J.; FRIES, R.; McGRAW, R. A.; MOORE, S. S.; GEORGES, M,; SOLLER, M.; WOMACK, J. E.; HETZEL, D. J. S. (1994). A genetic linkage map of the bovine genome. *Nature Genet.* 6: 227-235.

BISHOP, M. D.; KAPPES, S. M.; KEELE, J. W.; STONE, R. T.; SUNDEN, S. L. F.; HAWKINS, G. A.; SOLINAS TOLDO, S.; FRIES, R.; GROSZ, M. D.; YOO, J.; BEATTIE, C. W. (1994). A genetic linkage map for cattle. *Genetics* 136: 619-639.

COLLINS, F. S. (1995). Positional cloning moves from perditional to traditional. *Nature Genet.* 9: 347-350.

GEORGES, M.; ANDERSSON, L. (1996). Livestock genomics comes of age. *Genome Research* 6: 907-921.

GEORGES, M; NIELSEN, D.; MACKINNON, M.; MISHRA, A.; OKIMOTO, R.; PASQUINO, A. T.; SARGEANT, L. S.; SORENSEN, A.; STEELE, M. R.; ZHAO, X.; WOMACK, J. E.; HOESCHELE, I. (1995). Mapping quantitative trait loci controlling milk production by exploiting progeny testing. *Genetics* 139: 907-920.

HOUBENWCYL (1987). Methods of Organic Chemistry, ed. E. Wansch. Vol. 15 I and II. Thieme, Stuttgart.

HUSE et al. (1989). *Science* 246: 1275-1281.

KAPPES, S. M.; KEELE, J. W.; STONE, R. T.; McGRAW, R. A.; SONSTEGARD, T. S.; SMITH, T. P. L.; LOPEZ-CORRALES, N. L.; BEATTIE, C. W. (1997) A Second-Generation Linkage Map of the Bovine Genome. *Genome Research* 7: 235-249.

KOHLER and MILSTEIN (1975). *Nature*. 256: 495-497.

KOZBOR et aL (1983). *Immunol. Today* 4: 72.

MERRIFIELD (1964). *J. Am. Chem. Assoc.* 85: 2149-2154.

McCAFFERTY et al. (1990) *Nature* 348: 552-554.

SAMBROOK, J.; FRITSCH, E. F.; MANIATIS, T. (1989). *Molecular Cloning: A Laboratory Manual*. Cold Spring Harbour Lab Press, Cold Spring Harbour, N.Y.

STEWART, A. J.; CANITROT, Y.; BARACCHINI, E.; DEAN, N. M.; DEELEY, R. G. and COLE, S. P. C. (1996). Reduction of expression of the multidrug resistance protein (MRP) in human tumour cells by antisense phophorothioate oligonucleotudes. *Biochem Pharmacol.* 51: 461-469.

VAN RADEN, P. M., AND G. R. WIGGANS, 1991 Derivation, calculation, and use of National Animal Model Information. J. Dairy Sci. 74: 2737-2746.

JOHNSON, D. L.; THOMPSON, R. 1995. Restricted maximum likelihood estimation of variance components for univariate animal models using sparse matrix techniques and average information. *J. Dairy Sci.* 78: 449-456.

JOHNSON D. L., S. F. PETCH, A. M. WINKELMAN AND M. BRYANT 2000 Genetics of milk characteristics in New Zealand dairy cattle Proceedings of New Zealand Society of Animal Production 60:318-319.

MACGIBBON A. K. H. & MCLENNAN W. D. 1987. Hardness of New Zea-land patted butter: seasonal and regional variations. New Zealand Journal of Dairy Science and Technology, 22: 143-156.

FALCONER D. S. and MACKAY T. F. C. Introduction to Quantitative Genetics, 4th Edition. Longman Scientific and Technical, New York, 1996.

WELLER, J. I. et. al. Power of daughter and granddaughter designs for determining linkage between marker loci and quantitative trait loci in dairy cattle. *J. Dairy Sci.* 73, 2525-2537, (1990).

LYNCH M and WALSH B (1997). Genetics and analysis of quantitative traits. Sinuaer Associates, Inc. Sunderland, Mass.

SAS Institute Inc. 1985 SAS Users Guide: Statistics, Version 5 edition, Cary, N.C. 956p.

BOLDMAN K. G.; KRIESE L. A., VAN VLECK L. D.; VAN TASSELL C. P.; KACHMAN S. D. A manual for the use of MTDFREML, 1997, USDA-ARS.

SEQUENCE LISTING

```
<160> NUMBER OF SEQ ID NOS: 21

<210> SEQ ID NO 1
<211> LENGTH: 11771
<212> TYPE: DNA
<213> ORGANISM: Bos taurus
<220> FEATURE:
```

```
<221> NAME/KEY: CDS
<222> LOCATION: (1)..(191)
<223> OTHER INFORMATION: Exon 1 CDS, determined by alignment with an
      amino acid sequence deduced from the cDNA
<220> FEATURE:
<221> NAME/KEY: misc_signal
<222> LOCATION: (1)..(4)
<223> OTHER INFORMATION: these bases correspond to bases 4 to 7 of the
      Kozak recognition sequence. See DGAT1 cDNA for the complete
      recognition sequence.
<220> FEATURE:
<221> NAME/KEY: CDS
<222> LOCATION: (3809)..(3896)
<223> OTHER INFORMATION: Exon 2, determined by alignment with an amino
      acid sequence deduced from the cDNA
<220> FEATURE:
<221> NAME/KEY: CDS
<222> LOCATION: (5840)..(5880)
<223> OTHER INFORMATION: Exon 3, determined by alignment with an amino
      acid sequence deduced from the cDNA
<220> FEATURE:
<221> NAME/KEY: CDS
<222> LOCATION: (5960)..(6045)
<223> OTHER INFORMATION: Exon 4, determined by alignment with an amino
      acid sequence deduced from the cDNA
<220> FEATURE:
<221> NAME/KEY: CDS
<222> LOCATION: (6138)..(6190)
<223> OTHER INFORMATION: Exon 5, determined by alignment with an amino
      acid sequence deduced from the cDNA
<220> FEATURE:
<221> NAME/KEY: CDS
<222> LOCATION: (6406)..(6511)
<223> OTHER INFORMATION: Exon 6, determined by alignment with an amino
      acid sequence deduced from the cDNA
<220> FEATURE:
<221> NAME/KEY: CDS
<222> LOCATION: (6601)..(6714)
<223> OTHER INFORMATION: Exon 7, determined by alignment with an amino
      acid sequence deduced from the cDNA
<220> FEATURE:
<221> NAME/KEY: CDS
<222> LOCATION: (6815)..(6889)
<223> OTHER INFORMATION: Exon 8, determined by alignment with an amino
      acid sequence deduced from the cDNA
<220> FEATURE:
<221> NAME/KEY: variation
<222> LOCATION: (6824)..(6889)
<223> OTHER INFORMATION: this sequence is deleted from the alternately
      spliced transcript.
<220> FEATURE:
<221> NAME/KEY: CDS
<222> LOCATION: (6960)..(7063)
<223> OTHER INFORMATION: Exon 9, determined by alignment with an amino
      acid sequence deduced from the cDNA
<220> FEATURE:
<221> NAME/KEY: CDS
<222> LOCATION: (7154)..(7192)
<223> OTHER INFORMATION: Exon 10, determined by alignment with an amino
      acid sequence deduced from the cDNA
<220> FEATURE:
<221> NAME/KEY: CDS
<222> LOCATION: (7271)..(7312)
<223> OTHER INFORMATION: Exon 11, determined by alignment with an amino
      acid sequence deduced from the cDNA
<220> FEATURE:
<221> NAME/KEY: CDS
<222> LOCATION: (7386)..(7430)
<223> OTHER INFORMATION: Exon  12, determined by alignment with an amino
      acid sequence deduced from the cDNA
<220> FEATURE:
<221> NAME/KEY: CDS
<222> LOCATION: (7505)..(7617)
<223> OTHER INFORMATION: Exon 13, determined by alignment with an amino
      acid sequence deduced from the cDNA
<220> FEATURE:
<221> NAME/KEY: CDS
<222> LOCATION: (7705)..(7770)
<223> OTHER INFORMATION: Exon 14, determined by alignment with an amino
```

```
            acid sequence deduced from the cDNA
<220> FEATURE:
<221> NAME/KEY: CDS
<222> LOCATION: (7858)..(7945)
<223> OTHER INFORMATION: Exon 15, determined by alignment with an amino
            acid sequence deduced from the cDNA
<220> FEATURE:
<221> NAME/KEY: CDS
<222> LOCATION: (8027)..(8089)
<223> OTHER INFORMATION: Exon 16, determined by alignment with an amino
            acid sequence deduced from the cDNA
<220> FEATURE:
<221> NAME/KEY: CDS
<222> LOCATION: (8162)..(8314)
<223> OTHER INFORMATION: Exon 17 CDS, determined by alignment with an amino
            acid sequence deduced from the cDNA
<220> FEATURE:
<221> NAME/KEY: misc_feature
<222> LOCATION: (8315)..(8317)
<223> OTHER INFORMATION: translation stop codon
<220> FEATURE:
<221> NAME/KEY: polyA_site
<222> LOCATION: (8572)..(8578)
<223> OTHER INFORMATION:
<220> FEATURE:
<221> NAME/KEY: variation
<222> LOCATION: (626)..(626)
<223> OTHER INFORMATION: thymidine (T) to guanine (G) substitution
            polymorphism
<220> FEATURE:
<221> NAME/KEY: variation
<222> LOCATION: (3512)..(3512)
<223> OTHER INFORMATION: thymidine (T) to guanine (G) substitution
            polymorphism
<220> FEATURE:
<221> NAME/KEY: variation
<222> LOCATION: (4040)..(4040)
<223> OTHER INFORMATION: thymidine (T) to cytosine (G) substitution
            polymorphism
<220> FEATURE:
<221> NAME/KEY: variation
<222> LOCATION: (4963)..(4963)
<223> OTHER INFORMATION: adenine (A) to guanine (G) substitution
            polymorphism
<220> FEATURE:
<221> NAME/KEY: variation
<222> LOCATION: (5003)..(5003)
<223> OTHER INFORMATION: guanine (G) to adenine (A) substitution
            polymorphism
<220> FEATURE:
<221> NAME/KEY: variation
<222> LOCATION: (5997)..(5997)
<223> OTHER INFORMATION: cytosine (C) to thyamine (T) substitution
            polymorphism
<220> FEATURE:
<221> NAME/KEY: variation
<222> LOCATION: (6829)..(6830)
<223> OTHER INFORMATION: adenine (A)-adenine (A) to guanine(G)-cytosine
            (C) substitution polymorphism
            AA corresponds to the Q allele
            GC corresponds to the q allele
<220> FEATURE:
<221> NAME/KEY: variation
<222> LOCATION: (6892)..(6892)
<223> OTHER INFORMATION: guanine (G) to adenine (A) substitution
            polymorphism
<220> FEATURE:
<221> NAME/KEY: variation
<222> LOCATION: (7224)..(7225)
<223> OTHER INFORMATION: guanine (G)-guanine (G) to adenine (A)-cytosine
            (C) substitution  polymorphism GG-AC
<220> FEATURE:
<221> NAME/KEY: variation
<222> LOCATION: (7438)..(7438)
<223> OTHER INFORMATION: adenine (A) to guanine (G) substitution
            polymorphism
<220> FEATURE:
<221> NAME/KEY: variation
<222> LOCATION: (7456)..(7456)
```

```
<223> OTHER INFORMATION: cytosine (C) to thymidine (T) substitution
      polymorphism
<220> FEATURE:
<221> NAME/KEY: variation
<222> LOCATION: (7987)..(7987)
<223> OTHER INFORMATION: guanine (G) to adenine (A) substitution
      polymorphism
<220> FEATURE:
<221> NAME/KEY: variation
<222> LOCATION: (8402)..(8402)
<223> OTHER INFORMATION: ctosine (C) to thymidine (T) substitution
      polymorphism
<220> FEATURE:
<221> NAME/KEY: misc_feature
<222> LOCATION: (9434)..(9434)
<223> OTHER INFORMATION: ambiguous nucleotide
<220> FEATURE:
<221> NAME/KEY: misc_feature
<222> LOCATION: (9496)..(9496)
<223> OTHER INFORMATION: ambiguous nucleotide
<220> FEATURE:
<221> NAME/KEY: misc_feature
<222> LOCATION: (10402)..(10417)
<223> OTHER INFORMATION: ambiguous nucleotides
<220> FEATURE:
<221> NAME/KEY: primer_bind
<222> LOCATION: (6579)..(6601)
<223> OTHER INFORMATION: Primer 17F
      CCTGAGCTTGCCTCTCCCACAGT
<220> FEATURE:
<221> NAME/KEY: primer_bind
<222> LOCATION: (7036)..(7058)
<223> OTHER INFORMATION: Primer 18R
      CCAGGAGTCGCCGCAGCAGGAAG
      reverse primer
<220> FEATURE:
<221> NAME/KEY: primer_bind
<222> LOCATION: (7280)..(7303)
<223> OTHER INFORMATION: Primer 6F
      CCGGCCATCCAGAACTCCATGAAG
<220> FEATURE:
<221> NAME/KEY: primer_bind
<222> LOCATION: (7585)..(7605)
<223> OTHER INFORMATION: Primer AW446985  dn1
      TAGAACTCGCGGTCTCCAAAC
      reverse primer
<220> FEATURE:
<221> NAME/KEY: primer_bind
<222> LOCATION: (8222)..(8244)
<223> OTHER INFORMATION: Primer InsUp1
      TGGCTGTCACTCATCATCGGGCA
<220> FEATURE:
<221> NAME/KEY: primer_bind
<222> LOCATION: (8566)..(8589)
<223> OTHER INFORMATION: Primer 14R2
      TTGCACAGCACTTTATTGACACA
<220> FEATURE:
<221> NAME/KEY: primer_bind
<222> LOCATION: (6813)..(6830)
<223> OTHER INFORMATION: Primer SNP1_FAM
      AGC TTT GGC AGG TAA GGC
<220> FEATURE:
<221> NAME/KEY: primer_bind
<222> LOCATION: (6813)..(6830)
<223> OTHER INFORMATION: Primer SNP1_HEX
      AGC TTT GGC AGG TAA GAA
<220> FEATURE:
<221> NAME/KEY: primer_bind
<222> LOCATION: (6831)..(6844)
<223> OTHER INFORMATION: Primer SNP1_2P
      GGC CAA CGG GGG AG
<220> FEATURE:
<221> NAME/KEY: primer_bind
<222> LOCATION: (7424)..(7438)
<223> OTHER INFORMATION: Primer SNP2_FAM
      GCT GGC GGT GAG TGA
<220> FEATURE:
<221> NAME/KEY: primer_bind
<222> LOCATION: (7424)..(7438)
```

-continued

```
<223> OTHER INFORMATION: Primer SNP2_HEX
      GCT GGC GGT GAG TGG
<220> FEATURE:
<221> NAME/KEY: primer_bind
<222> LOCATION: (7439)..(7453)
<223> OTHER INFORMATION: Primer SNP2_2P
      CCT GCT GGG TGG GGA
<220> FEATURE:
<221> NAME/KEY: primer_bind
<222> LOCATION: (7442)..(7456)
<223> OTHER INFORMATION: Primer SNP3_FAM
      GCT GGG TGG GGA CGC
<220> FEATURE:
<221> NAME/KEY: primer_bind
<222> LOCATION: (7442)..(7456)
<223> OTHER INFORMATION: Primer SNP3_HEX
      GCT GGG TGG GGA CGT
<220> FEATURE:
<221> NAME/KEY: primer_bind
<222> LOCATION: (7457)..(7470)
<223> OTHER INFORMATION: Primer SNP3_P
      GTG GGG GCG GGT GG
<220> FEATURE:
<221> NAME/KEY: primer_bind
<222> LOCATION: (8388)..(8402)
<223> OTHER INFORMATION: Primer SNP4_FAM
      TGC CCC AAC CTG GGT
<220> FEATURE:
<221> NAME/KEY: primer_bind
<222> LOCATION: (8388)..(8402)
<223> OTHER INFORMATION: Primer SNP4_HEX
      TGC CCC AAC CTG GGC
<220> FEATURE:
<221> NAME/KEY: primer_bind
<222> LOCATION: (8403)..(8417)
<223> OTHER INFORMATION: Primer SNP4_2P
      GCA GCA GGA GGA GGC
<220> FEATURE:
<221> NAME/KEY: primer_bind
<222> LOCATION: (6811)..(6830)
<223> OTHER INFORMATION: Primer Dgat 21
      GTAGCTTTGGCAGGTAAGAA
<220> FEATURE:
<221> NAME/KEY: primer_bind
<222> LOCATION: (6965)..(6984)
<223> OTHER INFORMATION: Primer Dgat 22
      GGGGCGAAGAGGAAGTAGTA
      reverse primer
<220> FEATURE:
<221> NAME/KEY: primer_bind
<222> LOCATION: (6613)..(6632)
<223> OTHER INFORMATION: Primer Dgat 23
      TGGCCCTGATGGTCTACACC
<220> FEATURE:
<221> NAME/KEY: primer_bind
<222> LOCATION: (6829)..(6850)
<223> OTHER INFORMATION: Primer Dgat 24B
      GGGCAGCTCCCCCGTTGGCCGC
      reverse primer
<220> FEATURE:
<221> NAME/KEY: primer_bind
<222> LOCATION: (6651)..(6670)
<223> OTHER INFORMATION: Primer DgatforAD
      TTCTCCTACCGGGACGTCAA
<220> FEATURE:
<221> NAME/KEY: primer_bind
<222> LOCATION: (6871)..(6890)
<223> OTHER INFORMATION: Primer ReverseNZ
      CCGCGGTAGGTCAGGTTGTC
      reverse primer
<220> FEATURE:
<221> NAME/KEY: primer_bind
<222> LOCATION: (6825)..(6838)
<223> OTHER INFORMATION: Probe ForAA (FAM)
      CGTTGGCCTTCTTA
<220> FEATURE:
<221> NAME/KEY: primer_bind
<222> LOCATION: (6823)..(6836)
<223> OTHER INFORMATION: Probe DgatADGC (VIC)
```

```
            TTGGCCGCCTTACC
<220> FEATURE:
<221> NAME/KEY: primer_bind
<222> LOCATION: (6651)..(6670)
<223> OTHER INFORMATION: Primer DgatforAD
      TTCTCCTACCGGGACGTCAA
<220> FEATURE:
<221> NAME/KEY: primer_bind
<222> LOCATION: (6878)..(6972)
<223> OTHER INFORMATION: Primer DgatrevAD
      AAGTAGTAGAGATCGCGGTAGGTCA
      reverse primer
<220> FEATURE:
<221> NAME/KEY: primer_bind
<222> LOCATION: (6825)..(6838)
<223> OTHER INFORMATION: Probe ForAA (FAM)
      CGTTGGCCTTCTTA
<220> FEATURE:
<221> NAME/KEY: primer_bind
<222> LOCATION: (6823)..(6836)
<223> OTHER INFORMATION: Probe DgatADGC (VIC)
      TTGGCCGCCTTACC
<220> FEATURE:
<221> NAME/KEY: primer_bind
<222> LOCATION: (6652)..(6671)
<223> OTHER INFORMATION: Primer DgatforRT66
      TCTCCTACCGGGACGTCAAC
<220> FEATURE:
<221> NAME/KEY: primer_bind
<222> LOCATION: (6874)..(6964)
<223> OTHER INFORMATION: Primer DgatrevRT66
      GAGATCGCGGTAGGTCAGGTT
      reverse primer
<220> FEATURE:
<221> NAME/KEY: primer_bind
<222> LOCATION: (6711)..(6972)
<223> OTHER INFORMATION: Primer DgatforRTless66,
      GCTGCTTTGGCAGATCTCTACTACTT
      This primer was designed to selectively bind and amplify the cDNA
      splice variant. The corresponding binding site in this genomic s
      equence comprises bases 6711 to 6715, 6815 to 6823 and 6960 to 69
      72.
<220> FEATURE:
<221> NAME/KEY: primer_bind
<222> LOCATION: (7022)..(7038)
<223> OTHER INFORMATION: Primer DgatrevRTless66
      AAGCGCTTTCGGATGCG
      reverse primer
<220> FEATURE:
<221> NAME/KEY: primer_bind
<222> LOCATION: (6857)..(6870)
<223> OTHER INFORMATION: Probe Dgatwith66 (FAM)
      CCGTGAGCTACCC
<220> FEATURE:
<221> NAME/KEY: primer_bind
<222> LOCATION: (6976)..(6990)
<223> OTHER INFORMATION: Probe Dgatless66 (VIC)
      CTTCGCCCCCACCCT

<400> SEQUENCE: 1 atg ggc gac cgc ggc ggc gcg ggc ggc tcc cgg cgc cgg agg acg ggg        48
Met Gly Asp Arg Gly Gly Ala Gly Gly Ser Arg Arg Arg Arg Thr Gly
1               5                   10                  15 tcg cgg cct tcg atc cag ggc ggc agt ggg ccc gcg gca gcg gaa gag        96
Ser Arg Pro Ser Ile Gln Gly Gly Ser Gly Pro Ala Ala Ala Glu Glu
            20                  25                  30 gag gtg cgg gat gtg ggc gcc gga ggg gac gcg ccg gtc cgg gac aca       144
Glu Val Arg Asp Val Gly Ala Gly Gly Asp Ala Pro Val Arg Asp Thr
        35                  40                  45 gac aag gac gga gac gta gac gtg ggc agc ggc cac tgg gac ctg ag        191
Asp Lys Asp Gly Asp Val Asp Val Gly Ser Gly His Trp Asp Leu Arg
    50                  55                  60 gtagcggtgc gcgtgacccc taaccttga ccctgatac ggggcccctg cgacccaacc      251
```

```
tggtggccca ggcctgtcgg cggcagctcg ggctcgagtc cgagagtctg gcgcctggac    311
cttggtgcac agctgtgccc ctcgggcctc cacggggaaa cttagcggga ggttgggggc    371
ggagggtctc ctgcccggaa cacccaggta cgggggccga ggggagggca gcggctcaac    431
ttctagacgc cctccctctg ccttcctttg gtgggttctg aagctttccc agggtgagcc    491
cactacgcac agtgtcctct acctggaagg agatacaggg gtccttcctg agggctatga    551
ggggtgcctt gtgggttgat aaagctcccg ggggaggagg gtggaccggc ggagaacaga    611
ggcaggggca gtgctagggg atttctcatc cctcgcagac cctccagaga atggtcttca    671
caaaggtccc tcatccgtca cccggcgatt gactggccta ggatcctgct tattaccagc    731
acaaatggct gctctagggt caaagtgggt cctgtaatgg gaccctcacc cctggttggg    791
gtacagggga ggagttggaa gtgcgcacac ccacaggtgg gcgccctgct tagctgaagg    851
actgatggga aggagttggg ggagcaagct gcggctgaaa gggaggatct gacccacgtg    911
ggcatcagct aagtcctgct ggctgcctcc aggcgttccc tttgccatcc tccacgcccc    971
tcccccgggg cctgaccttc atcctggtca agggctctca gggctctggt tttgggatc    1031 agctccagag ctagaggtta tcaaggagga agtgggcaac aggtcagtca gcaaggattt   1091
gctatcttca ctgggtgctg tggggagggg agggacaagg gcagttgggg tgcaggcact   1151
gtccctgccc ttgggggggca cacagttcac ctgagagata agatagccgc agccctgaag   1211
agtgagagca aggtcaggc acagagttca ggatgacacc aggggagggt ggctctgtga   1271
ggggcactgg cttcctacag gccccaggtg gtcctgaggg ggcggctgca aaggccagga   1331
ggcccacagg cccctctgcc cactcctggg gaactggatt tggggtcact ttgtatgagg   1391
tgggggcggg taccagcttt gggccaagct gtcaccctgg atgggccatc acttgcctgc   1451
tctgtatagg ccagatggcc agaagctgct cctgtcctgt tgatggccca tcctcgaggt   1511
ctggaccctc gggaagagga gcagttggtg gcagggatgg gccaccggag accctcctga   1571
cctccaggac acgcagctgt gtgtgcctgt ccccaagcca catgccacat ggctaggggc   1631
ctcctggggc agggctgggc attggtctgg ctactcttgg tatcgcctat ggcttccctg   1691
cctcccagtc atcatcctcc cacctctgcc tccctgcctg ttcctctctt tctcctcagg   1751
cccttccgga catttcctgc tcacctaggt ctgggcaggc ggggtcaggt gccgggtgtg   1811
agctcactcc ttccggcagc aaggtgtagc tatgtgccgg aaggaaggcc gctgctgttg   1871 cctgcctct gagtgcatcc cttccaggtc ctccacactc cctgtgccc cgacacctgg   1931 tgcgtccttc agccattggt tcatgtgtcc tccaggcaca gctttctagt ccagagcctc   1991
taggctgggt gcaggaagtg ctgaggaagt ggcagccggg aggcgagctg gcaccctgtc   2051
cctccttgtt ctgtccgtcc ctgcccctgg accgtatggc cccgcatgtg tgatccccac   2111
ttggggctgt gcctctgggc aagttgggaa gcttggtgag cctcatttc atgtgcccgc    2171 ctcccagtac tgatgtgcag gttgaatgag gtgccaactg taatgagttg gaatggccct   2231
gctggctggg tgggactggg gagcaggtgg gggccgctgg ggggcacaga ggcacaccca   2291
gtgcctcagt caggggagagg gtgacagaga agctctgggt gaggccccac ctccactctg   2351
gccatggctg ctgccctttg gtccactgca gtgaactgtg ccatgggct ggacctctgt    2411 ggggattggt gggcagtggg ctttcttccc gcttggggcc tctgacctct gggggcaggg    2471
cgctgcccgg gtgggacagt cggaaggctg tagagggac ctgaggggtc tgtgtggtgg    2531
ctgggggcag gcctcaggaa tttgacagca gggatctgga aaagctttaa taacattatt   2591
```

```
tgttgtcagg attgggaaat gctcccctcc cccctccccc tctttcatct tagagactgc    2651
tgcacatctg gtcagtgtgg tcttcttggt ggccccccaag gtggcagggg tcacactgtt   2711
atgaaaccgt cccctgggta tgtggtgcag acatgcacat gcagatggtg attggcaggt   2771
tgtagcatga ggtggctttg ggacggttcc agtgacagtg agtgggctgg atctgggggg   2831
ttctgggcag gtccatcaag cggatacccc cacagactgt cctcttggga tagttgggcc   2891
tgggagccct gcttgccttg ccaaaaggca ggcgcagagt catgaagaag agggcttggg   2951
ggctcagagc cccactgtgt gtgcagccca gggtggacct ggaggaggtg cgtgggcagg   3011
ctgggccggc cggggcgggg ggtgggggg cctggtgtga aagggaccca gggccagact    3071
gtcagcgctg cctggctgag gatgctggca ccctgtcctc cccagccgtc tgtctcctgg   3131
gtgcagccat ctgagtgctg accccagccg ccctggagg ctggctgttc tcctgtgccc    3191
tattgctggg gacatgtgtc cacaggaggg aaagggaagc cccggcctct cccttacaa    3251
aactggaggc cttgctcaat gccctggatg gcctcctggt ggcagggtgg ttggtgggag   3311
gtggggctgc tgcttagaac ccgccagcgg gcctgggcct gggctgagct gcacccctcc   3371
acctctgcct ccagctgagg gttggcttcc atctccacca ggcccagcac tgggcacagg   3431
gctctcagag gcaggctctg aaagtcccct gctggcttct gcagtggact ccaggcgccg   3491
agccccaggg ggctcgcat tgcgctcacc ctgcgaagcc acgtgaaggc tgggtcctcc     3551
cctccggaag ggccaaatgc agggcatggg tggtttgaat ggtggcccct gggctccccg   3611
gagggaccag ctgctgtgag gccgccccc tccccacttc cgtcttgcat caccagctcc    3671
tgtggcactc cccacgcccc gtcccccagt gggagcggca ggccccggt ggctctgccc    3731
gcggaggggg atgtgtgggc ggcggggtgg ccttgctgcc agatgctctg ccccgagtgt   3791
ccgtctccgc tctccag g tgt cac cgc ctg cag gat tcc ctg ttc agt tct    3842
                   Cys His Arg Leu Gln Asp Ser Leu Phe Ser Ser
                                  65              70              75
gac agt ggc ttc agc aac tac cgt ggc atc ctg aat tgg tgt gtg gtg    3890
Asp Ser Gly Phe Ser Asn Tyr Arg Gly Ile Leu Asn Trp Cys Val Val
        80                  85                  90
atg ctg gtacgtagag tgcaccttg gagcaagggt cctgacggcc gggggccat       3946
Met Leu
gggctcttct ccaggggtag gtgtctgtac ttgtgtagct gtggtgaatg gagctctgtg   4006
ctggcggtgg gggtccctgg agcagccgta ccctgggacc ctaccgggag catgctcatg   4066
ccgtccctgc tgaatcccag gagatgcctg cagagggcag cctgggagcc tctgagctgg   4126
ggtctgcgcc ccaggggggca ctggagtctc ccaggggggc gagagagagt aggcagggat  4186
ggtctggtgg ccctggggtgg gggatggctg ctccgtgggc ccaggccctc cctggcagca  4246
caggtgagtg gtcttggggg tccacgtaga acttcctctt ctgttccaaa ttgccctcat   4306
gggtgcggca tgcctgggtg aacctggggg agcagggtga ggacatgctt ctcagcccag   4366
cccacagctc caggccacac tctgcaggac tctggcccct ccctcagccc tggagggagc   4426
aggactggag tcctgtgtcc gccttgctct gacctggccg aggccactgc tgtggggccc   4486
cagcaggcct gccagcaga aggtggagtg cagggacccc aggggcagcc ttcagggtgg    4546
ggcagggtga ggcccgactg ggcccagccc caccgctcag tgctgatgtg gcgcgaggcc   4606
ttcgcccctc cagctgacgt gtctgcctgc cctgggtgtg gctccagagg ctgcctgtgt   4666
accaggggcc cccacgcttc tgtttgtggt tctgggcagt cccctgggga gcggtggggg   4726
ctgtgtgcca gtccagaccc agtagtccac gcgtcctggt ctctggaggc cgtggctggt   4786
```

```
ccaggactgt ggcaaggtgg tcgtgcaggg caggccctca gcagcctgtc tgttctcctg   4846
cagcccccag cctcctggcc ctttggtgca cccacaaagc tccccccctcc cccaggagct   4906 ggggccgcct gctgcgtcct ctcggcagcc tgggcttcca ggtggctggg cctcttagca   4966
gctccaactc ttgcctgtgg tgggctctca ggacaggcaa ctgccagtcg gcagacattg   5026
caggaccacg tgtgtcctgg taagctggct ggttaggtgt ttagctgggg gatggtgtgg   5086
caggtggccc ctgcatctct gagcctgtca cctcctcggg aagccttctg ggtgggggac   5146
tccacccatg tcgcctggag aagcatcact tttccacaga gccttctgca accccgtgg    5206 ggcctgagcc tggggtgggg gaggtggtgg cccctgctcc tgcagaggcc agccaggcat   5266
ctggccccag ccactggca  agagctcgtt gtgttggggg atctgtcctt tgctgctgct   5326
gcaggagcgg ccgaggcagg cggggcgtg  agtaggggtg gagacccagg cccagcttcc   5386
ccagcccctc aggaccggcc tgctctttcc caccacccca ccaagtgcgt gggcacaccc   5446
cgcctgtgag gatgggcccg gttggcaggg cggagccctg ggagggtggc agtgcgccgg   5506
gcaggcttgg acttcactgg ggcttgggt  tgtcgctgtg gccaggggcg ctgacccgct   5566
tggtgggacg gacggccgct gggcagcagg tttcttctgc cacggtggca caggcacctg   5626
gggttgtggt tggctccagg cgggcggggg ctgcgtgccc ctgcgcaggc acataggccg   5686
tgggtgggga gtctcagagc ttggcgtgag gtcccacagg gctgggcctg caggatggag   5746
gccactgtcc tgagctgcag gtgctggcag gagctggggt gggcgttctg ggccgtggc   5806 tgacagcgtt atgtccctct ctctctatcg cag atc tta agc aac gca cgg tta   5860
                                     Ile Leu Ser Asn Ala Arg Leu
                                          95                100 ttt cta gag aac ctc atc aa  gtgagtgggc cccggcctgc cccagcccct          5910
Phe Leu Glu Asn Leu Ile Lys
        105 gccacctcac ccctcgccta cacagaccct cacccacctg cgtctgcag g tat ggc      5966
                                                       Tyr Gly atc ctg gtg gac ccc atc cag gtg gtg tct ctg ttc ctg aag gac ccc      6014
Ile Leu Val Asp Pro Ile Gln Val Val Ser Leu Phe Leu Lys Asp Pro
110             115                 120                 125 tac agc tgg cca gct ctg tgc ctg gtc att g gtgagctggg tgcccaggag      6065
Tyr Ser Trp Pro Ala Leu Cys Leu Val Ile
            130                 135 gcctcaggcc ggcggtgggt gggacagggc tgatctgggc ctgaacctgc cctgggttgc   6125
ttctgtcctc ag tg  gcc aat atc ttt gcc gtg gct gcg ttc cag gtg gag   6175
              Val Ala Asn Ile Phe Ala Val Ala Ala Phe Gln Val Glu
                        140                 145 aag cgc ctg gcc gtg gtaagcagtg ccctcacgcc ctccctgac ttgcctcaag      6230
Lys Arg Leu Ala Val
    150 gtccttacca gtcgggctta ggcgggcca  ccagctggtc ccactgtgct tcagggtttt    6290 gggcctttcg tggccttcct gagagggggct gcacctcagg cctggtggct cttcctcagg  6350 gaggtcctct gaccagggag gggggtccct ggctgacgct ctgctcccac ccag gga    6408
                                                             Gly gct ctg acg gag cag gcg ggg ctg ctg ctg cac ggg gtc aac ctg gcc     6456
Ala Leu Thr Glu Gln Ala Gly Leu Leu Leu His Gly Val Asn Leu Ala
155                 160                 165                 170 acc att ctc tgc ttc cca gcg gcc gtg gcc ttt ctc ctc gag tct atc     6504
Thr Ile Leu Cys Phe Pro Ala Ala Val Ala Phe Leu Leu Glu Ser Ile
        175                 180                 185 act cca g gtgggcccca ccccgccccc cgcccccgcc cacgctgtct cggccacggg   6561
Thr Pro
```

Thr Pro

| | |
|---|---|
| cagcgcgggg ggcgtggcct gagcttgcct ctcccacag tg ggc tcc gtg ctg<br>                                                                         Val Gly Ser Val Leu<br>                                                                                          190 | 6614 |
| gcc ctg atg gtc tac acc atc ctc ttc ctc aag ctg ttc tcc tac cgg<br>Ala Leu Met Val Tyr Thr Ile Leu Phe Leu Lys Leu Phe Ser Tyr Arg<br>    195                      200                    205 | 6662 |
| gac gtc aac ctc tgg tgc cga gag cgc agg gct ggg gcc aag gcc aag<br>Asp Val Asn Leu Trp Cys Arg Glu Arg Arg Ala Gly Ala Lys Ala Lys<br>210                  215                    220                  225 | 6710 |
| gct g gtgagggctg cctcgggctg gggccactgg gctgccactt gcctcgggac<br>Ala | 6764 |
| cggcaggggc tcggctcacc cccgacccgc ccctgccgc ttgctcgtag ct ttg<br>                                                                                 Ala Leu | 6819 |
| gca ggt aag aag gcc aac ggg gga gct gcc cag cgc acc gtg agc tac<br>Ala Gly Lys Lys Ala Asn Gly Gly Ala Ala Gln Arg Thr Val Ser Tyr<br>        230                    235                    240 | 6867 |
| ccc gac aac ctg acc tac cgc g gtgaggatcc tgccggggc tgggggact<br>Pro Asp Asn Leu Thr Tyr Arg<br>245                  250 | 6919 |
| gcccggcggc ctggcctgct agccccgccc tcccttccag at ctc tac tac ttc<br>                                                             Asp Leu Tyr Tyr Phe<br>                                                                      255 | 6973 |
| ctc ttc gcc ccc acc ctg tgc tac gag ctc aac ttc ccc cgc tcc ccc<br>Leu Phe Ala Pro Thr Leu Cys Tyr Glu Leu Asn Phe Pro Arg Ser Pro<br>        260                    265                    270 | 7021 |
| cgc atc cga aag cgc ttc ctg ctg cgg cga ctc ctg gag atg<br>Arg Ile Arg Lys Arg Phe Leu Leu Arg Arg Leu Leu Glu Met<br>    275                      280                    285 | 7063 |
| gtgaggcggg gcctcgcggg ccagggtggg cgggcctgcc ggcacccggc accgggctc | 7123 |
| agctcactgt ccgcttgctt ccttccccag ctg ttc ctc acc cag ctc cag gtg<br>                                                    Leu Phe Leu Thr Gln Leu Gln Val<br>                                                                     290 | 7177 |
| ggg ctg atc cag cag gtacgtgccc ggggggggg ggggggggg gggggggact<br>Gly Leu Ile Gln Gln<br>295 | 7232 |
| ctggggccgt tggggagctg actctgcgct ttttgcag tgg atg gtc ccg gcc atc<br>                                                         Trp Met Val Pro Ala Ile<br>                                                              300                    305 | 7288 |
| cag aac tcc atg aag ccc ttc aag gtgagcaggc aggcctggca gggtgggttc<br>Gln Asn Ser Met Lys Pro Phe Lys<br>                            310 | 7342 |
| cggggtcagg gctgagggag ccagctgtgc cctgtgccca cag gac atg gac tac<br>                                                            Asp Met Asp Tyr<br>                                                                     315 | 7397 |
| tcc cgc atc gtg gag cgc ctc ctg aag ctg gcg gtgagtgacc tgctgggtgg<br>Ser Arg Ile Val Glu Arg Leu Leu Lys Leu Ala<br>    320                      325 | 7450 |
| ggacgcgtgg gggcgggtgg ggctgttctg gcacctggca cccactcccc acag gtc<br>                                                                             Val | 7507 |
| ccc aac cac ctc atc tgg ctc atc ttc ttc tac tgg ctc ttc cac tcc<br>Pro Asn His Leu Ile Trp Leu Ile Phe Phe Tyr Trp Leu Phe His Ser<br>330                  335                    340                    345 | 7555 |
| tgc ctg aac gcc gtg gct gag ctc atg cag ttt gga gac gcc gag ttc<br>Cys Leu Asn Ala Val Ala Glu Leu Met Gln Phe Gly Asp Ala Glu Phe<br>        350                    355                    360 | 7603 |
| tac cgg gac tgg tg gtgggtggcc ttgccggggc ggggtggtg ggggcccccg<br>Tyr Arg Asp Trp Trp | 7657 |

```
                                           365
ctggggctgg ggccggagcc cctgcccact ctgccccgcc ccgcag g aac tcc gag        7714
                                                  Asn Ser Glu tcc atc acc tac ttc tgg cag aac tgg aac atc cct gtt cac aag tgg        7762
Ser Ile Thr Tyr Phe Trp Gln Asn Trp Asn Ile Pro Val His Lys Trp
370                 375                 380                 385 tgc atc ag  gtgggtgtgc gcctgggggc gggggttgg ggggtgggac                  7810
Cys Ile Arg ggggtcgcgt ggcccgggcg cccagcccac tgccgcctcc cccgcag a cac ttc tac      7867
                                                    His Phe Tyr
                                                            390 aag ccc atg ctc cgg cgg ggc agc agc aag tgg gca gcc agg acg gca        7915
Lys Pro Met Leu Arg Arg Gly Ser Ser Lys Trp Ala Ala Arg Thr Ala
                395                 400                 405 gtg ttt ctg gcc tcc gcc ttc ttc cac gag gtcagtgcac tgagggcgcg          7965
Val Phe Leu Ala Ser Ala Phe Phe His Glu
        410                 415 ccctgcccct ggtggggggtg gggtgggggg tggggggctcg ctgacgcccc tctcccctca     8025 g tac ctg gtg agc atc ccc ctg cgc atg ttc cgc ctc tgg gcc ttc acc       8074
  Tyr Leu Val Ser Ile Pro Leu Arg Met Phe Arg Leu Trp Ala Phe Thr
              420                 425                 430 ggc atg atg gcg cag gtgagcagcc ctggaccccc gctccgcccc gccccgcgag        8129
Gly Met Met Ala Gln
        435 cgcagaggct cactcccgtc ctgtgtcccc ag atc ccg ctg gcc tgg ata gtg         8182
                                   Ile Pro Leu Ala Trp Ile Val
                                                440             445 ggc cgc ttc ttc cgc ggc aac tac ggc aac gcg gcc gtg tgg ctg tca        8230
Gly Arg Phe Phe Arg Gly Asn Tyr Gly Asn Ala Ala Val Trp Leu Ser
                450                 455                 460 ctc atc atc ggg cag ccg gtg gcc gtc ctg atg tac gtc cac gac tac        8278
Leu Ile Ile Gly Gln Pro Val Ala Val Leu Met Tyr Val His Asp Tyr
            465                 470                 475 tac gtg ctc aac cgt gag gcg ccg gca gcc ggc acc tgagcgcctc             8324
Tyr Val Leu Asn Arg Glu Ala Pro Ala Ala Gly Thr
            480                 485 caggctggcc ccctcgtggg tgttggactg ctttgccgcg ctgcctgcgg ctggactaga      8384
gcctgcccca acctgggcgc agcaggagga ggcctggctg gtggaagctg cctcctggcc      8444
tccaccaggc ctctgcctga agggcttcct cctgccaggg gagagcaggc ccgacgcagt      8504
tctggcccct gggaggtgcc catgctctgg aaaccctaca gatctcgccc aagggtctga      8564
atgtgtcaat aaagtgctgt gcacagtgag ctccctcagc ctccagggca cagggctggc      8624
aggagggggc ggccctccca cgtggggcca tgctgtggga aggaggcccc agcgcctgga      8684
gaggagctgg ggctgtggtg accctccctg cctcacaggg ctctgtggtc agacgtcttg      8744
ccctgcaagg tggagactcc atgctccaag gcccctgtg cctgaggtct gcacacaagt       8804
ggattcaact tgggtcaggc cagaggctaa ggtgtggaag aaggttgaga atcaggctga      8864
cttgaacggc agcaaagact ccaaggcaag gctgcagaaa tctcaaaagc tatgcgcaca      8924
gtcccctgct ggggtgctca cctgggctgg gctctgggct gcttggacaa agcaggtggc      8984
ctggctcagc cctcaccgag ggccttcctt gggggcagag gttggcctga tgccaggggc      9044
tccccgtttt tccaggccct cagcaggtag ttgggtgtgg ccctcatgat accttggtcc      9104
cagagctccg ccactcaaaa agcttggcag tgaggcaagg gcaacccgg gctgttcccc       9164 cctctactgg ctctgccgcc tgggttggaa accctgaggc tgtgccaggc aggtgtaccc      9224
```

-continued

```
tgacagccag ccatggccca gtaagatggg tgcccgaggt ggtacctggg cagcggaccc     9284
agctgtgctg cccccgcccc aaccagaagc cgctctagcc catggtggtc gtctgggcga     9344
gacaggctgt tggctaggc actgtttggt ctacagcagg tgtaggcagc gtctccctga      9404
cccctgcctt ctaggaagcc accaccctgn gccctactca tcagcaagga cagcgagcag    9464
ggctgagctg ggggtgcgtg ggctgctacg gncccgcac cttcatcaca tgcacctctg     9524 cacccctgc tgcctgactc aagagtgggg gggggggtcc tgtgcttcct tcattccaga    9584
cccacggtgc tgacccagtg cacccacctg gtccgctagt gctgacctgg ccacagggct    9644
cctgtgggcc cacgctgatc ccgccctggt cccttcataa agaactcttg agcacatgca    9704
gcccagggga gccaggaggc tccagtgtgc tgtgtccatc tgcctccctt cagcccttc     9764 cgagacactg cgcatcatgc cccctccac ccccacccac actggcagga ggaacacaca    9824
gggagaccac acacagagct cgttgtttat aaatctctgc ctggctcatc ggtctgtttg    9884
tccatgtata tatctgcata tctctatgga aggggaaagg gggactcgtg taaaaatcca    9944
aaatacaatt ctatgaacac ctgcatcctg tcagtctga gtgtggccgt gaagcccagg     10004
tgagctgtgg ctcacagggc taggccctcg gtgctggccg ggggccactc cccacccct     10064 ctccccccct ccgccagcca ggggaccagg ctcctggaca ccaggcctgc ccaaggcctg    10124
ctctcctcct ggggcttcta cgagacagtg gggtccttgg ctttgggggg ttctgagccc    10184
gtcagcaggg agatggtggg gtcatctctt atatttcgtc tccctcggag aagtaggagc    10244
cctcccccag ctcgaagagc accggcaggt cgctgctccc cacgtccacg gagcccgggt    10304
ccaggagcag caggggctgg gcggtgtagt gcaccagctg cttccctagg ggtgcgactg    10364
ggtcagggtg ccggtggggc cggggggcgg ggtgggnnn nnnnnnnnn nnnccccccc     10424 cccggcccc agccacccg cctacgcacg ctggccaggc tgctgtccag gtcgggcagg      10484
ctcatgtcgg gcaccgtaac cgaggggctg aacagctgca gggaagaggg gcgggtcaga    10544
ctgccctgga agcggggcgg gctgggcgcg gggcgggcag ggttagactc acatccagca    10604
gggtgctggt gtccacgctg aagccatggc ttgtcagcat ggtctgcagg ttgtccaggt    10664
tggagtccat ggcgtccaag tggtcgctga gctcggtcct ggccagagga aggggagcag    10724
gtgacgtggc atccaggcac ccccaggtgc agtcctgccg gcccttaagc ccagctgcca    10784
gcctgccctg cgcaggctca cgggaggccc tgaggtgggg ccctgggcct gggacacttg    10844
gccaccggtg gtggctcagg ctccctcatc accgtgaggc cccgtaaggc agcacgtcag    10904
gctgggccgg ctaagacatc aggggggctga gttcagggct cagaagggcc cggggcccca    10964
gcttctcagg ttcagcaacg cctgcccttc acactggagg acagcaggag ggtggagctg    11024
tgctcggcca ggctgggcca gcctacccca gcatgcgcca ggatagatta ggcctgcccc    11084
ctcgaggagg ccaggcagta cctcggggtg ctgcctcagg ccccagaggt gggtggggag    11144
cctgttcaca ggctgggcag gggtctgctc agaggctggg gaggggccca agctctggcg    11204
gagccctcct ccctccccag tgggacagcg ctaaccctgg ctggactcgg ccatgcagag    11264
aggaggaggg gcagggaag aggcgggcga ccccagacat ctttggagtg cgagccaaac    11324
tgcaagatag aaagacaaga gccccctctc gcggtgggg cccagcgagt ccaagccccc     11384 cacccgttc acccacctct ggggtggtag acagacaga ccaggcggcc cggggagggc     11444
ggctcagggg gcaggggtgc ccgccacgtg cctggttccc acgttgcagg ggctgcggga    11504 cccctggct ggcatgtctc cctccccagc tccatgctct gggccaggtc ggccagtttc     11564
```

```
cccagcaaa tcccatgccg agggcctgag ggccatgcgt gtccagcccg gcactgtcct   11624
tgtcggaggc ccctgcgctt ccagagaccg aagggcgcct ggaaggcact cacttgtcta   11684
ggcaggcgac gctgaggcac ttctcgggag ccgaggcggg gagggtcgac ggatagcggc   11744
cccgagtgat ccgatagaag cttcgta                                      11771
```

```
<210> SEQ ID NO 2
<211> LENGTH: 489
<212> TYPE: PRT
<213> ORGANISM: Bos taurus
<220> FEATURE:
<221> NAME/KEY: misc_feature
<222> LOCATION: (8315)..(8317)
<223> OTHER INFORMATION: translation stop codon
<220> FEATURE:
<221> NAME/KEY: misc_feature
<222> LOCATION: (9434)..(9434)
<223> OTHER INFORMATION: ambiguous nucleotide
<220> FEATURE:
<221> NAME/KEY: misc_feature
<222> LOCATION: (9496)..(9496)
<223> OTHER INFORMATION: ambiguous nucleotide
<220> FEATURE:
<221> NAME/KEY: misc_feature
<222> LOCATION: (10402)..(10417)
<223> OTHER INFORMATION: ambiguous nucleotides

<400> SEQUENCE: 2
```

```
Met Gly Asp Arg Gly Gly Ala Gly Gly Ser Arg Arg Arg Thr Gly
1               5                   10                  15

Ser Arg Pro Ser Ile Gln Gly Gly Ser Gly Pro Ala Ala Ala Glu Glu
            20                  25                  30

Glu Val Arg Asp Val Gly Ala Gly Gly Asp Ala Pro Val Arg Asp Thr
        35                  40                  45

Asp Lys Asp Gly Asp Val Asp Val Gly Ser Gly His Trp Asp Leu Arg
    50                  55                  60

Cys His Arg Leu Gln Asp Ser Leu Phe Ser Ser Asp Ser Gly Phe Ser
65                  70                  75                  80

Asn Tyr Arg Gly Ile Leu Asn Trp Cys Val Val Met Leu Ile Leu Ser
                85                  90                  95

Asn Ala Arg Leu Phe Leu Glu Asn Leu Ile Lys Tyr Gly Ile Leu Val
            100                 105                 110

Asp Pro Ile Gln Val Val Ser Leu Phe Leu Lys Asp Pro Tyr Ser Trp
        115                 120                 125

Pro Ala Leu Cys Leu Val Ile Val Ala Asn Ile Phe Ala Val Ala Ala
    130                 135                 140

Phe Gln Val Glu Lys Arg Leu Ala Val Gly Ala Leu Thr Glu Gln Ala
145                 150                 155                 160

Gly Leu Leu Leu His Gly Val Asn Leu Ala Thr Ile Leu Cys Phe Pro
                165                 170                 175

Ala Ala Val Ala Phe Leu Leu Glu Ser Ile Thr Pro Val Gly Ser Val
            180                 185                 190

Leu Ala Leu Met Val Tyr Thr Ile Leu Phe Leu Lys Leu Phe Ser Tyr
        195                 200                 205

Arg Asp Val Asn Leu Trp Cys Arg Glu Arg Ala Gly Ala Lys Ala
    210                 215                 220

Lys Ala Ala Leu Ala Gly Lys Lys Ala Asn Gly Gly Ala Ala Gln Arg
225                 230                 235                 240

Thr Val Ser Tyr Pro Asp Asn Leu Thr Tyr Arg Asp Leu Tyr Tyr Phe
                245                 250                 255
```

Leu Phe Ala Pro Thr Leu Cys Tyr Glu Leu Asn Phe Pro Arg Ser Pro
            260                 265                 270

Arg Ile Arg Lys Arg Phe Leu Arg Arg Leu Leu Glu Met Leu Phe
        275                 280                 285

Leu Thr Gln Leu Gln Val Gly Leu Ile Gln Gln Trp Met Val Pro Ala
        290                 295                 300

Ile Gln Asn Ser Met Lys Pro Phe Lys Asp Met Asp Tyr Ser Arg Ile
305                 310                 315                 320

Val Glu Arg Leu Leu Lys Leu Ala Val Pro Asn His Leu Ile Trp Leu
                325                 330                 335

Ile Phe Phe Tyr Trp Leu Phe His Ser Cys Leu Asn Ala Val Ala Glu
                340                 345                 350

Leu Met Gln Phe Gly Asp Arg Glu Phe Tyr Arg Asp Trp Trp Asn Ser
        355                 360                 365

Glu Ser Ile Thr Tyr Phe Trp Gln Asn Trp Asn Ile Pro Val His Lys
        370                 375                 380

Trp Cys Ile Arg His Phe Tyr Lys Pro Met Leu Arg Arg Gly Ser Ser
385                 390                 395                 400

Lys Trp Ala Ala Arg Thr Ala Val Phe Leu Ala Ser Ala Phe Phe His
                405                 410                 415

Glu Tyr Leu Val Ser Ile Pro Leu Arg Met Phe Arg Leu Trp Ala Phe
                420                 425                 430

Thr Gly Met Met Ala Gln Ile Pro Leu Ala Trp Ile Val Gly Arg Phe
        435                 440                 445

Phe Arg Gly Asn Tyr Gly Asn Ala Ala Val Trp Leu Ser Leu Ile Ile
450                 455                 460

Gly Gln Pro Val Ala Val Leu Met Tyr Val His Asp Tyr Tyr Val Leu
465                 470                 475                 480

Asn Arg Glu Ala Pro Ala Ala Gly Thr
                485

<210> SEQ ID NO 3
<211> LENGTH: 31
<212> TYPE: DNA
<213> ORGANISM: Bos taurus
<220> FEATURE:
<221> NAME/KEY: misc_signal
<222> LOCATION: (29)..(31)
<223> OTHER INFORMATION: bases 1 to 3 of the Kozak recognition
      sequence. See the genomic sequence from the start codon for bases
      4 to 7 of the Kozak recognition sequence or the DGAT1 cDNA for the
      complete recognition sequence.

<400> SEQUENCE: 3
acttggccgc ggcggggtgc gaactaaggc c                                      31

<210> SEQ ID NO 4
<211> LENGTH: 1732
<212> TYPE: DNA
<213> ORGANISM: Bos taurus
<220> FEATURE:
<221> NAME/KEY: misc_feature
<222> LOCATION: (1)..(3)
<223> OTHER INFORMATION: translation start codon
<220> FEATURE:
<221> NAME/KEY: misc_feature
<222> LOCATION: (1468)..(1470)
<223> OTHER INFORMATION: translation stop codon
<220> FEATURE:
<221> NAME/KEY: variation
<222> LOCATION: (689)..(755)

```
<223> OTHER INFORMATION: this sequence is deleted in the alternately
      spliced transcript
<220> FEATURE:
<221> NAME/KEY: variation
<222> LOCATION: (358)..(358)
<223> OTHER INFORMATION: cytosine (C) to thyamine (T) substitution
      polymorphism
<220> FEATURE:
<221> NAME/KEY: variation
<222> LOCATION: (694)..(695)
<223> OTHER INFORMATION: adenine (A)-adenine (A) to guanine(G)-cytosine
      (C) substitution polymorphism AA corresponds to the Q allele
      GC corresponds to the q allele
<220> FEATURE:
<221> NAME/KEY: primer_bind
<222> LOCATION: (616)..(635)
<223> OTHER INFORMATION: Primer DgatforAD
      TTCTCCTACCGGGACGTCAA
<220> FEATURE:
<221> NAME/KEY: primer_bind
<222> LOCATION: (743)..(767)
<223> OTHER INFORMATION: Primer DgatrevAD
      AAGTAGTAGAGATCGCGGTAGGTCA
      reverse primer
<220> FEATURE:
<221> NAME/KEY: primer_bind
<222> LOCATION: (690)..(703)
<223> OTHER INFORMATION: Primer ForAA (FAM)
      CGTTGGCCTTCTTA
      reverse primer
<220> FEATURE:
<221> NAME/KEY: primer_bind
<222> LOCATION: (688)..(709)
<223> OTHER INFORMATION: Primer DgatADGC (VIC)
      TTGGCCGCCTTACC
      reverse primer
<220> FEATURE:
<221> NAME/KEY: primer_bind
<222> LOCATION: (617)..(636)
<223> OTHER INFORMATION: Primer DgatforRT66
      TCTCCTACCGGGACGTCAAC
<220> FEATURE:
<221> NAME/KEY: primer_bind
<222> LOCATION: (739)..(760)
<223> OTHER INFORMATION: Primer DgatrevRT66
      GAGATCGCGGTAGGTCAGGTT
      reverse primer
<220> FEATURE:
<221> NAME/KEY: primer_bind
<222> LOCATION: (676)..(767)
<223> OTHER INFORMATION: Primer DgatforRTless66
      GCTGCTTTGGCAGATCTCTACTACTT
      This primer selectively binds and amplifies a contigious sequence
      characteristic of the splice variant & generated by the deletion
      bases 689 to 755 of this sequence.
<220> FEATURE:
<221> NAME/KEY: primer_bind
<222> LOCATION: (817)..(833)
<223> OTHER INFORMATION: Primer DgatrevRTless66
      AAGCGCTTTCGGATGCG
<220> FEATURE:
<221> NAME/KEY: primer_bind
<222> LOCATION: (722)..(734)
<223> OTHER INFORMATION: Primer Dgatwith66 (FAM)
      CCGTGAGCTACCC
<220> FEATURE:
<221> NAME/KEY: primer_bind
<222> LOCATION: (771)..(785)
<223> OTHER INFORMATION: Primer Dgatless66 (VIC)
      CTTCGCCCCCACCCT

<400> SEQUENCE: 4
atgggcgacc gcggcggcgc gggcggctcc cggcgccgga ggacggggtc gcggccttcg      60
atccagggcg gcagtgggcc cgcggcagcg gaagaggagg tgcgggatgt gggcgccgga     120
ggggacgcgc cggtccggga cacagacaag gacggagacg tagacgtggg cagcggccac     180
```

-continued

```
tgggacctga ggtgtcaccg cctgcaggat tccctgttca gttctgacag tggcttcagc    240
aactaccgtg gcatcctgaa ttggtgtgtg gtgatgctga tcttaagcaa cgcacggtta    300
tttctagaga acctcatcaa gtatggcatc ctggtggacc ccatccaggt ggtgtctctg    360
ttcctgaagg accccctacag ctggccagct ctgtgcctgg tcattgtggc caatatcttt    420
gccgtggctg cgttccaggt ggagaagcgc ctggccgtgg agctctgac ggagcaggcg     480
gggctgctgc tgcacggggt caacctggcc accattctct gcttcccagc ggccgtggcc    540
tttctcctcg agtctatcac tccagtgggc tccgtgctgg ccctgatggt ctacaccatc    600
ctcttcctca agctgttctc ctaccggac gtcaacctct ggtgccgaga gcgcagggct     660
ggggccaagg ccaaggctgc tttggcaggt aagaaggcca acgggggagc tgcccagcgc    720
accgtgagct accccgacaa cctgacctac cgcgatctct actacttcct cttcgccccc    780
accctgtgct acgagctcaa cttccccgc tccccccgca tccgaaagcg cttcctgctg     840
cggcgactcc tggagatgct gttcctcacc cagctccagg tggggctgat ccagcagtgg    900
atggtcccgg ccatccagaa ctccatgaag cccttcaagg acatggacta ctcccgcatc    960
gtggagcgcc tcctgaagct ggcggtcccc aaccacctca tctggctcat cttcttctac   1020
tggctcttcc actcctgcct gaacgccgtg gctgagctca tgcagtttgg agaccgcgag   1080
ttctaccggg actggtggaa ctccgagtcc atcacctact tctggcagaa ctggaacatc   1140
cctgttcaca gtggtgcat cagacacttc tacaagccca tgctccggcg gggcagcagc    1200
aagtgggcag ccaggacggc agtgtttctg gcctccgcct tcttccacga gtacctggtg   1260
agcatccccc tgcgcatgtt ccgcctctgg gccttcaccg gcatgatggc gcagatcccg   1320
ctggcctgga tagtgggccg cttcttccgc ggcaactacg gcaacgcggc cgtgtggctg   1380
tcactcatca tcgggcagcc ggtggccgtc ctgatgtacg tccacgacta ctacgtgctc   1440
aaccgtgagg cgccggcagc cggcacctga gcgcctccag gctggccccc tcgtgggtgt   1500
tggactgctt tgccgcgctg cctgcggctg gactagagcc tgcccccaacc tgggcgcagc   1560
aggaggaggc ctggctggtg gaagctgcct cctggcctcc accaggcctc tgcctgaagg   1620
gcttcctcct gccaggggag agcaggcccg acgcagttct ggcccctggg aggtgcccat   1680
gctctggaaa ccctacagat ctcgcccaag ggtctgaatg tgtcaataaa ga           1732
```

<210> SEQ ID NO 5
<211> LENGTH: 489
<212> TYPE: PRT
<213> ORGANISM: Bos taurus
<220> FEATURE:
<221> NAME/KEY: VARIANT
<222> LOCATION: (232)..(232)
<223> OTHER INFORMATION: an amino acid substitution (K -> A) caused by a polymorphism at bases 7224-7225 of the genomic sequence (measured from the adenine residue of the translation start codon). Lysine (K) corresponds to the Q allele, alanine (A) corresponds to the q allele.

<400> SEQUENCE: 5

Met Gly Asp Arg Gly Gly Ala Gly Gly Ser Arg Arg Arg Thr Gly
1               5                   10                  15

Ser Arg Pro Ser Ile Gln Gly Gly Ser Gly Pro Ala Ala Ala Glu Glu
            20                  25                  30

Glu Val Arg Asp Val Gly Ala Gly Gly Asp Ala Pro Val Arg Asp Thr
        35                  40                  45

Asp Lys Asp Gly Asp Val Asp Val Gly Ser Gly His Trp Asp Leu Arg
    50                  55                  60

```
Cys His Arg Leu Gln Asp Ser Leu Phe Ser Ser Asp Ser Gly Phe Ser
 65                  70                  75                  80

Asn Tyr Arg Gly Ile Leu Asn Trp Cys Val Val Met Leu Ile Leu Ser
                 85                  90                  95

Asn Ala Arg Leu Phe Leu Glu Asn Leu Ile Lys Tyr Gly Ile Leu Val
            100                 105                 110

Asp Pro Ile Gln Val Val Ser Leu Phe Leu Lys Asp Pro Tyr Ser Trp
        115                 120                 125

Pro Ala Leu Cys Leu Val Ile Val Ala Asn Ile Phe Ala Val Ala Ala
    130                 135                 140

Phe Gln Val Glu Lys Arg Leu Ala Val Gly Ala Leu Thr Glu Gln Ala
145                 150                 155                 160

Gly Leu Leu Leu His Gly Val Asn Leu Ala Thr Ile Leu Cys Phe Pro
                165                 170                 175

Ala Ala Val Ala Phe Leu Leu Glu Ser Ile Thr Pro Val Gly Ser Val
            180                 185                 190

Leu Ala Leu Met Val Tyr Thr Ile Leu Phe Leu Lys Leu Phe Ser Tyr
        195                 200                 205

Arg Asp Val Asn Leu Trp Cys Arg Glu Arg Arg Ala Gly Ala Lys Ala
    210                 215                 220

Lys Ala Ala Leu Ala Gly Lys Lys Ala Asn Gly Gly Ala Ala Gln Arg
225                 230                 235                 240

Thr Val Ser Tyr Pro Asp Asn Leu Thr Tyr Arg Asp Leu Tyr Tyr Phe
                245                 250                 255

Leu Phe Ala Pro Thr Leu Cys Tyr Glu Leu Asn Phe Pro Arg Ser Pro
            260                 265                 270

Arg Ile Arg Lys Arg Phe Leu Leu Arg Arg Leu Leu Glu Met Leu Phe
        275                 280                 285

Leu Thr Gln Leu Gln Val Gly Leu Ile Gln Gln Trp Met Val Pro Ala
    290                 295                 300

Ile Gln Asn Ser Met Lys Pro Phe Lys Asp Met Asp Tyr Ser Arg Ile
305                 310                 315                 320

Val Glu Arg Leu Leu Lys Leu Ala Val Pro Asn His Leu Ile Trp Leu
                325                 330                 335

Ile Phe Phe Tyr Trp Leu Phe His Ser Cys Leu Asn Ala Val Ala Glu
            340                 345                 350

Leu Met Gln Phe Gly Asp Arg Glu Phe Tyr Arg Asp Trp Trp Asn Ser
        355                 360                 365

Glu Ser Ile Thr Tyr Phe Trp Gln Asn Trp Asn Ile Pro Val His Lys
    370                 375                 380

Trp Cys Ile Arg His Phe Tyr Lys Pro Met Leu Arg Arg Gly Ser Ser
385                 390                 395                 400

Lys Trp Ala Ala Arg Thr Ala Val Phe Leu Ala Ser Ala Phe Phe His
                405                 410                 415

Glu Tyr Leu Val Ser Ile Pro Leu Arg Met Phe Arg Leu Trp Ala Phe
            420                 425                 430

Thr Gly Met Met Ala Gln Ile Pro Leu Ala Trp Ile Val Gly Arg Phe
        435                 440                 445

Phe Arg Gly Asn Tyr Gly Asn Ala Ala Val Trp Leu Ser Leu Ile Ile
    450                 455                 460

Gly Gln Pro Val Ala Val Leu Met Tyr Val His Asp Tyr Tyr Val Leu
465                 470                 475                 480
```

Asn Arg Glu Ala Pro Ala Ala Gly Thr
                485

<210> SEQ ID NO 6
<211> LENGTH: 467
<212> TYPE: PRT
<213> ORGANISM: Bos taurus

<400> SEQUENCE: 6

Met Gly Asp Arg Gly Gly Ala Gly Gly Ser Arg Arg Arg Thr Gly
1               5                   10                  15

Ser Arg Pro Ser Ile Gln Gly Gly Ser Gly Pro Ala Ala Ala Glu Glu
                20                  25                  30

Glu Val Arg Asp Val Gly Ala Gly Gly Asp Ala Pro Val Arg Asp Thr
            35                  40                  45

Asp Lys Asp Gly Asp Val Asp Val Gly Ser Gly His Trp Asp Leu Arg
    50                  55                  60

Cys His Arg Leu Gln Asp Ser Leu Phe Ser Ser Asp Ser Gly Phe Ser
65                  70                  75                  80

Asn Tyr Arg Gly Ile Leu Asn Trp Cys Val Val Met Leu Ile Leu Ser
                85                  90                  95

Asn Ala Arg Leu Phe Leu Glu Asn Leu Ile Lys Tyr Gly Ile Leu Val
                100                 105                 110

Asp Pro Ile Gln Val Val Ser Leu Phe Leu Lys Asp Pro Tyr Ser Trp
            115                 120                 125

Pro Ala Leu Cys Leu Val Ile Val Ala Asn Ile Phe Ala Val Ala Ala
    130                 135                 140

Phe Gln Val Glu Lys Arg Leu Ala Val Gly Ala Leu Thr Glu Gln Ala
145                 150                 155                 160

Gly Leu Leu Leu His Gly Val Asn Leu Ala Thr Ile Leu Cys Phe Pro
                165                 170                 175

Ala Ala Val Ala Phe Leu Leu Glu Ser Ile Thr Pro Val Gly Ser Val
                180                 185                 190

Leu Ala Leu Met Val Tyr Thr Ile Leu Phe Leu Lys Leu Phe Ser Tyr
            195                 200                 205

Arg Asp Val Asn Leu Trp Cys Arg Glu Arg Arg Ala Gly Ala Lys Ala
    210                 215                 220

Lys Ala Ala Leu Ala Asp Leu Tyr Tyr Phe Leu Phe Ala Pro Thr Leu
225                 230                 235                 240

Cys Tyr Glu Leu Asn Phe Pro Arg Ser Pro Arg Ile Arg Lys Arg Phe
                245                 250                 255

Leu Leu Arg Arg Leu Leu Glu Met Leu Phe Leu Thr Gln Leu Gln Val
                260                 265                 270

Gly Leu Ile Gln Gln Trp Met Val Pro Ala Ile Gln Asn Ser Met Lys
            275                 280                 285

Pro Phe Lys Asp Met Asp Tyr Ser Arg Ile Val Glu Arg Leu Leu Lys
    290                 295                 300

Leu Ala Val Pro Asn His Leu Ile Trp Leu Ile Phe Phe Tyr Trp Leu
305                 310                 315                 320

Phe His Ser Cys Leu Asn Ala Val Ala Glu Leu Met Gln Phe Gly Asp
                325                 330                 335

Arg Glu Phe Tyr Arg Asp Trp Trp Asn Ser Glu Ser Ile Thr Tyr Phe
                340                 345                 350

Trp Gln Asn Trp Asn Ile Pro Val His Lys Trp Cys Ile Arg His Phe
            355                 360                 365

Tyr Lys Pro Met Leu Arg Arg Gly Ser Ser Lys Trp Ala Ala Arg Thr
    370                 375                 380

Ala Val Phe Leu Ala Ser Ala Phe Phe His Glu Tyr Leu Val Ser Ile
385                 390                 395                 400

Pro Leu Arg Met Phe Arg Leu Trp Ala Phe Thr Gly Met Met Ala Gln
                405                 410                 415

Ile Pro Leu Ala Trp Ile Val Gly Arg Phe Phe Arg Gly Asn Tyr Gly
            420                 425                 430

Asn Ala Ala Val Trp Leu Ser Leu Ile Ile Gly Gln Pro Val Ala Val
        435                 440                 445

Leu Met Tyr Val His Asp Tyr Tyr Val Leu Asn Arg Glu Ala Pro Ala
    450                 455                 460

Ala Gly Thr
465

<210> SEQ ID NO 7
<211> LENGTH: 12
<212> TYPE: DNA
<213> ORGANISM: Bos taurus
<220> FEATURE:
<221> NAME/KEY: variation
<222> LOCATION: (7)..(7)
<223> OTHER INFORMATION: thymidine (T) to guanine (G) substitution
      polymorphism

<400> SEQUENCE: 7
cagtgctagg gg                                                          12

<210> SEQ ID NO 8
<211> LENGTH: 10
<212> TYPE: DNA
<213> ORGANISM: Bos taurus
<220> FEATURE:
<221> NAME/KEY: variation
<222> LOCATION: (6)..(6)
<223> OTHER INFORMATION: thymidine (T) to guanine (G) substitution
      polymorphism

<400> SEQUENCE: 8
gcattgcgct                                                             10

<210> SEQ ID NO 9
<211> LENGTH: 11
<212> TYPE: DNA
<213> ORGANISM: Bos taurus
<220> FEATURE:
<221> NAME/KEY: variation
<222> LOCATION: (6)..(6)
<223> OTHER INFORMATION: thymidine (T) to cytosine (G) substitution
      polymorphism

<400> SEQUENCE: 9
taccctggga c                                                           11

<210> SEQ ID NO 10
<211> LENGTH: 11
<212> TYPE: DNA
<213> ORGANISM: Bos taurus
<220> FEATURE:
<221> NAME/KEY: variation
<222> LOCATION: (6)..(6)
<223> OTHER INFORMATION: adenine (A) to guanine (G) substitution
      polymorphism
<220> FEATURE:
<221> NAME/KEY: variation -continued

```
<222> LOCATION: (6)..(6)
<223> OTHER INFORMATION: adenine (A) to guanine (G) substitution
      polymorphism

<400> SEQUENCE: 10
ctcttagcag c                                                              11

<210> SEQ ID NO 11
<211> LENGTH: 10
<212> TYPE: DNA
<213> ORGANISM: Bos taurus
<220> FEATURE:
<221> NAME/KEY: variation
<222> LOCATION: (5)..(5)
<223> OTHER INFORMATION: guanine (G) to adenine (A) substitution
      polymorphism

<400> SEQUENCE: 11
acaggcaact                                                                10

<210> SEQ ID NO 12
<211> LENGTH: 11
<212> TYPE: DNA
<213> ORGANISM: Bos taurus
<220> FEATURE:
<221> NAME/KEY: variation
<222> LOCATION: (6)..(6)
<223> OTHER INFORMATION: cytosine (C) to thyamine (T) substitution
      polymorphism

<400> SEQUENCE: 12
tgtctctgtt c                                                              11

<210> SEQ ID NO 13
<211> LENGTH: 14
<212> TYPE: DNA
<213> ORGANISM: Bos taurus
<220> FEATURE:
<221> NAME/KEY: variation
<222> LOCATION: (7)..(8)
<223> OTHER INFORMATION: adenine (A)-adenine (A) to guanine(G)-cytosine
      (C) substitution polymorphism
      AA corresponds to the Q allele
      GC corresponds to the q allele

<400> SEQUENCE: 13
ggtaagaagg ccaa                                                           14

<210> SEQ ID NO 14
<211> LENGTH: 11
<212> TYPE: DNA
<213> ORGANISM: Bos taurus
<220> FEATURE:
<221> NAME/KEY: variation
<222> LOCATION: (6)..(6)
<223> OTHER INFORMATION: guanine (G) to adenine (A) substitution
      polymorphism

<400> SEQUENCE: 14
gcggtgagga t                                                              11

<210> SEQ ID NO 15
<211> LENGTH: 16
<212> TYPE: DNA
<213> ORGANISM: Bos taurus
<220> FEATURE:
<221> NAME/KEY: variation
<222> LOCATION: (6)..(7)
<223> OTHER INFORMATION: guanine (G)-guanine (G) to adenine (A)-cytosine
```

(C) substitution polymorphism GG-AC

<400> SEQUENCE: 15
gggggggggg gactct                                                    16

<210> SEQ ID NO 16
<211> LENGTH: 11
<212> TYPE: DNA
<213> ORGANISM: Bos taurus
<220> FEATURE:
<221> NAME/KEY: variation
<222> LOCATION: (6)..(6)
<223> OTHER INFORMATION: adenine (A) to guanine (G) substitution
      polymorphism

<400> SEQUENCE: 16
gagtgacctg c                                                         11

<210> SEQ ID NO 17
<211> LENGTH: 11
<212> TYPE: DNA
<213> ORGANISM: Bos taurus
<220> FEATURE:
<221> NAME/KEY: variation
<222> LOCATION: (6)..(6)
<223> OTHER INFORMATION: cytosine (C) to thymidine (T) substitution
      polymorphism

<400> SEQUENCE: 17
ggacgcgtgg g                                                         11

<210> SEQ ID NO 18
<211> LENGTH: 11
<212> TYPE: DNA
<213> ORGANISM: Bos taurus
<220> FEATURE:
<221> NAME/KEY: variation
<222> LOCATION: (6)..(6)
<223> OTHER INFORMATION: guanine (G) to adenine (A) substitution
      polymorphism

<400> SEQUENCE: 18 ggtggggtg g                                                          11

<210> SEQ ID NO 19
<211> LENGTH: 11
<212> TYPE: DNA
<213> ORGANISM: Bos taurus
<220> FEATURE:
<221> NAME/KEY: variation
<222> LOCATION: (6)..(6)
<223> OTHER INFORMATION: ctosine (C) to thymidine (T) substitution
      polymorphism

<400> SEQUENCE: 19
ctgggcgcag c                                                         11

<210> SEQ ID NO 20
<211> LENGTH: 14
<212> TYPE: DNA
<213> ORGANISM: Bos taurus

<400> SEQUENCE: 20
cgttggcctt ctta                                                      14

<210> SEQ ID NO 21
<211> LENGTH: 14

-continued

```
<212> TYPE: DNA
<213> ORGANISM: Bos taurus

<400> SEQUENCE: 21
ttggccgcct tacc                                                                14
```

The invention claimed is:

1. A method of identifying a bovine, or sample derived from said bovine, with a nucleic acid composition indicative of increased milk volume production in said bovine, the method comprising the steps of:
   (a) providing nucleic acids from said bovine, or a sample derived from said bovine where said sample comprises nucleic acids from said bovine;
   (b) detecting, in said nucleic acids, the presence of nucleotides G and C at positions 6829 and 6830 respectively in SEQ ID NO: 1; and
   (c) identifying said bovine or said sample with nucleotides G and C at positions 6829 and 6830 respectively in SEQ ID NO: 1 as one that possesses a nucleic acid composition indicative of increased milk volume production.

2. The method of claim 1, wherein detection of the presence of the nucleotides G and C is made via amplification of a nucleic acid sequence comprising the nucleotides.

3. The method of claim 2, wherein primers consisting of SEQ ID NOs: 20 and 21 are used in the amplification.

4. The method of claim 1, wherein detection of the presence of the nucleotides G and C is made using an oligonucleotide ligation assay (OLA).

5. The method of claim 4, wherein the OLA is performed using at least one primer consisting of the sequence of SEQ ID NO: 54 or 56.

6. The method of claim 1, in which detection of the nucleotides G and C is made via hybridization of a probe consisting of a sequence complementary to at least 5 contiguous nucleotides of the sequence or complement of SEQ ID NO: 1 that comprises said G and C, wherein the probe is capable of hybridization to said sequence or complement of SEQ ID NO: 1 in 6x sodium citrate/sodium chloride (SSC) at 45° C.

7. A method of selecting a bovine with a nucleic acid composition indicative of increased milk volume production, the method comprising the steps:
   (i) identifying a bovine, with a nucleic acid composition indicative of altered milk volume production, by the method of claim 1, and
   (ii) selecting the bovine, identified in step (i).

8. A method of identifying a bovine, or sample derived from said bovine, with a nucleic acid composition indicative of decreased milk volume production in said bovine, the method comprising the steps of:
   (a) providing nucleic acids from said bovine, or a sample derived from said bovine where said sample comprises nucleic acids from said bovine;
   (b) detecting, in said nucleic acids, the presence of nucleotides A and A at positions 6829 and 6830 respectively in SEQ ID NO: 1; and
   (c) identifying said bovine or said sample with nucleotides A and A at positions 6829 and 6830 respectively in SEQ ID NO: 1 as one that possesses a nucleic acid composition indicative of decreased milk volume production.

9. The method of claim 8, wherein detection of the presence of the nucleotides A and A is made via amplification of a nucleic acid sequence comprising the nucleotides.

10. The method of claim 9, wherein primers consisting of SEQ ID NOs: 20 and 21 are used in the amplification.

11. The method of claim 8, wherein detection of the presence of the nucleotides A and A is made using an oligonucleotide ligation assay (OLA).

12. The method of claim 11, wherein the OLA is performed using at least one primer consisting of the sequence of SEQ ID NO: 55 or 56.

13. The method of claim 8, in which detection of the nucleotides A and A is made via hybridization of a probe consisting of a sequence complementary to at least 5 contiguous nucleotides of the sequence or complement of SEQ ID NO: 1 that comprises said A and A, wherein the probe is capable of hybridization to said sequence or complement of SEQ ID NO: 1 in 6x sodium citrate/sodium chloride (SSC) at 45° C.

14. A method of selecting a bovine with a nucleic acid composition indicative of decreased milk volume production, the method comprising identifying a bovine by the method of claim 8 and selecting the bovine that is identified.

* * * * *